US012769397B2

(12) United States Patent
Moses et al.

(10) Patent No.: US 12,769,397 B2
(45) Date of Patent: Oct. 20, 2026

(54) DEVICES, METHODS, AND GRAPHICAL USER INTERFACES FOR IMPROVING TEXT CONTENT GENERATED BASED ON DECODED BRAIN SIGNALS

(71) Applicant: Echo Neurotechnologies Corporation, San Francisco, CA (US)

(72) Inventors: David Aaron Moses, San Francisco, CA (US); Adam Schembri Bildersee, San Carlos, CA (US); Craig Watson, San Francisco, CA (US); Shefali Prashant Shah, Silver Spring, MD (US)

(73) Assignee: Echo Neurotechnologies Corporation, San Francisco, CA (US)

( * ) Notice: Subject to any disclaimer, the term of this patent is extended or adjusted under 35 U.S.C. 154(b) by 0 days.

(21) Appl. No.: 19/636,797

(22) Filed: Apr. 1, 2026

(65) Prior Publication Data

US 2026/0310294 A1 Oct. 8, 2026

Related U.S. Application Data

(60) Provisional application No. 63/783,931, filed on Apr. 4, 2025.

(51) Int. Cl.

*G06F 3/01* (2006.01)
*A61B 5/372* (2021.01)

(Continued)

(52) U.S. Cl.

CPC .............. *G06F 3/015* (2013.01); *A61B 5/372* (2021.01); *A61B 5/384* (2021.01); *G06F 3/0236* (2013.01);

(Continued)

(58) Field of Classification Search

CPC ...... G06F 3/015; G06F 3/0236; G06F 3/0482; G06F 3/04895; A61B 5/372; A61B 5/384

See application file for complete search history.

(56) References Cited

U.S. PATENT DOCUMENTS 7,546,158 B2 * 6/2009 Allison .................. G06F 3/015 60/545
9,824,689 B1 11/2017 Shapiro (Continued)

OTHER PUBLICATIONS

Lamon Wood, How to use Windows' Built in Speech Recognition, Computerworld, Dec. 21, 2017, available at: https://www.computerworld.com/article/1715231/how-to-use-windows-speech-recognition.html#%3A~%3Atext=Suddenly%2C%20everything%20on%20the%20screen%2C%E2%80%9Cshift%2Dclick.%E2%80%9D%29, 9 pgs.

(Continued)

*Primary Examiner* — Benyam Ketema
(74) *Attorney, Agent, or Firm* — Morgan, Lewis & Bockius LLP

(57) ABSTRACT

A computer system decodes a set of brain signals associated with attempted activation of motor functions of a human subject. The system determines that the decoded set of brain signals includes an instruction to enter text. In accordance with the determination, the system generates instructions to display a preview of text content in a preview region of a system user interface for revising text content of a system application. The text content includes one or more tokens. When the text content meets a set of refinement criteria, including a criterion that a token from the one or more tokens is identified as a target for revision, the system visually emphasizes the token relative to other tokens. After a process for revising the text content is initiated, the system generates instructions to display selectable options corresponding to suggestions for revising the token.

20 Claims, 27 Drawing Sheets

(51) Int. Cl.
*A61B 5/384* (2021.01)
*G06F 3/023* (2006.01)
*G06F 3/0482* (2013.01)
*G06F 3/04895* (2022.01)

(52) U.S. Cl.
CPC ........ *G06F 3/0482* (2013.01); *G06F 3/04895* (2013.01)

(56) References Cited

U.S. PATENT DOCUMENTS

| | | | | |
|---|---|---|---|---|
| 11,402,909 | B2 * | 8/2022 | Forsland | A61B 5/378 |
| 11,543,885 | B2 * | 1/2023 | Johnson | A61B 5/165 |
| 11,771,362 | B2 * | 10/2023 | Seidman | A61B 5/0075 600/476 |
| 11,883,181 | B2 * | 1/2024 | Ojeda | A61B 5/0075 |
| 12,078,531 | B2 * | 9/2024 | Henninger | A61B 5/0075 |
| 12,223,106 | B2 * | 2/2025 | Oxley | G06F 3/015 |
| 2006/0125659 | A1 * | 6/2006 | Kim | G06F 3/015 341/20 |
| 2007/0162256 | A1 * | 7/2007 | Verma | G06F 3/015 702/182 |
| 2009/0247895 | A1 * | 10/2009 | Morikawa | A61B 5/378 600/544 |
| 2010/0280403 | A1 * | 11/2010 | Erdogmus | A61B 5/377 600/545 |
| 2011/0260830 | A1 * | 10/2011 | Weising | A63F 13/40 340/5.52 |
| 2014/0228701 | A1 * | 8/2014 | Chizeck | A61B 5/372 600/544 |
| 2014/0266646 | A1 * | 9/2014 | Urbach | G06F 3/011 340/407.1 |
| 2014/0333529 | A1 * | 11/2014 | Kim | G06F 3/015 345/156 |
| 2015/0045007 | A1 * | 2/2015 | Cash | A61B 5/374 455/418 |
| 2015/0346810 | A1 * | 12/2015 | Urbach | G06F 3/013 345/501 |
| 2017/0281086 | A1 * | 10/2017 | Donaldson | A61B 5/1118 |
| 2019/0220188 | A1 * | 7/2019 | Pham | G06F 3/013 |
| 2020/0393902 | A1 * | 12/2020 | Mann | A61B 5/14553 |
| 2021/0064135 | A1 * | 3/2021 | Shenoy | G06F 18/2148 |
| 2021/0223864 | A1 * | 7/2021 | Forsland | A61B 5/378 |
| 2021/0271496 | A1 * | 9/2021 | Srivastava | G06F 9/453 |
| 2024/0029728 | A1 | 1/2024 | D'Ercole et al. | |
| 2024/0148324 | A1 * | 5/2024 | Connor | G02C 5/143 |
| 2024/0160288 | A1 * | 5/2024 | Hopkins | G06F 21/31 |
| 2024/0338075 | A1 * | 10/2024 | Esaka | G06F 3/01 |

OTHER PUBLICATIONS

Lance Whitney, Speak Up: How to use Speech Recognition and Dictate Text, PCMag, Oct. 17, 2022, available at: https://www.pcmag.com/how-to/speak-up-how-to-use-speech-recognition-and-dictate-text-in-windows, 23 pgs.

* cited by examiner

Figure 2A inset

DEVICES, METHODS, AND GRAPHICAL USER INTERFACES FOR IMPROVING TEXT CONTENT GENERATED BASED ON DECODED BRAIN SIGNALS

RELATED APPLICATIONS

This application claims priority to U.S. Provisional Patent Application No. 63/783,931, filed Apr. 4, 2025, titled "Devices, Methods, and Graphical User Interfaces for Improving Text Content Generated Based on Decoded Brain Signals," which is incorporated by reference herein in its entirety.

TECHNICAL FIELD

The disclosed embodiments relate generally to brain-computer user interfaces, and more specifically to systems, methods, and user interfaces for previewing and revising neural text output.

BACKGROUND

Neurological conditions can result in the loss of communication and motor control. Brain computer interface (BCI) technologies can assist individuals with neurological impairments, by capturing brain signals from the brain and decoding the brain signals to determine intended user actions for controlling external devices or computer systems.

SUMMARY

Accordingly, there is a need for improved devices, methods, and interfaces for processing text input generated from decoded brain signals for use with software applications. Such methods and interfaces optionally complement or replace conventional methods for user-computer interaction, including speech-based and motor-input techniques. In some embodiments, the disclosed methods allow users, including a user with speech and/or motor impairments, to interact with software applications on computers, including generate text for an application, preview the text in a system user interface before the text is committed to the application, and revise one or more tokens of the text when refinement criteria are met. Such methods and interfaces can improve reliability and usability of a BCI text-entry system by enabling targeted revision of text content generated from decoded brain signals before submission to the application. The disclosed methods and interfaces reduce propagation of decoding errors into application text and enables more efficient revision of text generated from neural input.

The above deficiencies and other problems associated with user interfaces for electronic devices (or more generally, computer systems) are reduced or eliminated by the disclosed devices. In some embodiments, the device is a desktop computer. In some embodiments, the device is portable (e.g., a notebook computer, tablet computer, or handheld device). In some embodiments, the device is a personal electronic device (e.g., a wearable electronic device, such as a watch). In some embodiments, the device has a touchpad. In some embodiments, the device has a touch-sensitive display (also known as a "touch screen" or "touch-screen display"). In some embodiments, the device has a graphical user interface (GUI), one or more processors, memory and one or more modules, programs or sets of instructions stored in the memory for performing multiple functions. In some embodiments, the user interacts with the GUI through stylus and/or finger contacts and gestures on the touch-sensitive surface. In some embodiments, the functions optionally include image editing, drawing, presenting, word processing, spreadsheet making, game playing, telephoning, video conferencing, e-mailing, instant messaging, workout support, digital photographing, digital videoing, web browsing, digital music playing, note taking, and/or digital video playing. Executable instructions for performing these functions are, optionally, included in a non-transitory computer readable storage medium or other computer program product configured for execution by one or more processors.

In accordance with some embodiments, a method is performed at a computer system that is in communication with a display generation component and one or more input devices. The method includes decoding a set of brain signals that are received from a brain of a human subject. The set of brain signals is associated with attempted activation of motor functions of the human subject. The method includes determining that the decoded set of brain signals includes an instruction to enter text. The method includes, in accordance with the determination that the decoded set of signals includes an instruction to enter text, generating instructions to display, via the display generation component, a preview of text content in a preview region of a system user interface for revising text content of a system application. The text content is generated based on the decoded set of brain signals and the text content includes one or more tokens. The method includes, in accordance with a determination that the text content meets a set of one or more refinement criteria, wherein the set of one or more refinement criteria includes a criterion that a token from the one or more tokens is identified as a target for revision, generating instructions to cause the token to be visually emphasized relative to other tokens of the one or more tokens. The method includes detecting a user input requesting initiation of a process for revising the text content. The method also includes in response to detecting the user input requesting initiation of the process for revising the text content, initiating the process for revising the text content, including generating instructions to display a plurality of selectable options corresponding to suggestions for revising the token.

In accordance with some embodiments, a brain computer interface (BCI) system includes an implant device configured to record a set of neural signals from a brain of a human subject, wherein the set of neural signals is associated with attempted activation of motor functions of the human subject. The BCI system includes one or more processors and memory coupled to the one or more processors. The memory stores one or more programs configured for execution by the one or more processors. The one or more programs include instructions for (i) decoding the set of neural signals to obtain a neural text output; (ii) in accordance with the decoding, generating instructions to display a preview of text content in a preview region of a system user interface, wherein the text content is generated based on the decoded set of neural signals and includes one or more tokens; (iii) identifying, based on a property of the decoded neural text output, a token from the one or more tokens as a target for revision; (iv) generating instructions to cause the token to be visually emphasized relative to other tokens of the one or more tokens; (v) detecting a user input requesting initiation of a process for revising the text content; and (vi) in response to detecting the user input requesting initiation of the process for revising the text content, initiating the process for revising the text content, including generating instructions to display a plurality of selectable options corresponding to suggestions for revising the token.

In accordance with some embodiments, a computing device includes a display, one or more processors, and memory coupled to the one or more processors. The memory stores one or more programs configured for execution by the one or more processors. The one or more programs include instructions for performing any of the methods disclosed herein.

In accordance with some embodiments, a computer system includes one or more processors, and memory coupled to the one or more processors. The memory stores one or more programs configured for execution by the one or more processors. The one or more programs include instructions for performing any of the methods disclosed herein.

In accordance with some embodiments, a non-transitory computer readable storage medium stores one or more programs configured for execution by a computing device having a display, one or more processors, and memory. The one or more programs include instructions for performing any of the methods disclosed herein.

In accordance with some embodiments, a non-transitory computer readable storage medium stores one or more programs configured for execution by a computer system having one or more processors, and memory. The one or more programs include instructions for performing any of the methods disclosed herein.

Note that the various embodiments described above can be combined with any other embodiments described herein. The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes and may not have been selected to delineate or circumscribe the inventive subject matter.

BRIEF DESCRIPTION OF THE DRAWINGS

For a better understanding of the aforementioned systems, methods, and graphical user interfaces, reference should be made to the Detailed Description of Embodiments below, in conjunction with the following drawings in which like reference numerals refer to corresponding parts throughout the figures. The accompanying drawings, which are included to provide a further understanding of the embodiments, are incorporated herein, constitute a part of the specification, illustrate the described embodiments, and, together with the description, serve to explain the underlying principles.

Like reference numerals refer to corresponding parts throughout the several views of the drawings.

DETAILED DESCRIPTION OF EMBODIMENTS

Figure 1A:
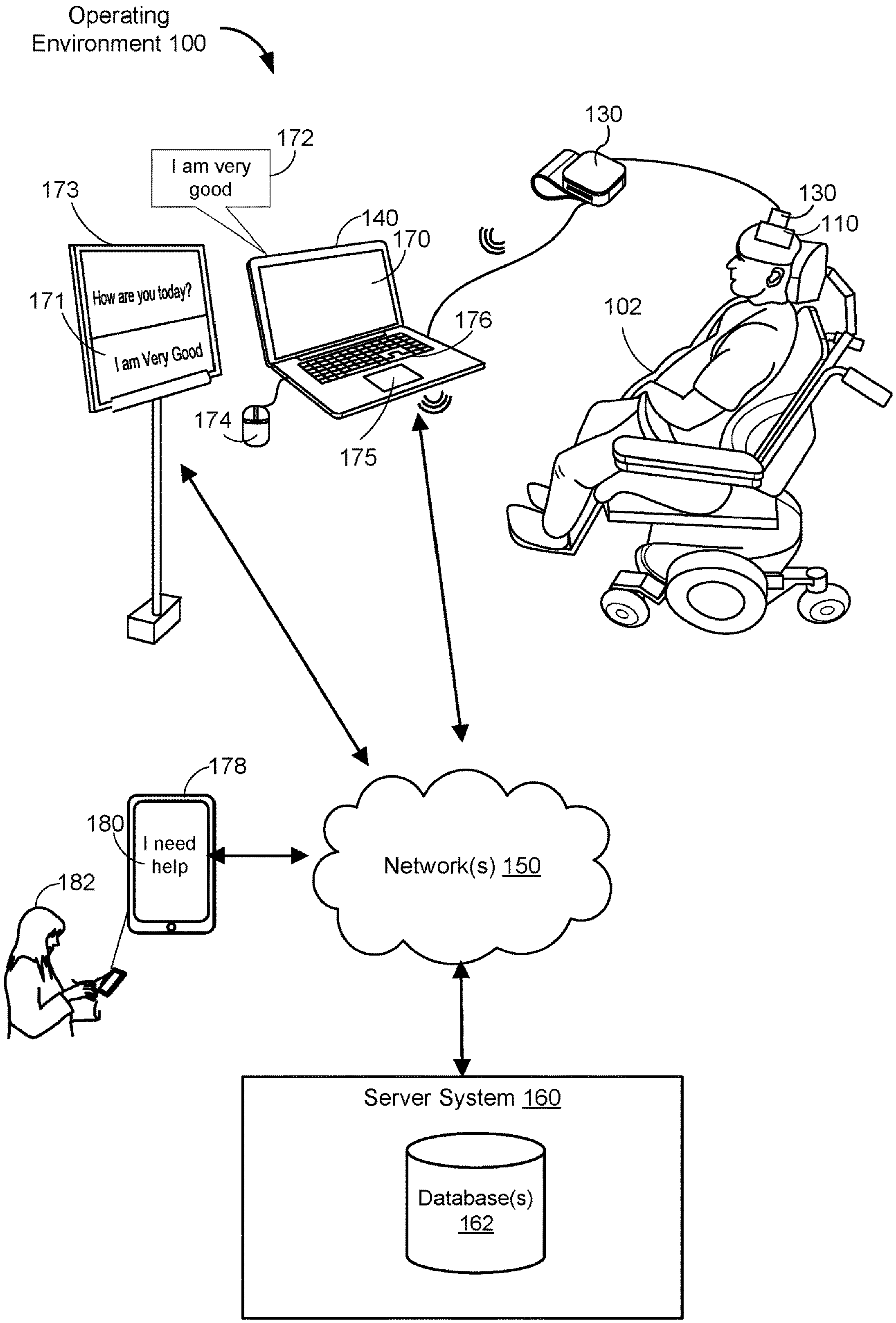
FIG. 1A illustrates an example operating environment, in accordance with some embodiments.

Software applications available on computer systems (e.g., personal computers and electronic devices) have user interfaces and input mechanisms that are inefficient, cumbersome, and difficult to operate and control, especially for users with speech and motor impairments. Mechanisms for capturing user input and translating that input into actions may require certain level of motor control, speech control, and/or dexterity that are inaccessible to some users with impairments. Such user interfaces and input mechanisms provide insufficient accommodation for users with speech and motor impairments. For example, some mechanisms require that a user can move their hands and fingers to type on a keyboard, move a pointing device (e.g., in order to move a cursor on a screen), move their fingers across touch-sensitive surfaces (e.g., in order to interact with user interfaces), ability to speak in order to provide speech commands as input, ability to provide physical input via joysticks, styluses, buttons, and/or other mechanisms for capturing user input. Such applications and input mechanisms can be time-consuming, error-prone, tedious, and create significant burden to some users with motor and/or speech impairments.

Accordingly, there is a need for computer systems with improved methods and interfaces for providing computer-generated experiences to users with motor and/or speech impairments. In some embodiments, brain-computer interface technologies are used to decode user inputs from the user's brain activity. Sometimes, the output generated based on the user's brain activity can be imprecise, incorrect, and/or need improvement and refinement. These deficiencies and other problems associated with user interfaces for electronic devices (or more generally, computer systems) are reduced or eliminated by the disclosed methods and systems. In some embodiments, a system user interface is provided for refining and adjusting neural text output. The system user interface optionally operates in two modes: (1) a dictate mode and (2) a refine mode. In the dictate mode, the computer system continuously processes brain activity (e.g., electrical or optical brain signals), decodes the brain activity to generate neural text output, and automatically types the generated neural text output into a preview region of the system user interface. Typing the generated neural text output into the preview region provides continuous visual feedback to the user regarding whether the computer system is accurately decoding the brain activity, thereby allowing the user to adjust and refine their brain activity and/or to adjust and refine the generated neural text output. In accordance with a determination that fragments of the neural text output are identified as targets for revision (e.g., based on various machine learning and/or rule-based algorithms), the computer system visually emphasizes the identified fragments and, optionally, displays a user interface control for activating the refine mode of the system user interface. In the refine mode, the computer system ceases to continuously generate and type neural text output, thereby reducing the need for computing resources to actively process and decode detected brain activity into neural text output and improving efficiency of the computer-user interaction. In some embodiments, transitioning from the dictate mode to the refine mode reduces processor utilization, memory bandwidth consumption, wireless traffic associated with nonessential neural decoding, and power consumption, while maintaining responsiveness for revision operations. In the refine mode, neural text output is revised by selecting system-generated options for revising the neural text content. In the refine mode, the computer system displays options corresponding to suggestions for revising the respective fragment of the neural text output, where the options are selectable using neural-based inputs in addition to conventional user inputs, thereby providing accommodation for users with motor and/or speech impairments. For example, a visual indication of a respective command for selecting a respective option is displayed in the system user interface, where when a neural-based input corresponding to a respective command (e.g., attempted speech) is detected, the computer system selects the respective option and, optionally, replaces the respective fragment of the neural text output with the selected option. Automatically displaying options for revising neural text input, where the options can be selected in response neural-based inputs, provides additional control to the user to revise and refine neural text output with different input modalities and/or reduces the number of inputs and/or amount of time needed to enter text input into a text region of an application user interface (e.g., by reducing the number of errors in neural text output). The ability to switch between the dictate mode and the refine mode enhances the operability of the device and makes the user-device interface more efficient (e.g., by helping the user to provide proper inputs and reducing user mistakes when operating/interacting with the device) and, additionally, reduces power usage, memory usage, and usage of other computational resources and/or improves battery life of the device by enabling the user to use the device more quickly and efficiently.

The processes described below enhance the operability of the devices and make the user-device interfaces more efficient (e.g., by helping the user to provide proper inputs and reducing user mistakes when operating/interacting with the device) through various techniques, including by providing improved visual, audio, and/or tactile feedback to the user, providing additional control to the user via neural inputs, reducing the number of inputs needed to perform an operation, providing additional control options without cluttering the user interface with additional displayed controls, performing an operation when a set of conditions has been met without requiring further user input, and/or additional techniques. These techniques also reduce power usage and improve battery life of the device by enabling the user to use the device more quickly and efficiently.

In addition, in methods described herein where one or more steps are contingent upon one or more conditions having been met, it should be understood that the described method can be repeated in multiple repetitions so that over the course of the repetitions all of the conditions upon which steps in the method are contingent have been met in different repetitions of the method. For example, if a method requires performing a first step if a condition is satisfied, and a second step if the condition is not satisfied, then a person of ordinary skill would appreciate that the claimed steps are repeated until the condition has been both satisfied and not satisfied, in no particular order. Thus, a method described with one or more steps that are contingent upon one or more conditions having been met could be rewritten as a method that is repeated until each of the conditions described in the method has been met. This, however, is not required of system or computer readable medium claims where the system or computer readable medium contains instructions for performing the contingent operations based on the satisfaction of the corresponding one or more conditions and thus is capable of determining whether the contingency has or has not been satisfied without explicitly repeating steps of a method until all of the conditions upon which steps in the method are contingent have been met. A person having ordinary skill in the art would also understand that, similar to a method with contingent steps, a system or computer readable storage medium can repeat the steps of a method as many times as are needed to ensure that all of the contingent steps have been performed.

Reference will now be made in detail to specific embodiments, examples of which are illustrated in the accompanying drawings. In the following detailed description, numerous non-limiting specific details are set forth in order to assist in understanding the subject matter presented herein. But it will be apparent to one of ordinary skill in the art that various alternatives may be used without departing from the scope of the claims and the subject matter may be practiced without these specific details. For example, it will be apparent to one of ordinary skill in the art that the subject matter presented herein can be implemented on many types of electronic devices with digital video capabilities.

FIG. 1A illustrates an example operating environment 100 of a brain computer interface (BCI) system, in accordance with some embodiments.

As used herein, a BCI system is a system that acquires brain signals from a user and determines, from the signals, one or more intended actions (e.g., functional intents) of the user. In some embodiments, in response to neural-based inputs, the BCI system generates and executes commands for controlling computer systems and/or one or more external devices (e.g., without requiring inputs from the user that require motor control). Because the BCI-system allows the user to provide neural inputs in addition to conventional user inputs, the BCI system can assist users with motor, speech, and other impairments, thereby enhancing the user's capabilities and improving their quality of life.

The operating environment 100 depicts a human subject 102. As used herein, human subject 102 is also referred to as a "patient" or a "user." In some instances, the human subject 102 is unable to speak or unable to move their limbs. In some embodiments, the BCI system includes an implant device 110 (also referred to herein as a cranial implant device), which is implanted into the skull of the human subject 102. The implant device 110 includes an array of high-density electrode sensors for recording neural signals (e.g., electrical signals) corresponding to motor cortex activity directly from the brain surface of the human subject 102. In some embodiments, the array is a brain-penetrating electrode array or an electrocorticography (ECOG) electrode array. In some embodiments, the electrodes are depth electrodes or surface electrodes. In some embodiments, the recorded neural signals represent specific activities of the brain, including attempted speech, attempted movement, hearing, and/or vision. In some embodiments, the array of electrode sensors is placed on the cortical surface of the brain, either epidurally or subdurally, to record signals directly from the brain. In some embodiments, the array of electrode sensors can penetrate under the scalp.

In some embodiments, the BCI system includes a wearable device 130. As described in further detail in FIG. 3A, in some embodiments the wearable device 130 includes a patch component that is magnetically and communicatively coupled to the implant device 110. The patch component is configured to transmit power wirelessly into the implant device 110 and receive neural signal data from the implant device 110. In some embodiments, the wearable device 130 includes a relay component that includes electronics for supporting the functionalities of the patch component.

In some embodiments, the BCI system includes a computing device 140 that is communicatively connected with the wearable device 130. The computing device 140 can include a display 170, a keyboard 176 and a pointing device such as a mouse 174 or a touchpad 175. In accordance with some embodiments, the computing device 140 functions as the main interface for the human subject 102. For example, the human subject 102 can access one or more applications executing on the computing device 140 for their daily tasks and activities such as checking email and browsing the web. In some embodiments, the one or more applications executing on the computing device 140 includes a BCI application (e.g., application 440) that is configured to decode the neural signals and interpret the decoded signals to determine one or more intended actions (e.g., functional intents) of the human subject 102. In some embodiments, the BCI application applies one or more machine learning models that are stored locally on the computing device 140 to perform the decoding and interpreting. In some embodiments, the BCI application is configured to execute on the computing device 140 even while the computing device 140 is offline (although an internet connection will be required to receive new models from the server system 160).

In some embodiments, the BCI system includes a server system 160 that is communicatively coupled to the computing device 140 through one or more communication networks 150. The server system 160 includes an operational pipeline that is configured to automatically generate different machine learning models based on respective input data, train the models to optimize their performance on specific tasks, and deploy the models locally on respective computing devices 140. In some embodiments, the server system 160 includes one or more databases 162 for storing data such as raw data obtained from implanted devices corresponding to respective patients, feature data, analytics data, application information, and firmware versions.

With continued reference to FIG. 1A, in some embodiments, the BCI system is configured to control one or more output devices to carry out one or more intended actions of the human subject 102 according to the decoded signals. As one example, in some embodiments, the BCI system (e.g., computing device 140 or server system 160) is configured to control a keyboard (e.g., physical keyboard 176 or a virtual keyboard) to generate language and/or numeral outputs according to the decoded signals (e.g., by typing letters, numbers, words and/or sentences using the keyboard), without requiring any voice command and/or limb movement by the human subject 102. As another example, in some embodiments, the BCI system is configured to control a cursor (e.g., by controlling a pointing device such as mouse 174, touchpad 175, or the cursor) according to the decoded signals, without requiring any voice command and/or limb movement by the human subject 102. As another example, in some embodiments, the BCI system is configured to control a display device (e.g., display 170 or external display device 173) to display a visual output (e.g., text entry 171) corresponding to a response from the human subject 102, without requiring any voice command and/or limb movement by the human subject 102. As another example, in some embodiments, the BCI system is configured to translate a visual/text output into a verbal expression and generate an audio output 172 articulating the verbal expression using an audio output component of the computing device 140, without requiring any voice command and/or limb movement by the human subject 102. As another example, in some embodiments, the BCI system is configured to control one or more interfaces of the computing device 140 to navigate through menus and/or switch between tabs of one or more applications executing on the computing device 140, without requiring any voice command and/or limb movement by the human subject 102. As yet another example, in some embodiments, the BCI system is configured to generate an alert according to the decoded signals and transmit the alert to an electronic device 178 that is associated with a caregiver 182 of the human subject 102, for display (e.g., as alert message 180) on a display screen of the electronic device 178.

Figure 1B:
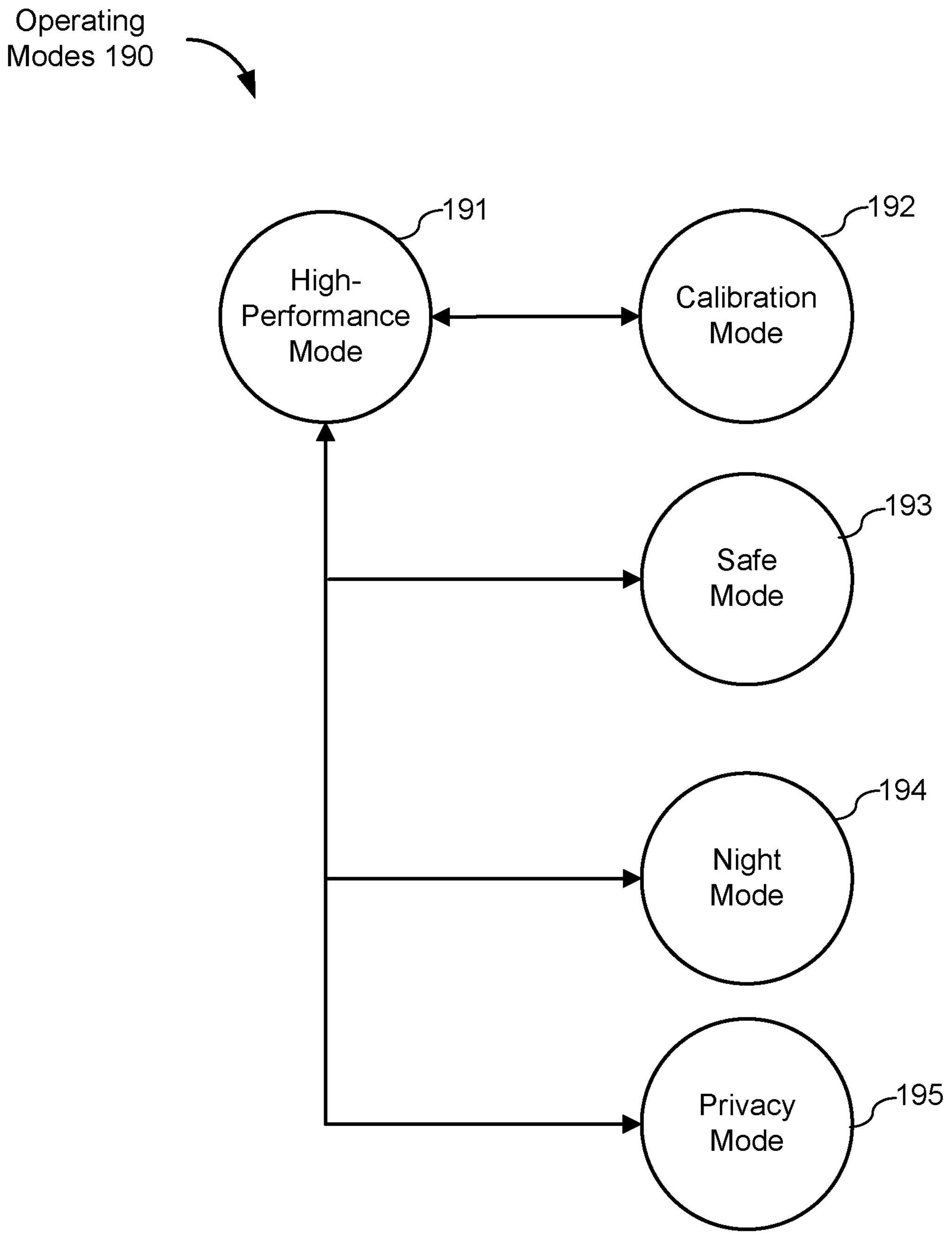
FIG. 1B illustrates example operating modes of a computing device, in accordance with some embodiments.

FIG. 1B illustrates example operating modes 190 of a computing device 140, in accordance with some embodiments.

In accordance with some embodiments, the computing device 140 can switch between various operating modes. A respective operating mode may have its associated (e.g., distinct) user interface. A human subject 102 may interact with the computing device 140 in specific ways, depending on the operating mode.

Referring to FIG. 1B, in some embodiments, the operating modes include a high performance mode 191 that allows a human subject 102 to fully interact with the computing device 140. For example, in the high performance mode 191, the human subject 102 has access to all functionalities of applications that are executing on the computing device. In some embodiments, the high performance mode 191 is also referred as the "normal" mode. In some embodiments, high performance mode 191 is the default operating mode of the computing device.

In some embodiments, the operating modes include a calibration mode 192, which is a sandbox mode used during training tasks.

In some embodiments, the operating modes include a safe mode 193. In some embodiments, the safe mode 193 is a fallback mode for when the high performance mode 191 is not available.

In some embodiments, the operating modes include a night mode 194. When operating in the night mode, the display screen 170 of the computing device 140 is not in use and the computing device 140 has limited functionality due to the screen not being in use.

In some embodiments, the operating modes include a privacy mode 195, where brain signals are not recorded and not decoded.

Figure 1C:
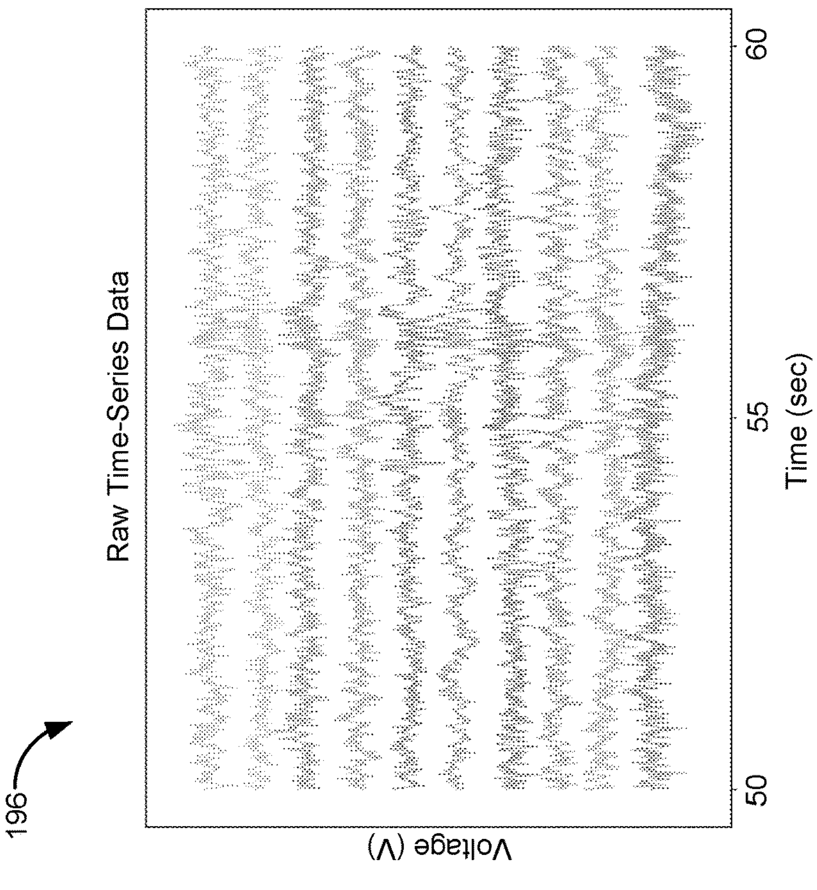
FIG. 1C is a graph showing an actual time-series dataset of neural activity of a patient, in accordance with some embodiments.

FIG. 1C is a graph 196 showing an actual raw time-series dataset of neural activity of a patient collected by an electrode array, in accordance with some embodiments. The dataset is collected by placing electrodes on the surface of the patient's brain. Each of the line plots in the graph 196 corresponds to electrical field signals collected by a respective channel (e.g., an electrode) of the array. The line plots on the graph 196 have been offset for clarity.

Figure 1D:
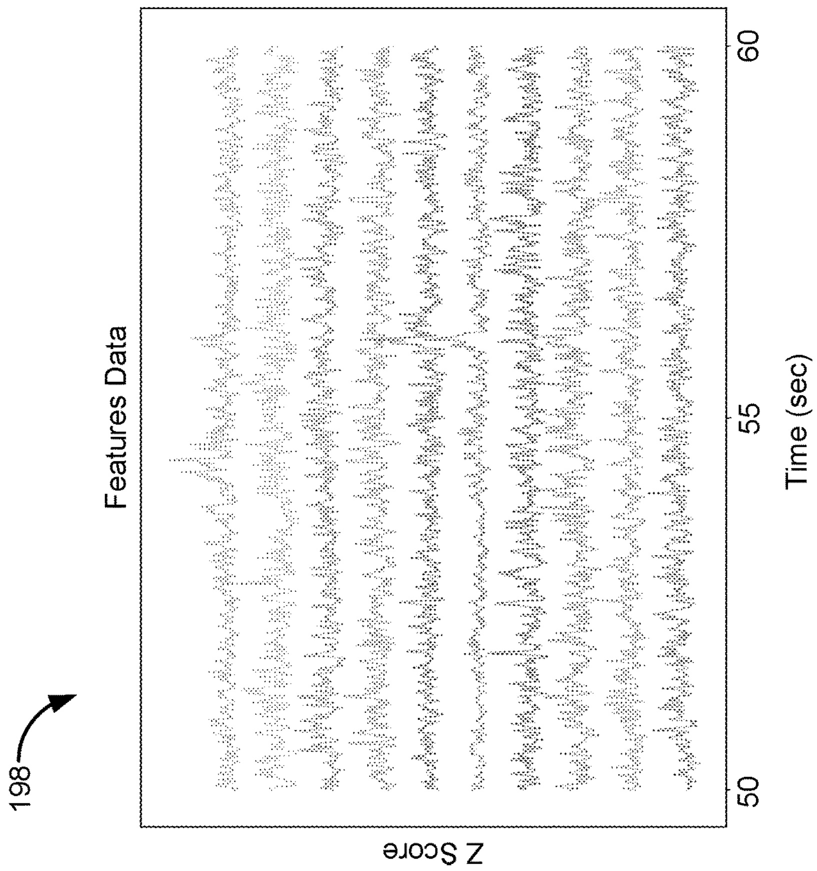
FIG. 1D is a graph showing neural features extracted from the neural activity dataset of FIG. 1C, in accordance with some embodiments.

FIG. 1D is a graph 198 showing a neural-feature time-series dataset extracted from the neural activity data of FIG. 1C, in accordance with some embodiments. In some embodiments, the neural-feature time series dataset is generated using a feature processing pipeline that is executed by the computing device 140 (e.g., application 440) or the server system 160 (e.g., operational pipeline 524). The neural features correspond to representations of brain signals that contain information related to underlying neural processing, including neural representations associated with attempted speech and/or motor movements. The values on the y-axis of the graph 198 are z-score values, which are normalized values that indicate how many standard deviations a data point is from the mean of the dataset (computed individually for each feature time series).

Figure 2A:
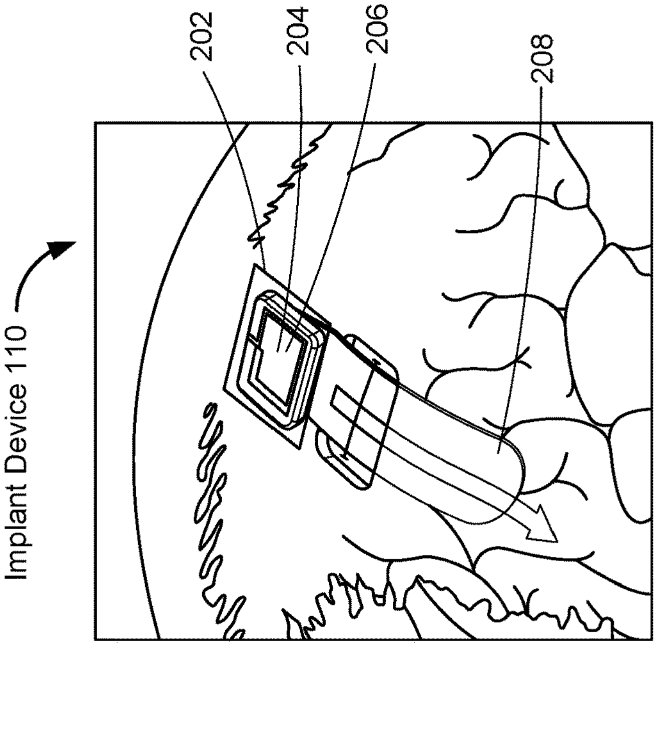
FIGS. 2A, 2B, and 2C illustrate an example implant device, in accordance with some embodiments.
Figure 2B:
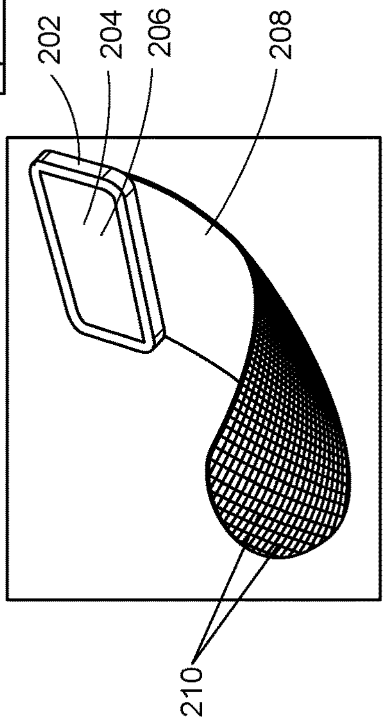
Figure 2B:
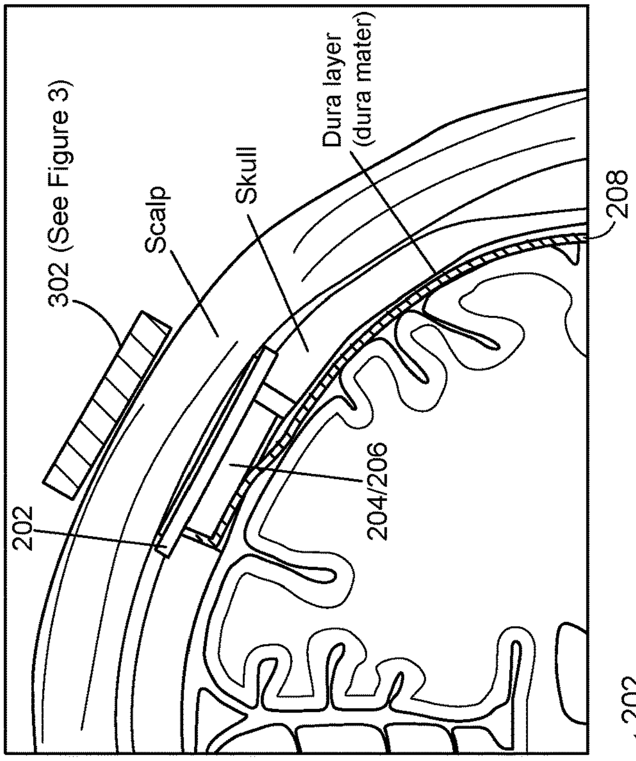
Figure 2C:
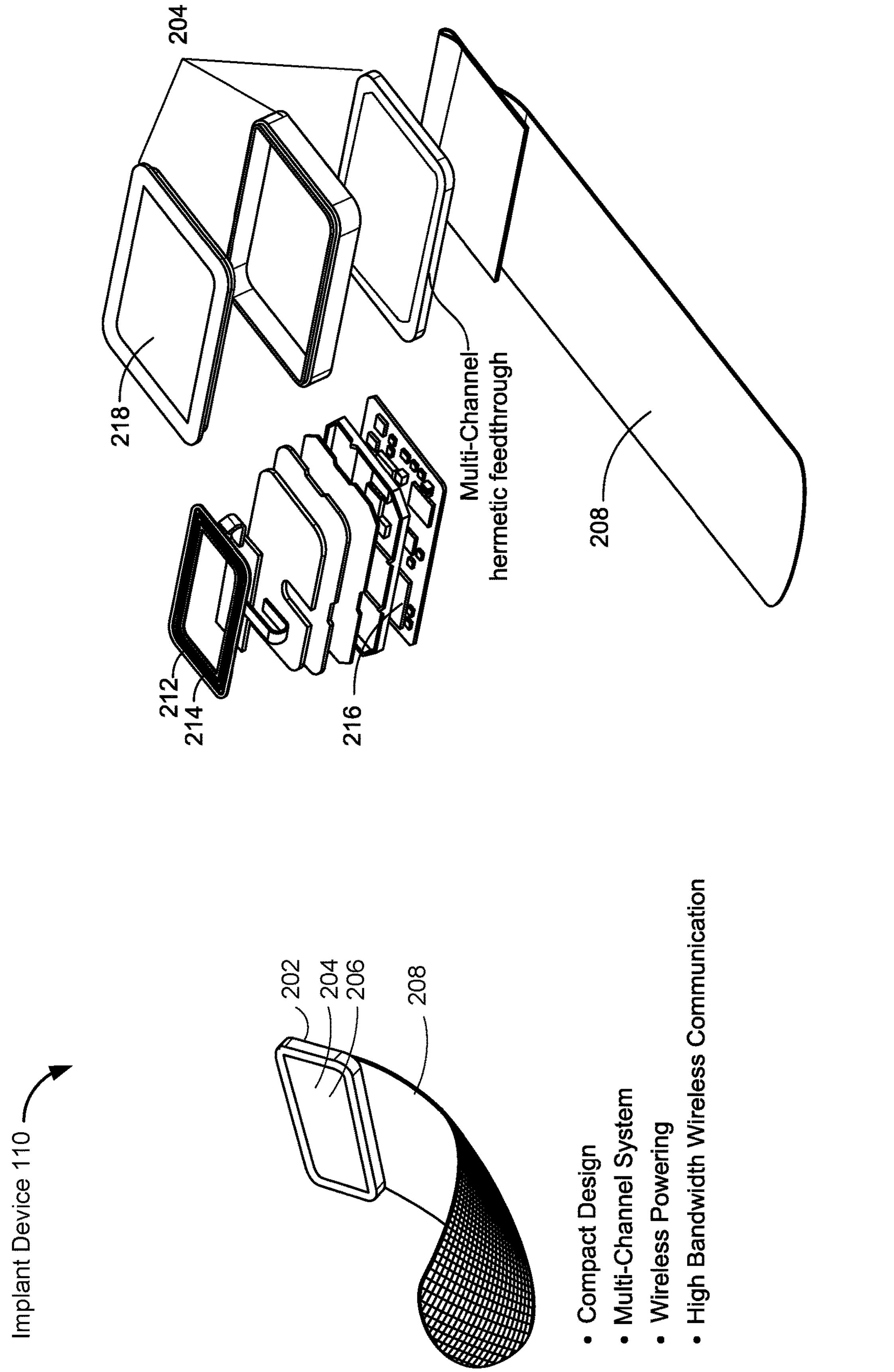

FIGS. 2A, 2B, and 2C illustrate various views of the implant device 110, in accordance with some embodiments.

In some embodiments, the implant device 110 includes a frame 202, a hermetic package 204 (e.g., hermetically-sealed package), implant electronics 206 (e.g., one or more electronic components) enclosed in the hermetic package 204, and an electrode array 208. As used herein, the electrode array 208 is also referred to as "an array of electrodes" or "an array of electrode sensors." FIG. 2A inset shows that the electrode array 208 comprises a thin, flexible array (e.g., with a thickness of around 50 μm to 200 μm) that includes multiple electrode sensors 210. In some embodiments, the electrode array 208 comprises an electrocorticography (ECOG) array that is surgically implanted on the brain's surface.

In some embodiments, the electrode array 208 includes at least 100 electrodes, at least 250 electrodes, at least 500 electrodes, at least 750 electrodes, at least 1000 electrodes, at least 1500 electrodes, at least 2000 electrodes, at least 2500 electrodes, at least 3000 electrodes, at least 4000 electrodes, at least 5000 electrodes, at least 7500 electrodes, or at least 10,000 electrodes. In some embodiments, the electrode array 208 is designed to be placed over a substantial portion of or the entire sensorimotor cortex region, to collect electrophysiologic data with information content of intended speech and movement of a human subject. In some embodiments, the electrode array is designed to be placed over one or more subregions or regions of the cortex, such as the precentral gyrus, postcentral gyrus, posterior superior frontal gyrus, posterior middle frontal gyrus, posterior inferior frontal gyrus region, superior temporal gyrus, or a combination of any of the foregoing. Typically, each electrode 210 of the electrode array 208 corresponds to a channel and is configured to pick up electrical activity from the cortex. A denser electrode array with higher channel count can capture more signals with higher fidelity, which can be used to decode intended actions (e.g., intended speech actions and non-speech actions) of the human subject.

FIG. 2B illustrates a coronal cross-sectional view of a brain of a human subject. In some embodiments, the frame 202 is configured to be anchored to a skull of a human subject 102 via a surgical procedure called craniectomy, in which a scalp incision is made and a full-thickness section of bone is removed from the skull. In the example of FIG. 2B, the frame 202, the hermetic package 204, and the implant electronics 206 are configured to be positioned above the dural layer (e.g., closer to the scalp), whereas the electrode array 208 is inserted into the sub-dural layer (e.g., underneath the dura mater) of the brain of the human subject 102. During device operation, the electrode array 208 is configured to acquire (e.g., record) motor cortex neural signals (e.g., electrical signals) from the brain of the human subject.

In some embodiments, the implant device 110 includes a battery. In some embodiments, the implant device 110 does not include a battery. In some embodiments, the implant device 110 is configured to receive power signals from a patch component 302 of the wearable device 130. In some embodiments, the implant electronics 206 include a wireless powering coil 212 that is configured to receive electrical power wirelessly from the patch component 302. In some embodiments, the hermetic package 204 includes a cover 218 that is composed of a ceramic material or other dielectric material to facilitate the receiving of power signals via inductive coupling or capacitive coupling. In some embodiments, the wireless powering coil 212 is configured to receive constant electrical power from the patch component 302.

FIG. 2B illustrates coupling between the implant device 110 and the patch component 302. In some embodiments, the frame 202 includes one or more magnets that are configured to magnetically couple to one or more complementary magnets positioned at the patch component 302.

In some embodiments, the implant electronics 206 include a wireless communication antenna 214 that is configured to establish a direct wireless link between the implant device 110 and the wearable device 130. In some embodiments, the wireless communication antenna 214 is configured to implement high bandwidth wireless communication to transmit the multiple channels (e.g., hundreds or thousands of channels) of brain signals (e.g., electrical signals) that are collected by the electrode array 208 to the wearable device 130. In some embodiments, the implant device 110 is configured to amplify, digitize, and transmit the signals to the patch component 302 as data packets without interpreting and/or further processing the signals.

In some embodiments, the implant electronics 206 include processing circuitry, communication circuitry, and power circuitry. In some embodiments, the various circuitries are implemented as a multi-channel application-specific integrated circuit (ASIC) chip 216 that enables custom programming of specific tasks. In some embodiments, the ASIC chip 216 is implemented as a system-on-chip (SOC). In some embodiments, the ASIC chip 216 and includes one or more microprocessors and one or more memory blocks such as ROM, RAM, EEPROM, flash memory, or other building blocks.

Figure 2D:
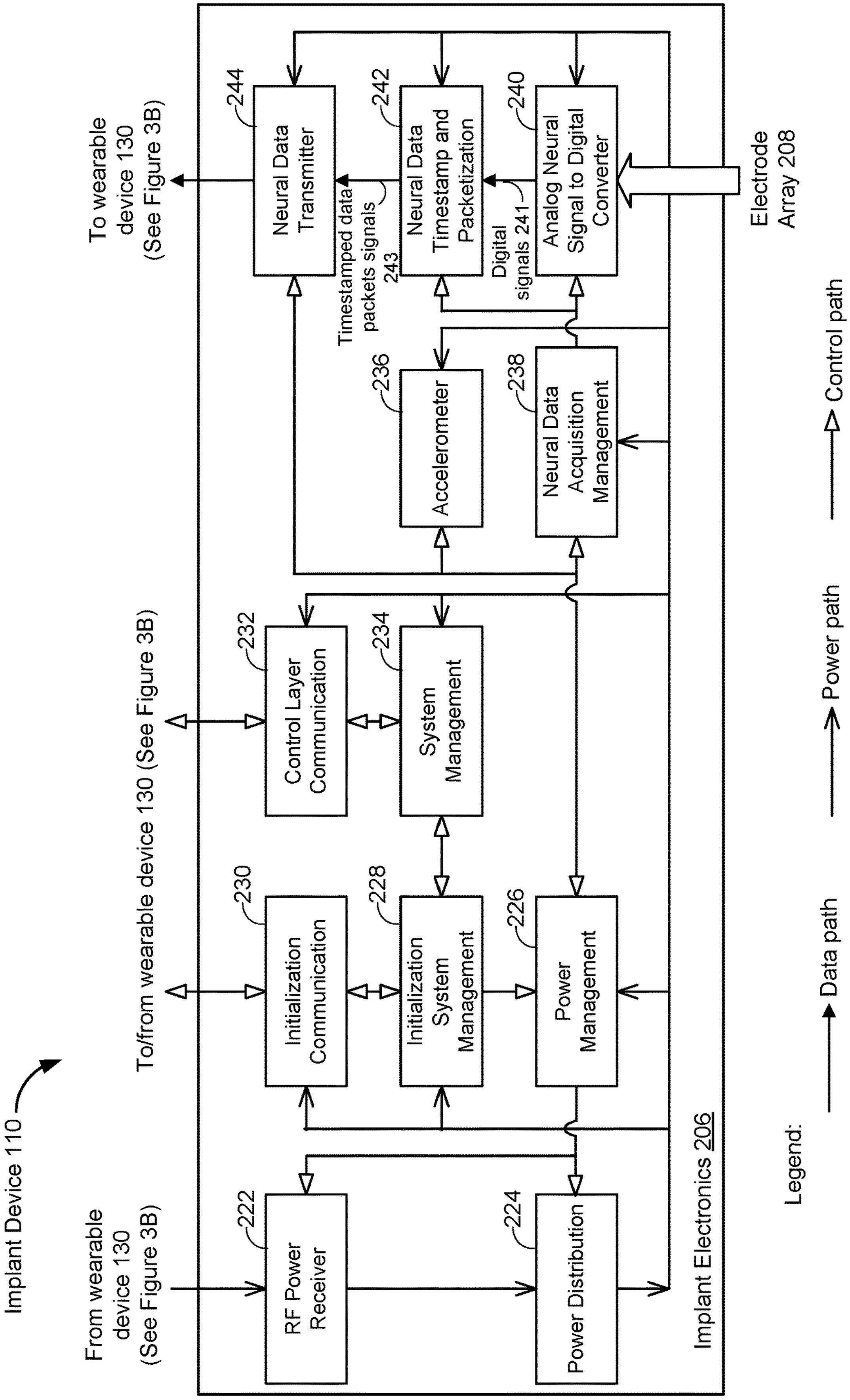
FIG. 2D is a block diagram showing an example data path, control path, and power path of an implant device, in accordance with some embodiments.

FIG. 2D is a block diagram showing an example data path (represented by closed triangle arrows), power path (represented by two-edged arrows), and control path (represented by open triangle arrows) of an implant device 110, in accordance with some embodiments.

The data path of the implant device 110 includes receiving neural signals from the electrode array 208. In some embodiments, the implant device 110 includes an analog neural signal to digital converter module 240 (e.g., an analog to digital converter) for converting the neural signals (e.g., electrical signals) from analog form to digital form (e.g., digital signals 241). The implant device 110 includes a neural data timestamp and packetization module 242 for embedding date/time information to the digital signals and breaking down the digital signals into data packets (e.g., data segments) of smaller data sizes (e.g., timestamped data packets 243). The implant device 110 includes a neural data transmitter module 244 for transmitting the timestamped data packets 243 to the wearable device 130.

In accordance with some embodiments, the implant device 110 does not include a battery (i.e., the implant device 110 is not a battery-operated device). In some embodiments, the implant device 110 receives its power supply from the wearable device 130. In some embodiments, the implant device 110 includes an RF power receiver module 222 for receiving power (e.g., DC power) from the wearable device 130 (e.g., from RF power transmitter module 324 of the wearable device 130) and sending the received power to a power distribution module 224. The power distribution module 224 is configured to distribute the power to the various modules of the implant device 110, including the analog neural signal to digital converter module 240, the neural data timestamp and packetization module 242, the neural data transmitter module 244, a power management module 226, an initialization system management module 228, an initialization communication module 230, a control layer communication module 232, a system management module 234, an accelerometer module 236, and a neural data acquisition module 238.

In some embodiments, the power management module 226 is configured to actively control and monitor the flow of electrical power within the implant device 110. For example, the power management module 226 can regulate voltage, manage current draw, and protect modules such as the neural data acquisition module 238, the analog neural signal to digital converter module 240, the neural data timestamp and packetization module 242, the neural data transmitter module 244, and the accelerometer module 236 against overloads, thus ensuring efficient and safe power distribution to modules or components of the implant device 110.

In some embodiments, the initialization system management module 228 is configured to handle the initialization process when the implant device 110 first starts up, by coordinating the loading and configuration of settings and modules, such as the initialization communication module 230, the system management module 234, and the power management module 226.

In some embodiments, the initialization communication module 230 is configured to set up and prepare the communication channels and protocols needed for the implant device 110 to interact with the wearable device 130 at the beginning of its operation.

In some embodiments, the control layer communication module 232 is configured to manage the flow of data between different modules of the implant device 110 and between the implant device 110 and the wearable device 130.

In some embodiments, the system management module 234 is configured to manage and monitor the performance, health, and operation of the implant device 110. For example, the system management module 234 can track system parameters such as temperature, voltage, and power consumption to ensure stable operation of the implant device 110. In some instances, the system management module 234 can identify system failures, log errors, and provide alerts for troubleshooting.

In some embodiments, the accelerometer module 236 (e.g., hardware accelerator) is specifically designed to significantly speed up the execution of specific tasks by offloading them from the main processor of the ASIC chip 216.

In some embodiments, the neural data acquisition module 238 is configured to record electrical activity from the brain (e.g., neurons) using electrodes 210 of the electrode array 208. In some embodiments, the neural data acquisition module 238 is configured to acquire the electrical activity without performing additional processing on the recorded data. In some embodiments, the neural data acquisition module 238 is configured to boost weak neural signals. In some embodiments, the neural data acquisition module 238 is configured to filter out noise and unwanted frequencies to improve signal quality.

Figure 3A:
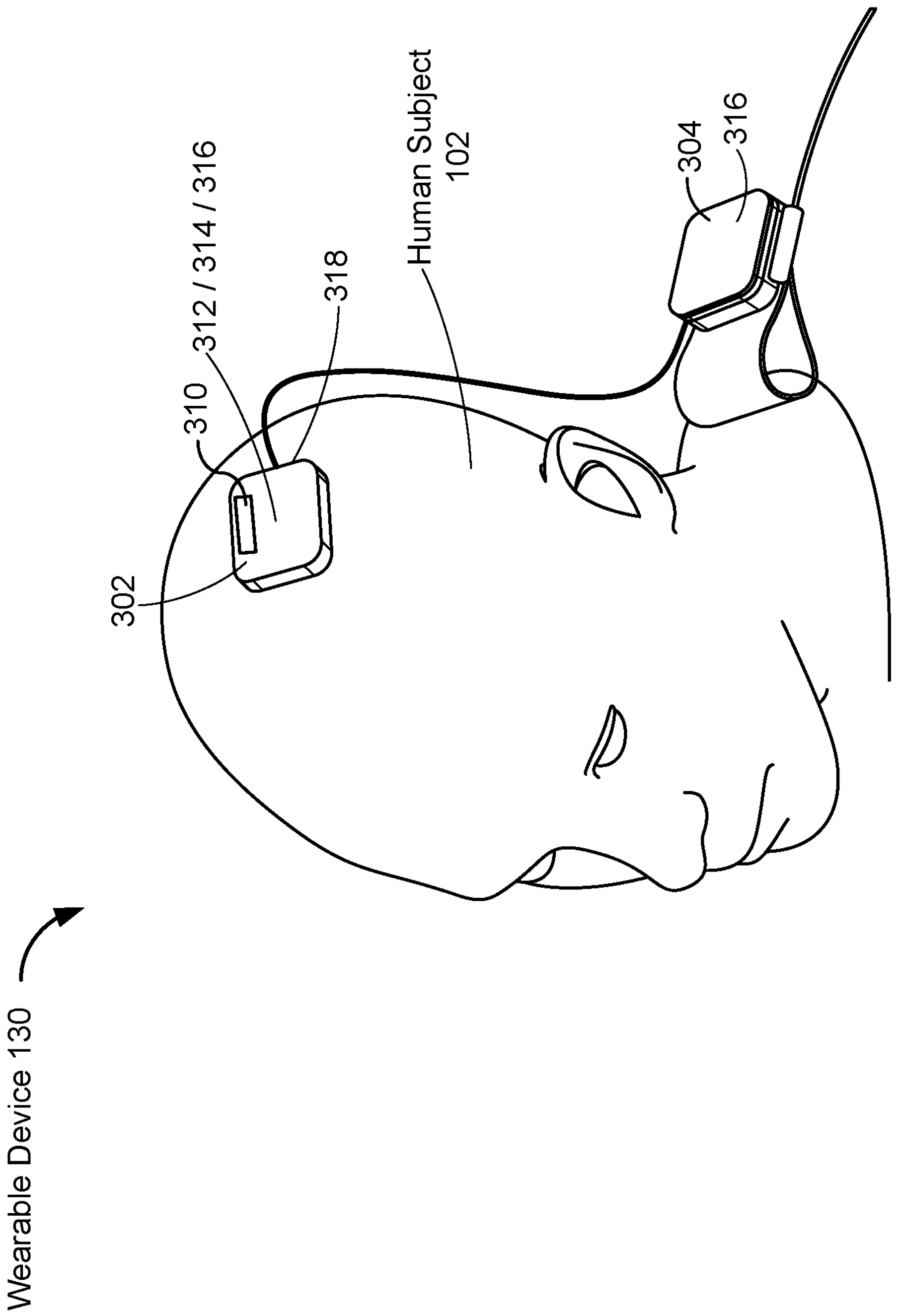
FIG. 3A illustrates an example wearable device, in accordance with some embodiments.

FIG. 3A illustrates a wearable device 130, in accordance with some embodiments. In some embodiments, the wearable device 130 includes a patch component 302, a relay component 304, and wearable electronics 316 (e.g., electronic components).

In some embodiments, the patch component 302 includes one or more magnets 310 that are configured to magnetically couple and align the patch component 302 to the implant device 110. In some embodiments, the patch component 302 includes one or more coils 312 and/or antenna 314 for transmitting power wirelessly into the implant device 110, transmitting command signals into the implant device 110, and/or receiving neural signal data transmitted from the implant device 110. In some embodiments, the patch component 302 includes wearable electronics 316 (e.g., electronic components) (e.g., to power the coils 312 and/or the antennas 314. In some embodiments, the patch component 302 includes a mechanical housing 318 for holding the magnets 310 the coils 312, the antenna 314, and/or the wearable electronics components 316.

In some embodiments, the relay component 304 includes additional electronics for supporting functionalities of the patch component 302, and for enabling data and power transfer between the patch component 302 and the computing device 140. In some embodiments, the relay component 304 is configured to anchor the wearable device 130 on or near the human subject 102, such as on clothing worn by the human subject, or on a wheelchair or mobility device of the human subject, or on a patient bed of the human subject.

Figure 3B:
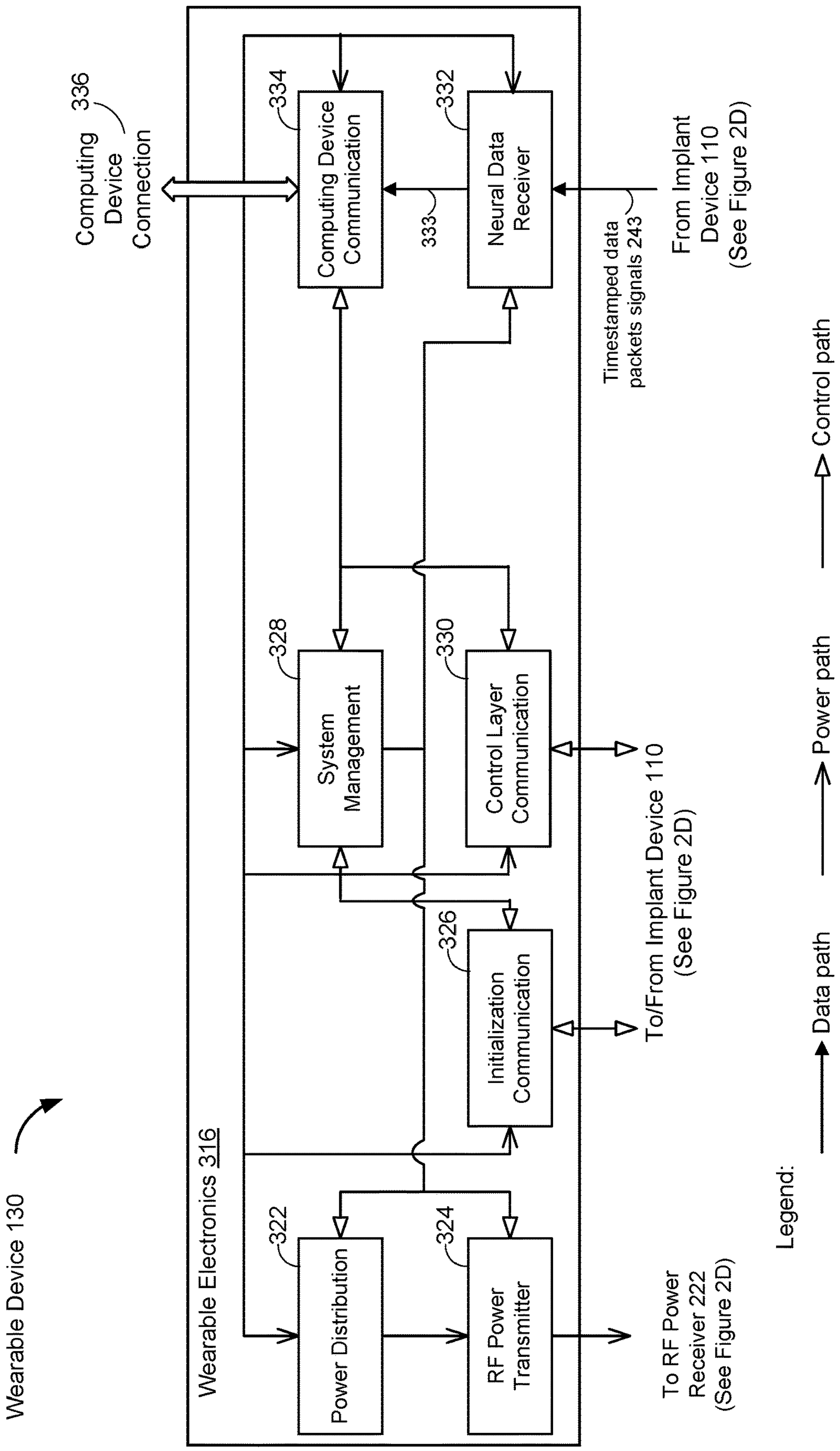
FIG. 3B is a block diagram showing an example data path, control path, and power path of a wearable device, in accordance with some embodiments.

FIG. 3B is a block diagram showing an example data path (represented by closed triangle arrows), power path (represented by two-edged arrows), and control path (represented by open triangle arrows) of a wearable device 130, in accordance with some embodiments.

Data path-wise, in some embodiments, the wearable device 130 includes a neural data receiver module 332 for receiving neural signals in the form of timestamped data packets 243 from the implant device 110. In some embodiments, the neural data receiver module 332 generates packetized combined data 333 by further packetizing the timestamped data packets 243 along with data from the wearable device 130 and control commands. The neural data receiver module 332 transmits the packetized combined data 333 to a computing device communication module 334 that is configured to transmit the packetized combined data 333 to the computing device 140 via a connection 336 of the computing device.

The wearable device 130 is connected to an electrical power source. For example, the wearable device 130 can be connected to an electrical power outlet or can include an energy storage device and/or a battery that is configured to supply power to the wearable device 130. In some embodiments, the wearable device 130 includes a RF transmitter module 324 that is configured to transmit electrical power to the implant device 110 (e.g., to the RF power distribution module 322). Ad depicted in FIG. 3B, the electrical power source of the wearable device 130 is configured to provide power to various modules of the wearable electronics 316, including an initialization communication module 326, a system management module 328, a control layer communication module 330, the neural data receiver module 332, and the computing device communication module 334.

In some embodiments, the initialization communication module 326 is configured to set up and prepare the communication channels and protocols needed for the wearable device 130 to interact with the implant device 110 at the beginning of its operation.

In some embodiments, the system management module 328 is configured to manage and monitor the performance, health, and operation of the wearable device 130. For example, the system management module 328 can track system parameters such as temperature, voltage, and power consumption to ensure stable operation of the wearable device 130. In some instances, the system management module 328 can identify system failures, log errors, and provide alerts for troubleshooting.

In some embodiments, the control layer communication module 330 is configured to manage the flow of data between different modules of the wearable device 130 and between the wearable device 130 and the implant device 110.

Figure 4:
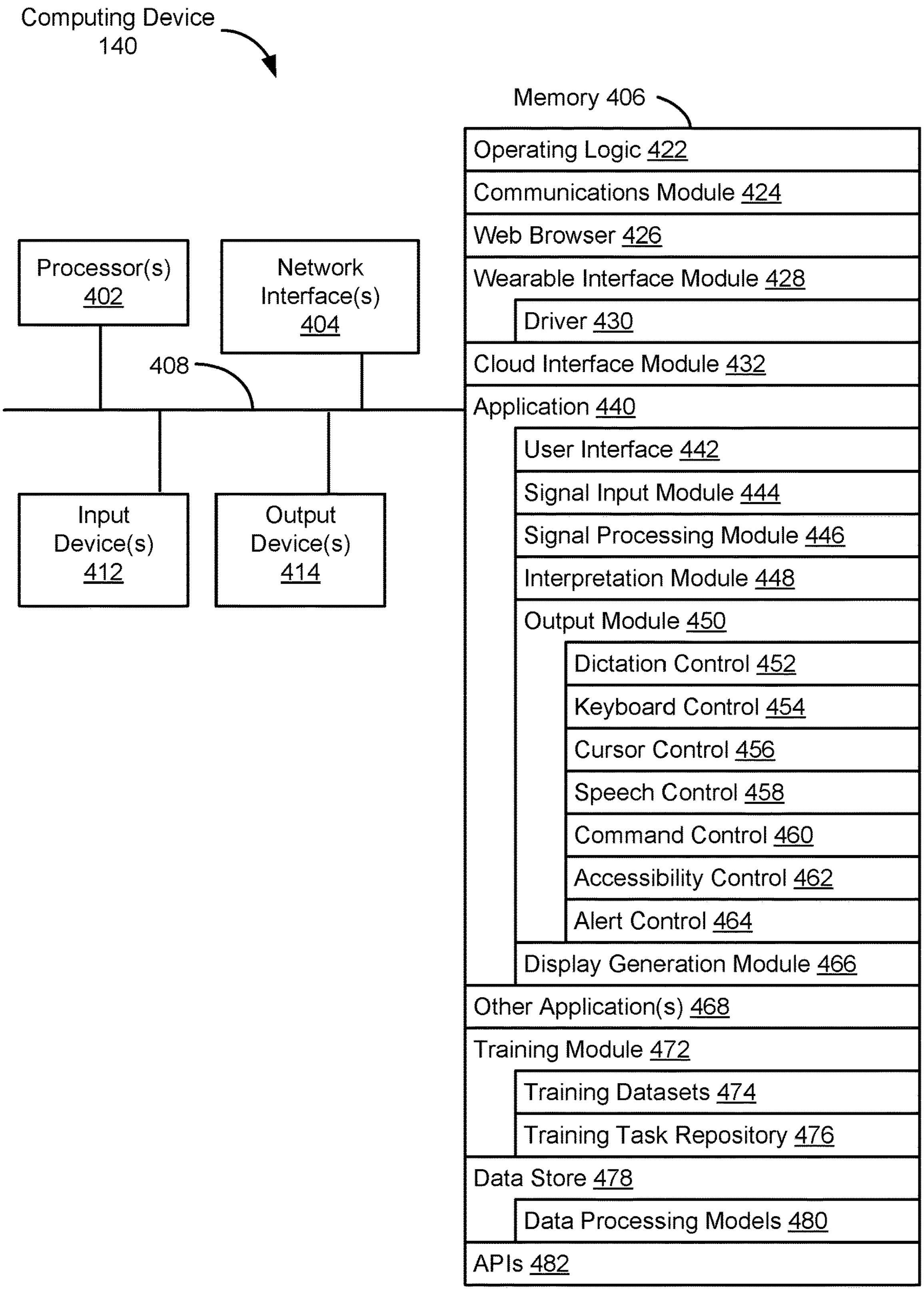
FIG. 4 is a block diagram illustrating an example computing device in accordance with some embodiments.

FIG. 4 is a block diagram illustrating a computing device 140, in accordance with some embodiments. Various examples of the computing device 140 include a desktop computer, a laptop computer, a tablet computer, a virtual reality (VR) device, an augmented reality (AR) device, or a spatial computing device that blends digital content with the physical world. The computing device 140 includes one or more processors 402 (e.g., processing units (CPUs) or cores), one or more network or communication interfaces 404, memory 406, and one or more communication buses 408 for interconnecting these components. In some embodiments, the communication buses 408 include circuitry (sometimes called a chipset) that interconnects and controls communications between system components. In some embodiments, the computing device 140 includes a user interface 410. The user interface 410 typically includes a display (e.g., display device) 412.

In some embodiments, the computing device 140 includes one or more input devices 412, which facilitate user input, such as a keyboard, a mouse, a voice-command input unit or microphone, a display 170 (e.g., which can be a touch-sensitive display), a touch-sensitive input pad, a gesture capturing camera, or other input buttons or controls. In some embodiments, the computing device 140 uses a microphone and voice recognition or a camera and gesture recognition to supplement or replace the keyboard. In some implementations, the computing device 140 includes one or more cameras, scanners, or photo sensor units for capturing images. In some embodiments, the computing device 140 includes one or more output devices 414, which enable presentation of user interfaces and display content, including one or more speakers and/or one or more visual displays.

The memory 406 includes high-speed random-access memory, such as DRAM, SRAM, DDR RAM, or other random-access solid-state memory devices. In some embodiments, the memory 20406 6 includes non-volatile memory, such as one or more magnetic disk storage devices, one or more optical disk storage devices, one or more flash memory devices, or one or more other non-volatile solid state storage devices. In some embodiments, the memory 406 includes one or more storage devices remotely located from the processors 402. The memory 406, or alternatively the non-volatile memory devices within the memory 406, includes a non-transitory computer-readable storage medium. In some embodiments, the memory 406, or the computer-readable storage medium of the memory 406, stores the following programs, modules, and data structures, or a subset or superset thereof:

- an operating system 422, which includes procedures for handling various basic system services and for performing hardware dependent tasks;
- a communications module 424, which connects the computing device 140 to other devices (e.g., various servers in the server system 160, implant device 110, wearable device 130, external display device 173, and mouse 174) via one or more network interfaces 404 (wired or wireless) and one or more networks 150, such as the Internet, other wide area networks, local area networks, metropolitan area networks, and so on;
- a web browser 426 (or other application capable of displaying web pages), which enables a user to communicate over a network with remote computers or devices;
- a wearable interface module 428, for interfacing with various modules and components of the wearable device 130. In some embodiments, the wearable interface module 428 includes:
  - a driver 430, which provides two-way telemetry between the computing device and the wearable device 130 and data input for application 440;
- a cloud interface module 432, for providing two-way communication between the computing device 140 and the server system 160;
- an application 440. In some embodiments, the application 440 includes:
  - a user interface 442 for providing visual information to users and for capturing user inputs;
  - a signal input module 444 for receiving brain signals (e.g., electrical signals or data streams) of a human subject 102. As discussed with reference to FIGS. 1, 2, and 3, in some embodiments, the brain signals are collected by implant device 110 and transmitted to the wearable device 130. In some embodiments, the brain signals include attempted or intended speech signals (e.g., the human subject 102 tries to speak, thereby producing electrical signals corresponding to the intended movement of specific individual muscles or groups of muscles used for speech articulation, but their speech may not be vocalized due to underlying pathology preventing correct movement of the intended muscles or muscle groups). In some embodiments, the brain signals include attempted non-speech motor signals, such as attempted head, arm, hand, foot or leg movement signals (e.g., the human subject 102 tries to move their head or limbs, thereby producing electrical signals corresponding to the intended movement of specific individual muscles or groups of muscles used for the desired movement, but actual, physical movement may or may not occur due to underlying pathology preventing correct movement of the intended muscle or muscle groups) and attempted gestures (e.g. a hand squeeze or gesture);
  - a signal processing module 446 for decoding the brain signals, including extracting electrophysiological features from the brain signals and performing signal processing functions. The extracted features represent brain activities intended for desired actions. In some embodiments, the signal processing module 446 analyzes signal characteristics such as amplitude, latency of event-evoked potentials, frequency power spectra (e.g., sensorimotor rhythms), or neuronal firing rates, in time-domain and/or frequency-domain. In some embodiments, the signal processing module 446 applies mathematical operations to enhance, filter, or modify the signals, allowing for better interpretation and utilization of the data;

an interpretation module 448 (e.g., decoding module) for decoding the brain signals by recognizing patterns of the extracted features and the intended actions they represent. In some embodiments, the interpretation module 448 implements a classification process to recognize patterns in the extracted features. In some embodiments, the interpretation module 448 applies one or more machine learning models (e.g., data processing models 480 and/or data processing models 568) to decode the brain signals and determine intended actions of the human subject 102. In some embodiments, the interpretation module 448 applies a machine learning algorithm to decode the brain signals and determine intended actions of the human subject 102. In some embodiments, the machine learning algorithm is associated with the one or more machine learning models. In some embodiments, the interpretation module 448 is configured to generate a respective distinct set of intended actions depending on the operating mode (e.g., operating modes 190) of the computing device. In some embodiments, the interpretation module 448 is configured to translate and/or transform the classified features into actual commands;

an output module 450 for controlling one or more devices, applications, and/or application interfaces to execute the one or more intended actions. In some embodiments, the output module 450 is configured to control the one or more devices, applications, and/or application interfaces to perform dictation control 452, keyboard control 454, cursor control 456, speech control 458, command control 460, accessibility control 462, and alert control 464. In some embodiments, the output module 450 is configured to control an external robotic arm. In some embodiments, the output module 450 is configured to control a prosthetic limb of the human subject 102; and a display generation module 466 for generating visual outputs for display on a display device such as a display screen 170 of the computing device 140 of an external display device 173;

one or more other applications 468 that are executed on the computing device 140, Exemplary applications can include a messaging application, an email application, a data presentation and communication application;

a training module 472 for performing limited machine learning model training. In some embodiments, the server system 160 is configured to train one or more machine learning models (e.g., decoding models) that are deployed locally on the computing device 140. In some embodiments, limited model training occurs locally on the computing device 140. In some embodiments, the training module 472 includes:

one or more training datasets 474; and a training task repository 476, which includes training activities or tasks for training the models one or more data processing models 480.

a data store 478 for storing data associated with the computing device 140, including:

one or more data processing models 480 (e.g., machine learning models, machine learning algorithms, decoding models, and/or decoding algorithms) for supporting the functions performed by the signal processing module 446 and/or the interpretation module 448. As used herein, a data processing model 480 can refer a machine learning model or an algorithm; and APIs 482 for receiving API calls from one or more applications (e.g., a web browser 426, application 440, other applications 468), translating the API calls into appropriate actions, and performing one or more actions.

Each of the above identified executable modules, applications, or sets of procedures may be stored in one or more of the previously mentioned memory devices, and corresponds to a set of instructions for performing a function described above. The above identified modules or programs (i.e., sets of instructions) need not be implemented as separate software programs, procedures, or modules, and thus various subsets of these modules may be combined or otherwise re-arranged in various embodiments. In some embodiments, the memory 406 stores a subset of the modules and data structures identified above. Furthermore, the memory 406 may store additional modules or data structures not described above. In some embodiments, a subset of the programs, modules, and/or data stored in the memory 406 is stored on and/or executed by a server system 160.

Although FIG. 4 shows a computing device 140, FIG. 4 is intended more as a functional description of the various features that may be present rather than as a structural schematic of the embodiments described herein. In practice, and as recognized by those of ordinary skill in the art, items shown separately could be combined and some items could be separated. In addition, some of the programs, functions, procedures, or data shown above with respect to the computing device 140 may be stored or executed on a server system 160.

Figure 5:
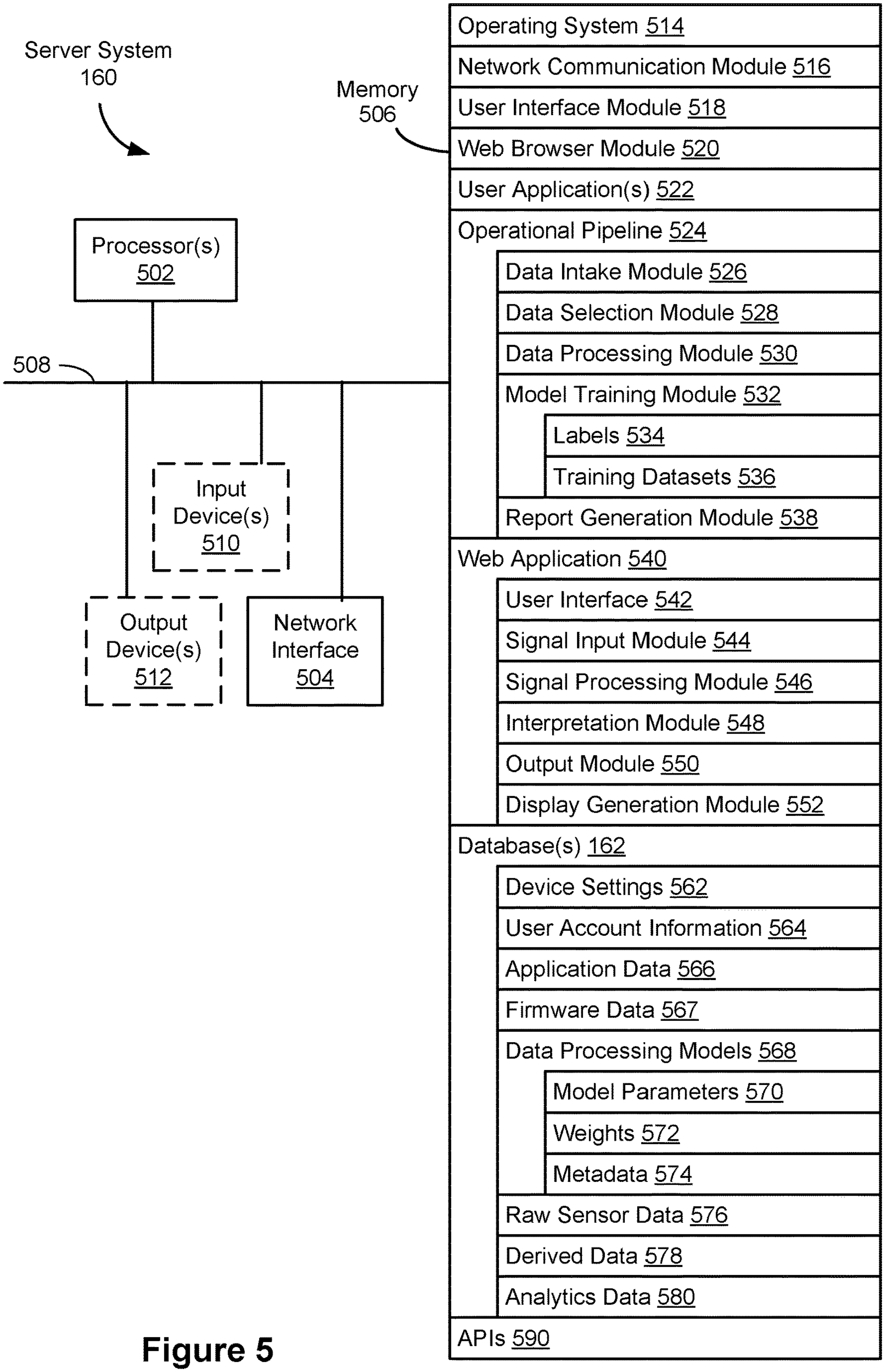
FIG. 5 is a block diagram illustrating an example server system in accordance with some embodiments.

FIG. 5 is a block diagram of a server system 160, in accordance with some embodiments. The server system 160 typically includes one or more processors 502 (e.g., processing units or cores (CPUs)), one or more network interfaces 504, memory 506, and one or more communication buses 508 for interconnecting these components (sometimes called a chipset). In some embodiments, the server system 160 includes one or more input devices 510, which facilitate user input, such as a keyboard, a mouse, a voice-command input unit or microphone, a touch screen display, a touch-sensitive input pad, a gesture capturing camera, or other input buttons or controls. In some embodiments, the server system 160 uses a microphone and voice recognition or a camera and gesture recognition to supplement or replace the keyboard. In some implementations, the server system 160 includes one or more cameras, scanners, or photo sensor units for capturing images. In some implementations, the server system 160 includes one or more output devices 512, which enable presentation of user interfaces and display content, including one or more speakers and/or one or more visual displays.

The memory 506 includes high-speed random access memory, such as DRAM, SRAM, DDR RAM, or other random access solid state memory devices. In some implementations, the memory 506 includes non-volatile memory, such as one or more magnetic disk storage devices, one or more optical disk storage devices, one or more flash memory devices, or one or more other non-volatile solid state storage devices. In some implementations, the memory 506 includes one or more storage devices remotely located from the processing units 502. The memory 506, or alternatively the non-volatile memory within the memory 506, includes a non-transitory computer readable storage medium. In some implementations, the memory 506, or the non-transitory computer readable storage medium of the memory 506, stores the following programs, modules, and data structures, or a subset or superset thereof:

- an operating system 514, which includes procedures for handling various basic system services and for performing hardware dependent tasks;
- a network communication module 516, which connects the server system 160 to other devices (e.g., various servers in the server system 160, computing device 140, a client device, or other devices) via one or more network interfaces 504 (wired or wireless) and one or more networks 150, such as the Internet, other wide area networks, local area networks, metropolitan area networks, and so on;
- a user interface module 518, which enables presentation of information (e.g., a graphical user interface for presenting applications, widgets, websites and web pages thereof, and/or games, audio and/or video content) at a computing device 140 or electronic device 178;
- a web browser module 520 for navigating, requesting (e.g., via HTTP), and displaying websites and web pages thereof, including a web interface for logging into a user account associated with a computing device 140 or another electronic device, controlling the computing device or electronic device if associated with the user account, and editing and reviewing settings and data that are associated with the user account;
- an operational pipeline 524, including:
  - a data intake module 526 for obtaining respective neural signals that are collected by respective implant devices;
  - a data selection module 528 for automatically choosing the most relevant and suitable data subsets from a larger data pool (e.g., form the one or more databases 162);
  - a data processing module 538 for transforming raw sensor data 576 through various processing steps such as data cleaning, normalization, and feature extraction. In some embodiments, the data processing module 538 generates training data for use by a model training module 532 by preparing the processed data in a suitable format;
  - the model training module 532 for receiving the training data and establishing one or more data processing models 568 for processing neural data collected by implant devices 110. In some embodiments, the model training module 532 includes labels 534 for training the data processing models 568. In some embodiments, the model training module 532 includes training datasets 536 for training the data processing models 568;
- a web application 540, which may be downloaded and executed by a web browser 426 on a user's computing device 140. In general, a web application 540 has the same functionality as application 440, but provides the flexibility of access from any device at any location with network connectivity, and does not require installation and maintenance. In some embodiments, the web application 540 includes various software modules to perform certain tasks, such as:
  - a user interface 542, which provides the user interface for all aspects of the web application 540;
  - a signal input module 544, which has the same functionalities as signal input module 444
  - a signal processing module 546, which has the same functionalities as signal processing module 446;
  - an interpretation module 548, which has the same functionalities as interpretation module 448;
  - an output module 550, which has the same functionalities as output module 450; and
  - a display generation module 552, which has the same functionalities as display generation module 466;
- one or more databases 162 for storing at least data including one or more of:
  - device settings 562 including common device settings (e.g., service tier, device model, storage capacity, processing capabilities, communication capabilities, etc.) of the one or more server systems 160, computing devices 140, or other devices;
  - user account information 564 for the application 440 and/or the web application 540, such as user names, security questions, account history data, user preferences, and predefined account settings
  - application data 566 from the application 540, web application 540, and/or the user applications
  - firmware data 567 corresponding to respective firmware versions;
  - data processing models 568 (e.g., machine learning models, machine learning algorithms, decoding models, and/or decoding algorithms) for decoding neural signal data into intended user actions. In some embodiments, the data processing models 568 include model parameters 570, weights 572, and metadata 574
  - raw sensor data 576 acquired by one or more electrode arrays 208;
  - derived data 578 obtained by transforming, processing, or analyzing the raw sensor data 576; and
  - analytics data 580, which are data that are collected, processed, and analyzed from the raw sensor data 576 and the derived data 578 to gain insights and identify patterns; and
- APIs 590 for receiving API calls from one or more applications (e.g., web browser module 520, user applications 522, and web application 540) and the one or more data processing models 568, translating the API calls into appropriate actions, and performing one or more actions.

Each of the above identified executable modules, applications, or sets of procedures may be stored in one or more of the previously mentioned memory devices, and corresponds to a set of instructions for performing a function described above. The above identified modules or programs (i.e., sets of instructions) need not be implemented as separate software programs, procedures, or modules, and thus various subsets of these modules may be combined or otherwise re-arranged in various embodiments. In some embodiments, the memory 506 stores a subset of the modules and data structures identified above. Furthermore, the memory 506 may store additional modules or data structures not described above.

Although FIG. 5 shows a server system 160, FIG. 5 is intended more as a functional description of the various features that may be present rather than as a structural schematic of the embodiments described herein. In practice, and as recognized by those of ordinary skill in the art, items shown separately could be combined and some items could be separated. In addition, some of the programs, functions, procedures, or data shown above with respect to a server system 160 may be stored or executed on a computing device 140. In some embodiments, the functionality and/or data may be allocated between a computing device 140 and one or more server systems 160. Furthermore, one of skill in the art recognizes that FIG. 5 need not represent a single physical device. In some embodiments, the server functionality is allocated across multiple physical devices in a server system. As used herein, references to a "server" include various groups, collections, or arrays of servers that provide the described functionality, and the physical servers need not be physically colocated (e.g., the individual physical devices could be spread throughout the United States or throughout the world).

Devices, Methods, and Graphical User Interfaces for Improving Text Content Generated Based on Decoded Brain Signals Attention is now directed towards embodiments of user interfaces ("UI") and associated processes that may be implemented on an electronic device (or computer system more generally), such as computing device 140, with a display, (optionally) a touch-sensitive surface, and one or more inputs devices, including wearable device 130.

Figure 6A:
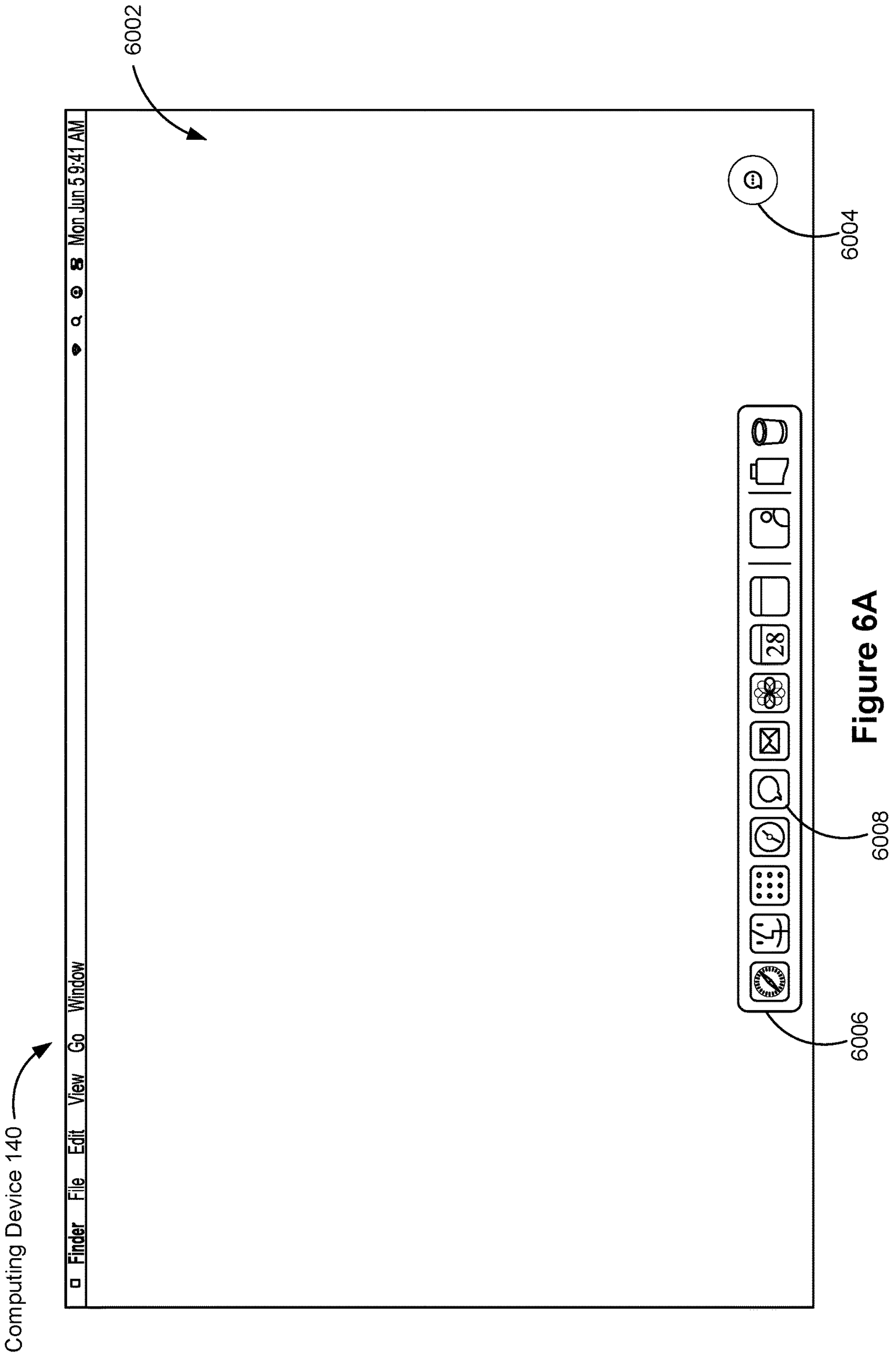
FIGS. 6A to 6H illustrate example user interface for previewing neural text output in a system user interface, in accordance with some embodiments.
Figure 6B:
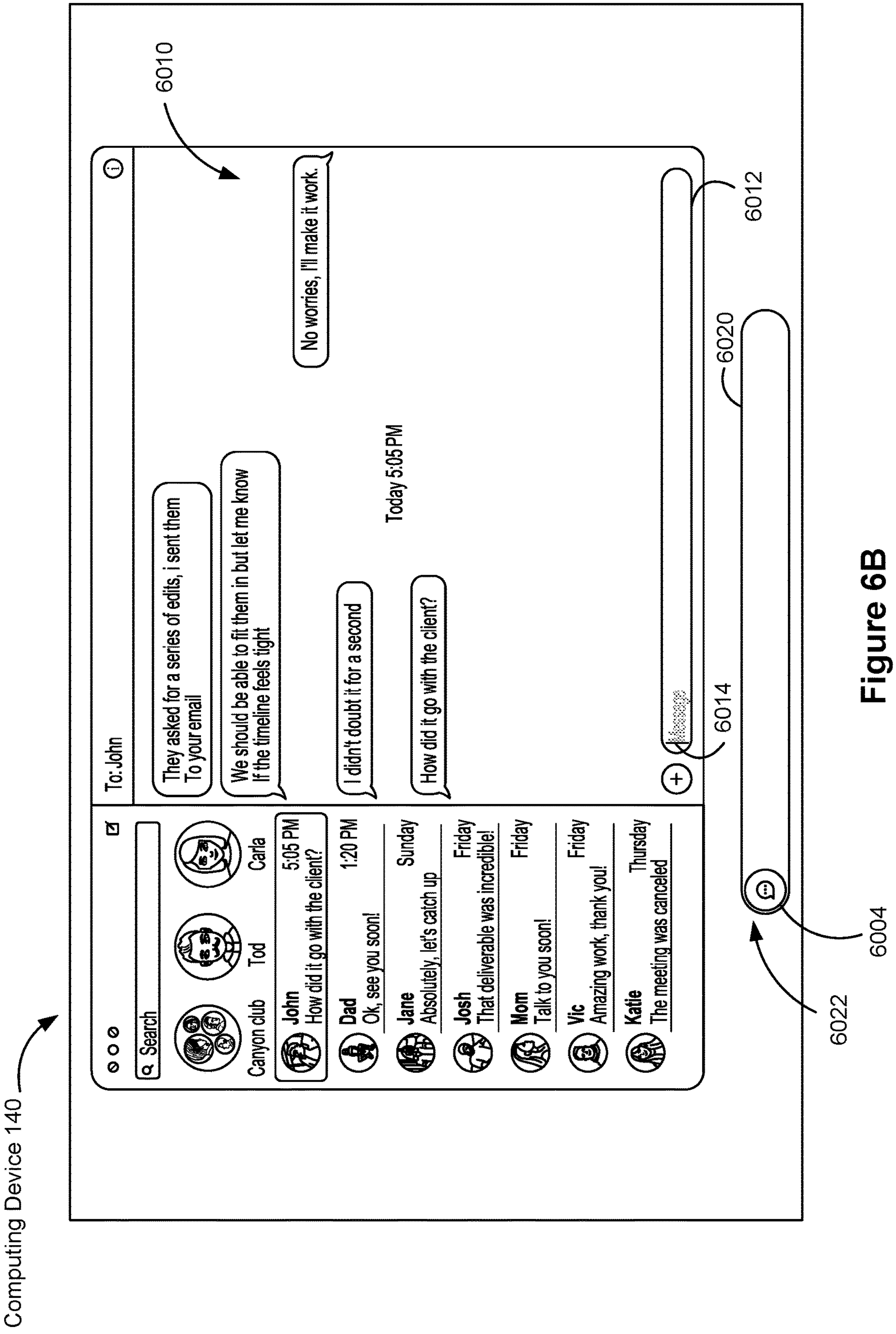
Figure 6C:
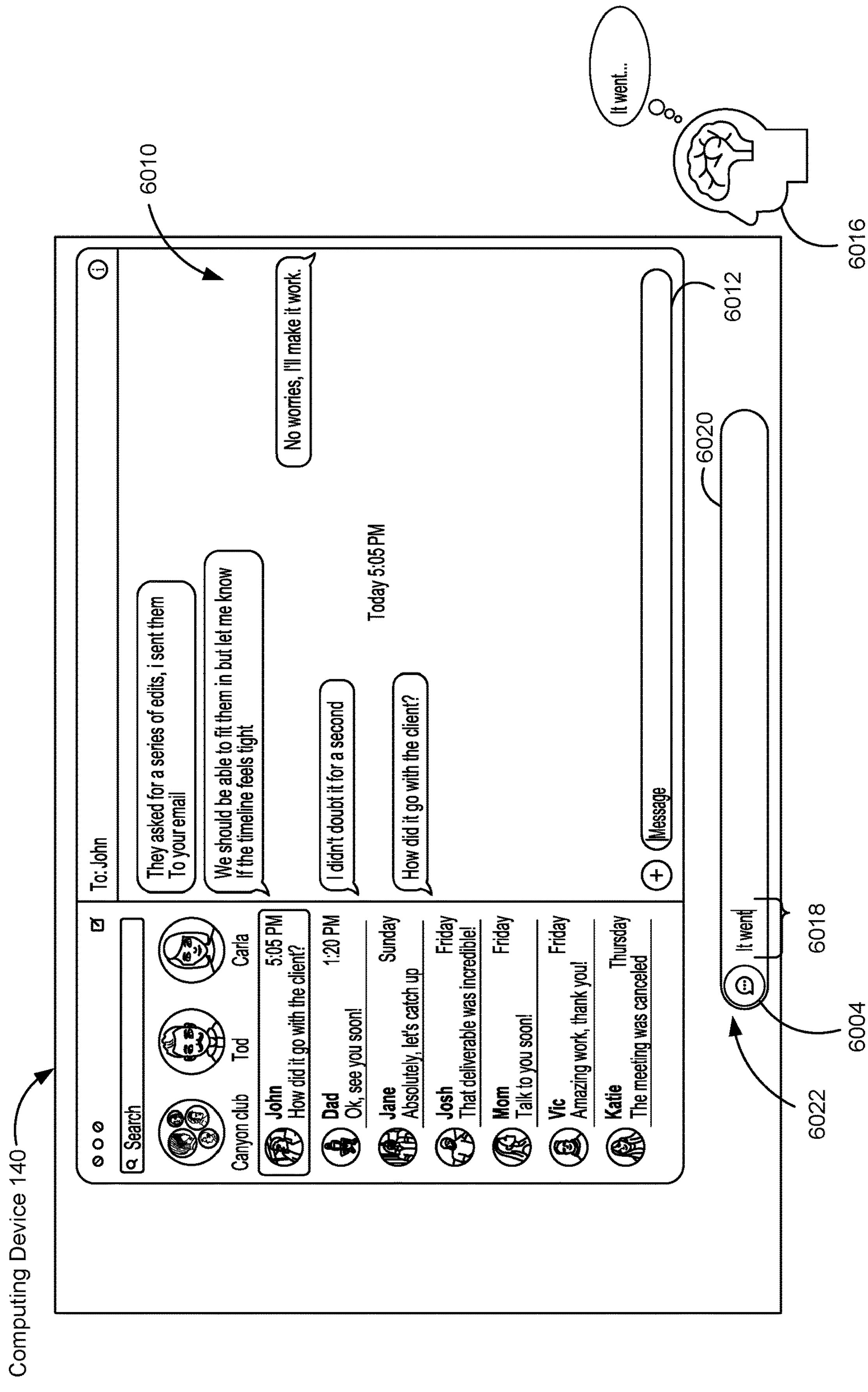
Figure 6D:
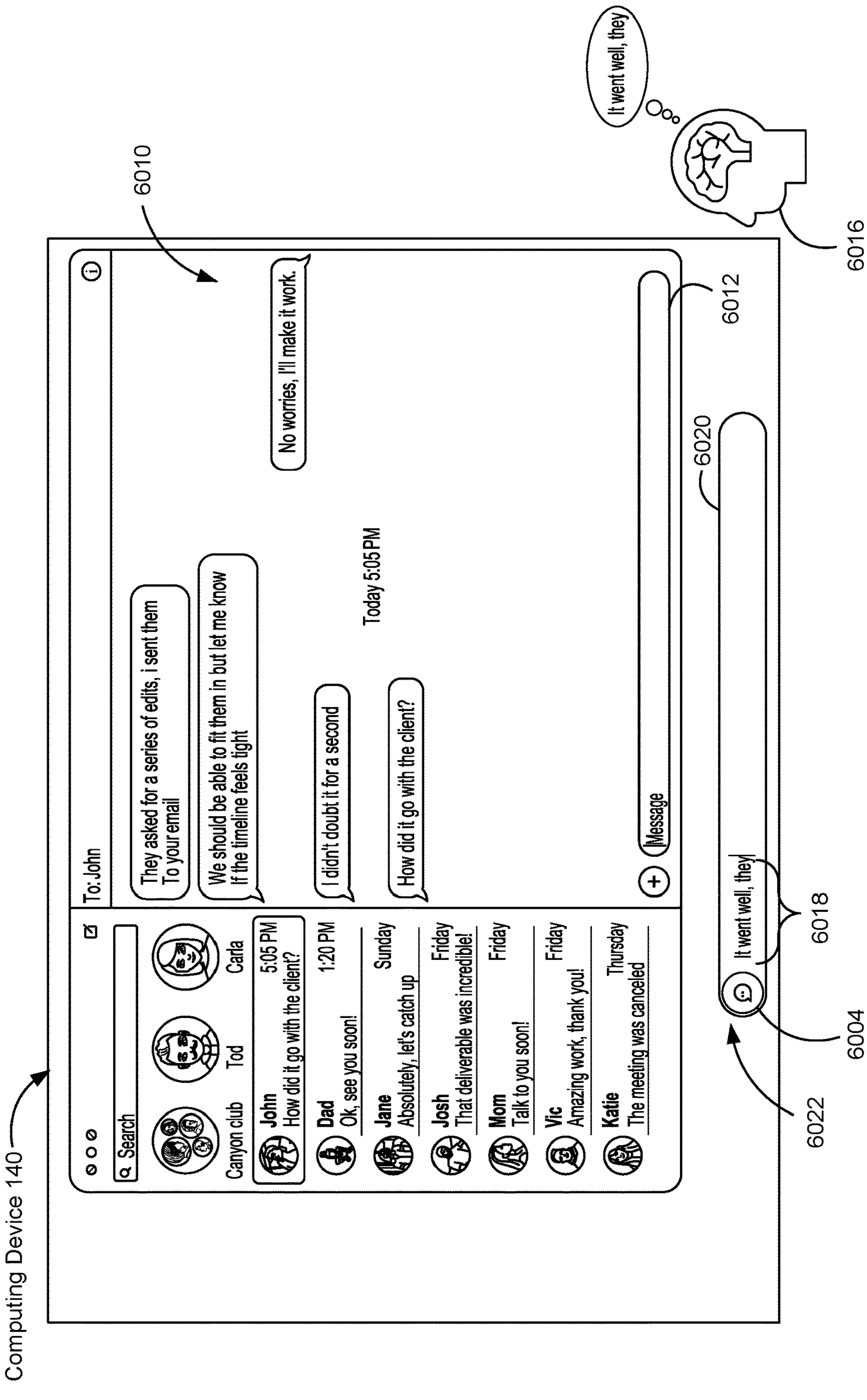
Figure 6E:
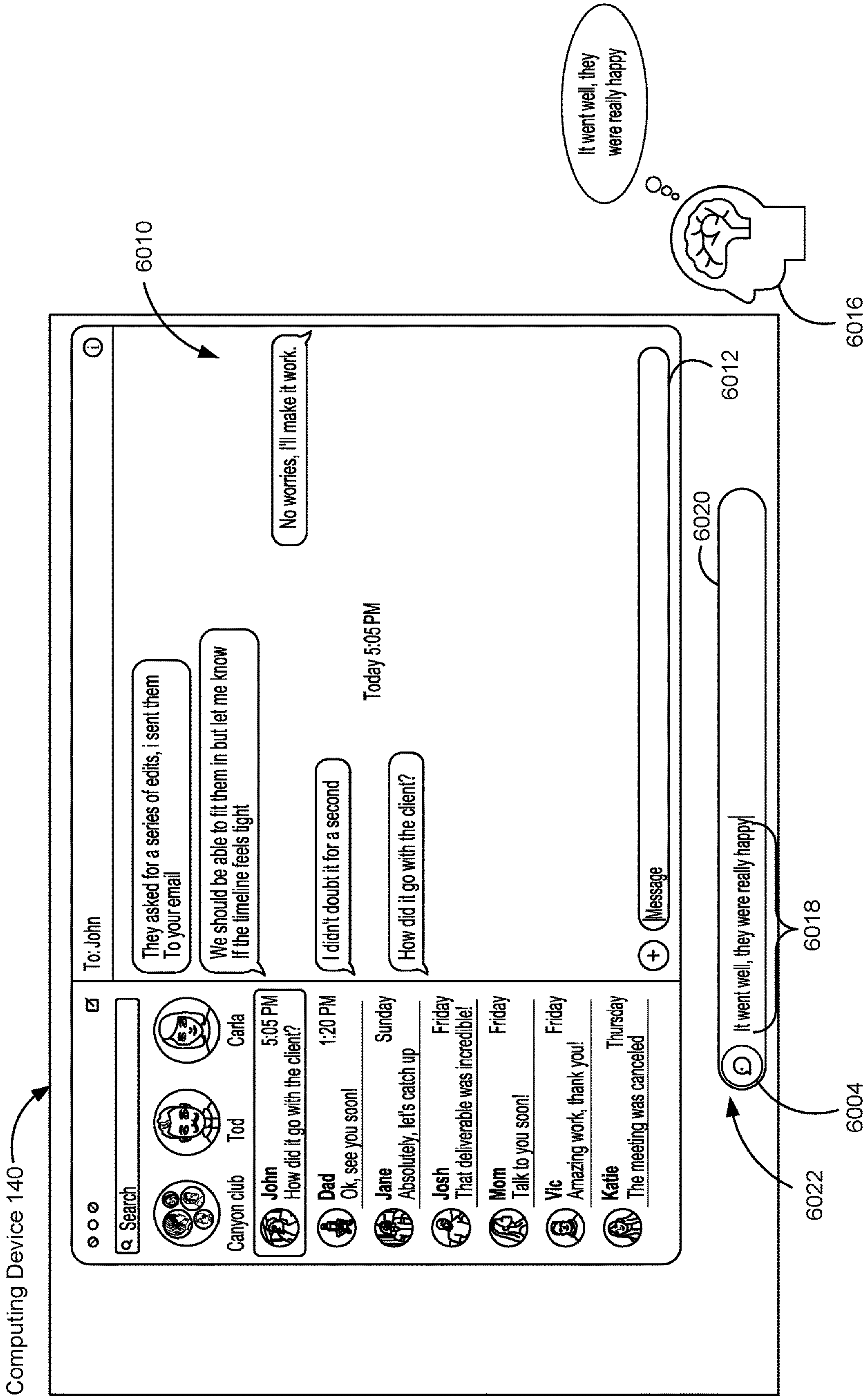
Figure 6F:
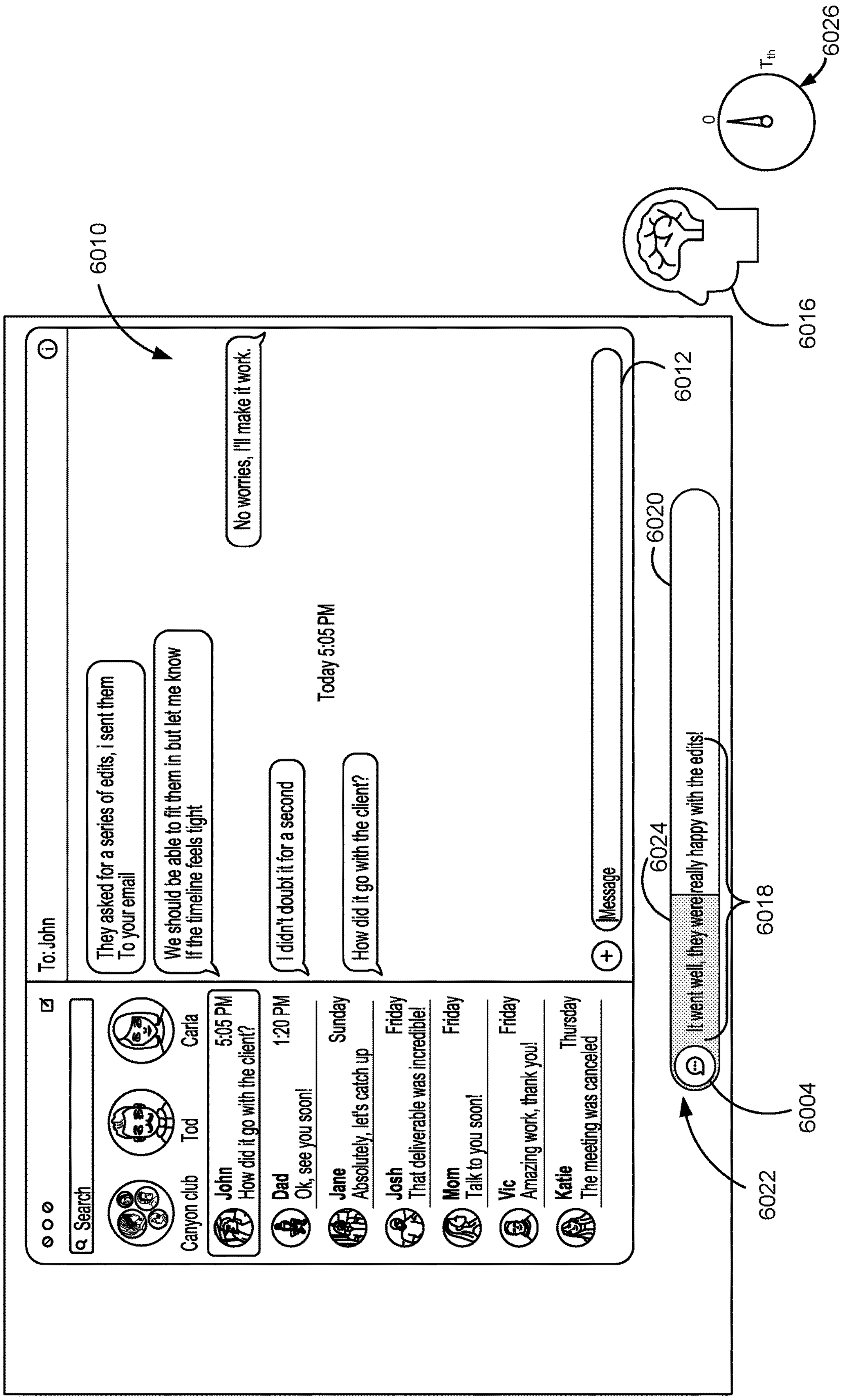
Figure 6G:
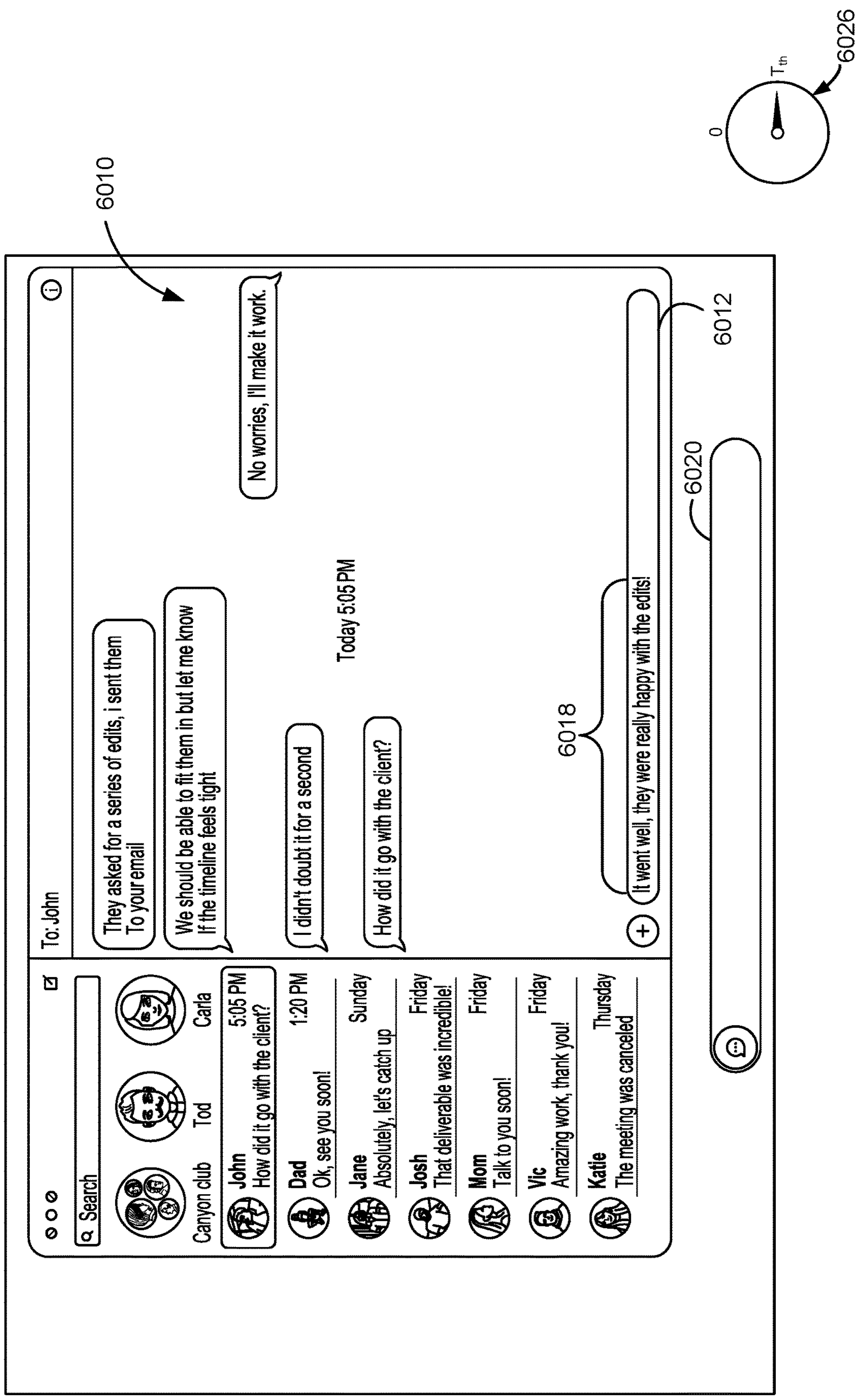
Figure 6H:
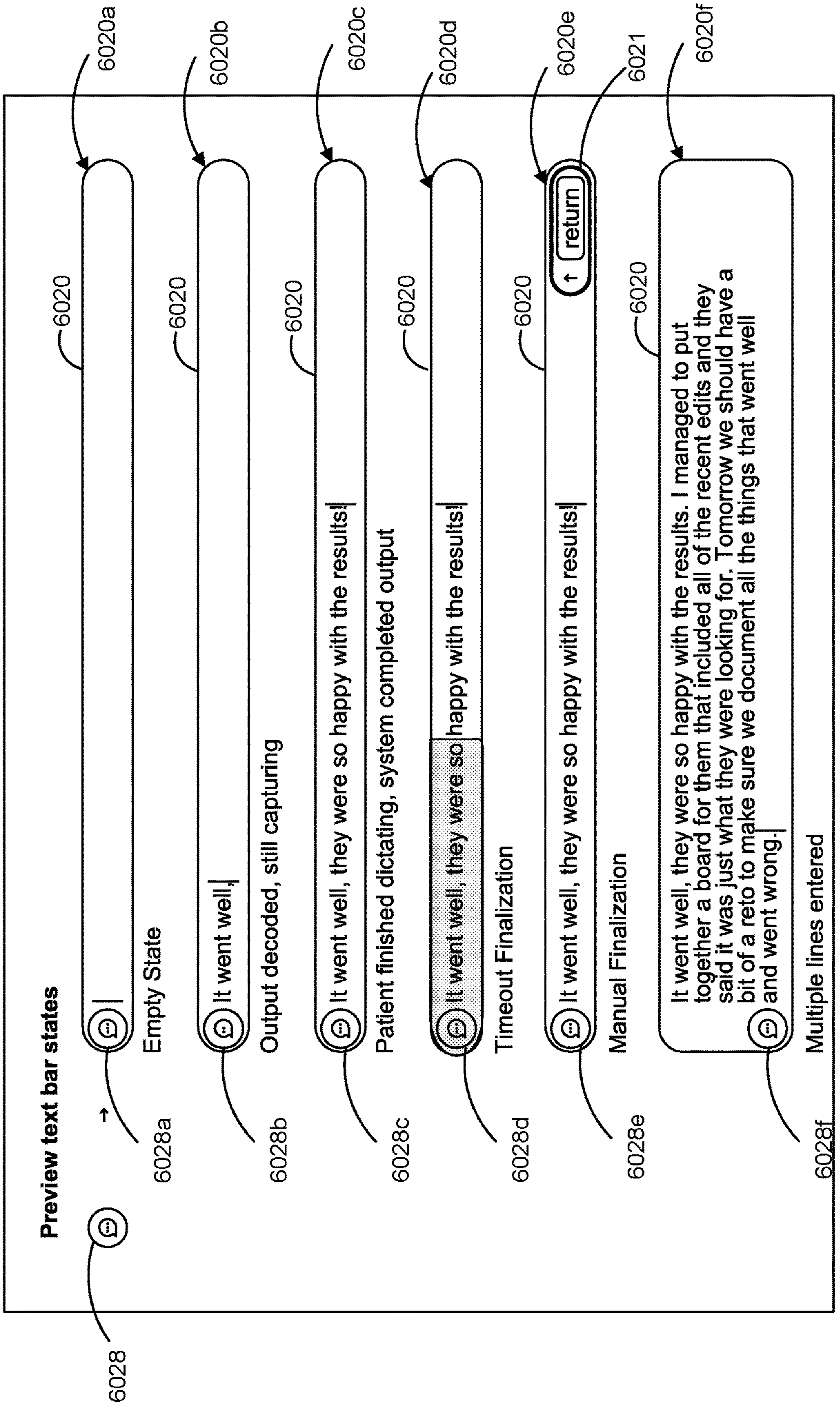
Figure 6I:
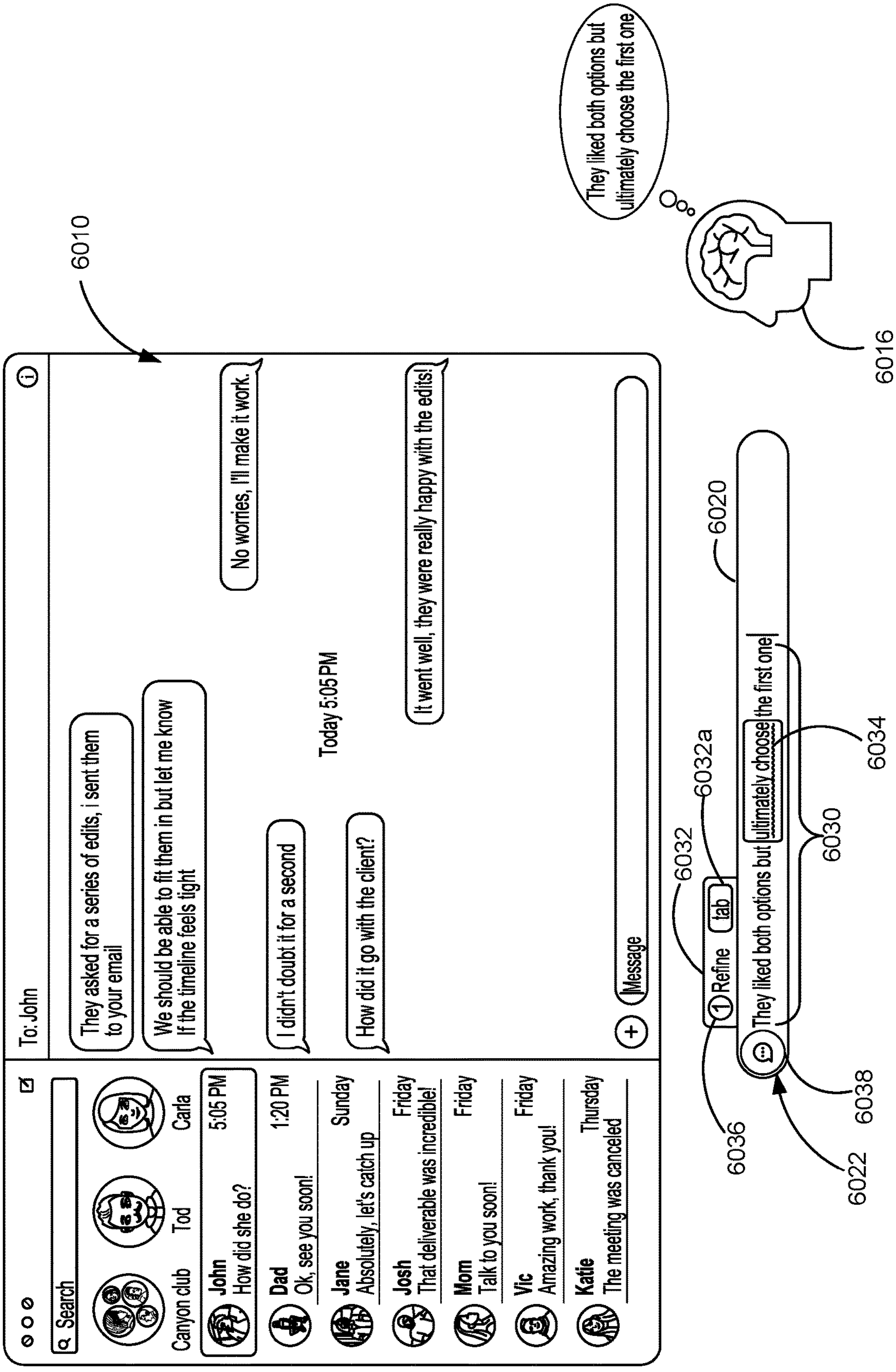
FIGS. 6I to 6K illustrate a system user interface for revising neural text output, in accordance with some embodiments.
Figure 6J:
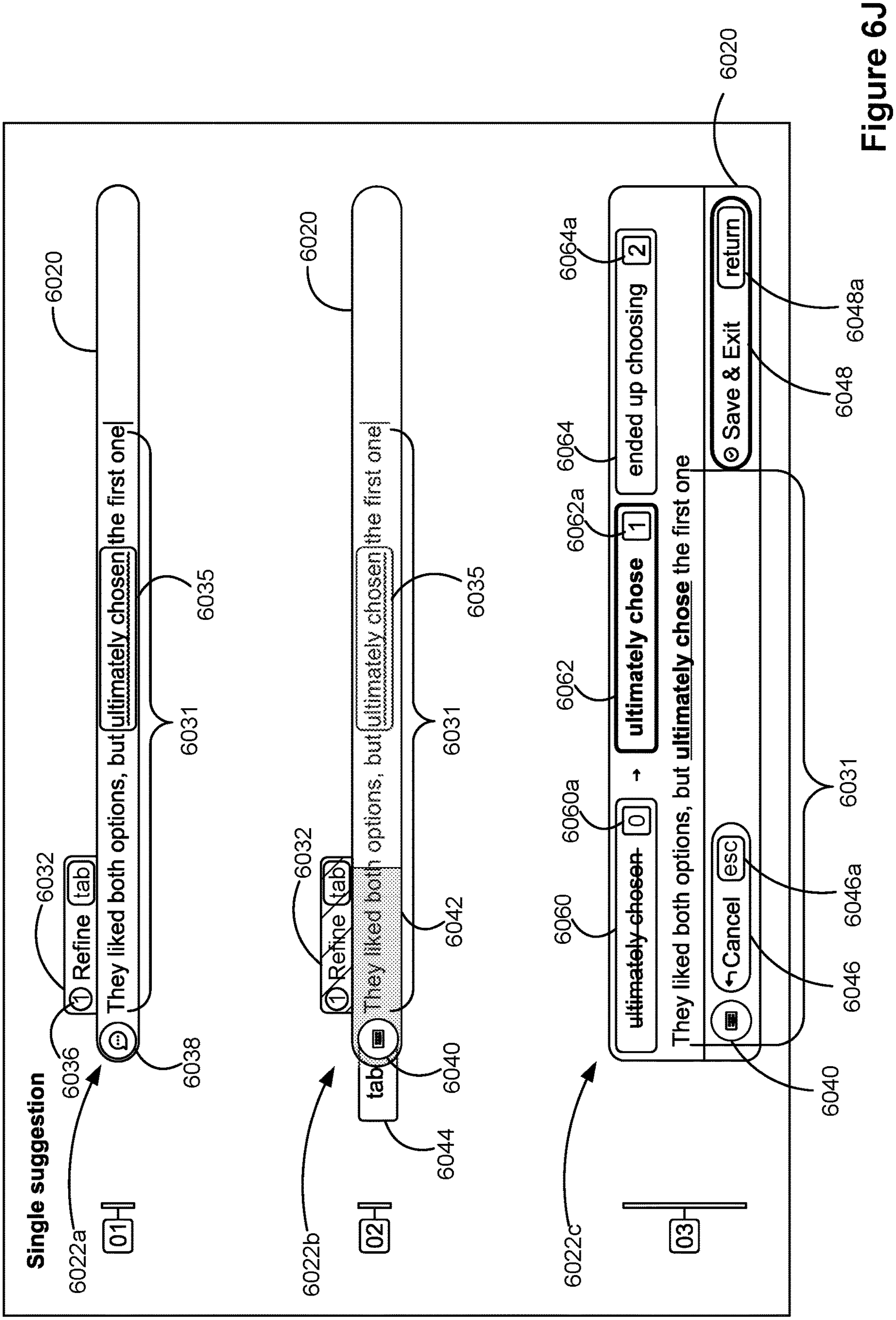
Figure 6K:
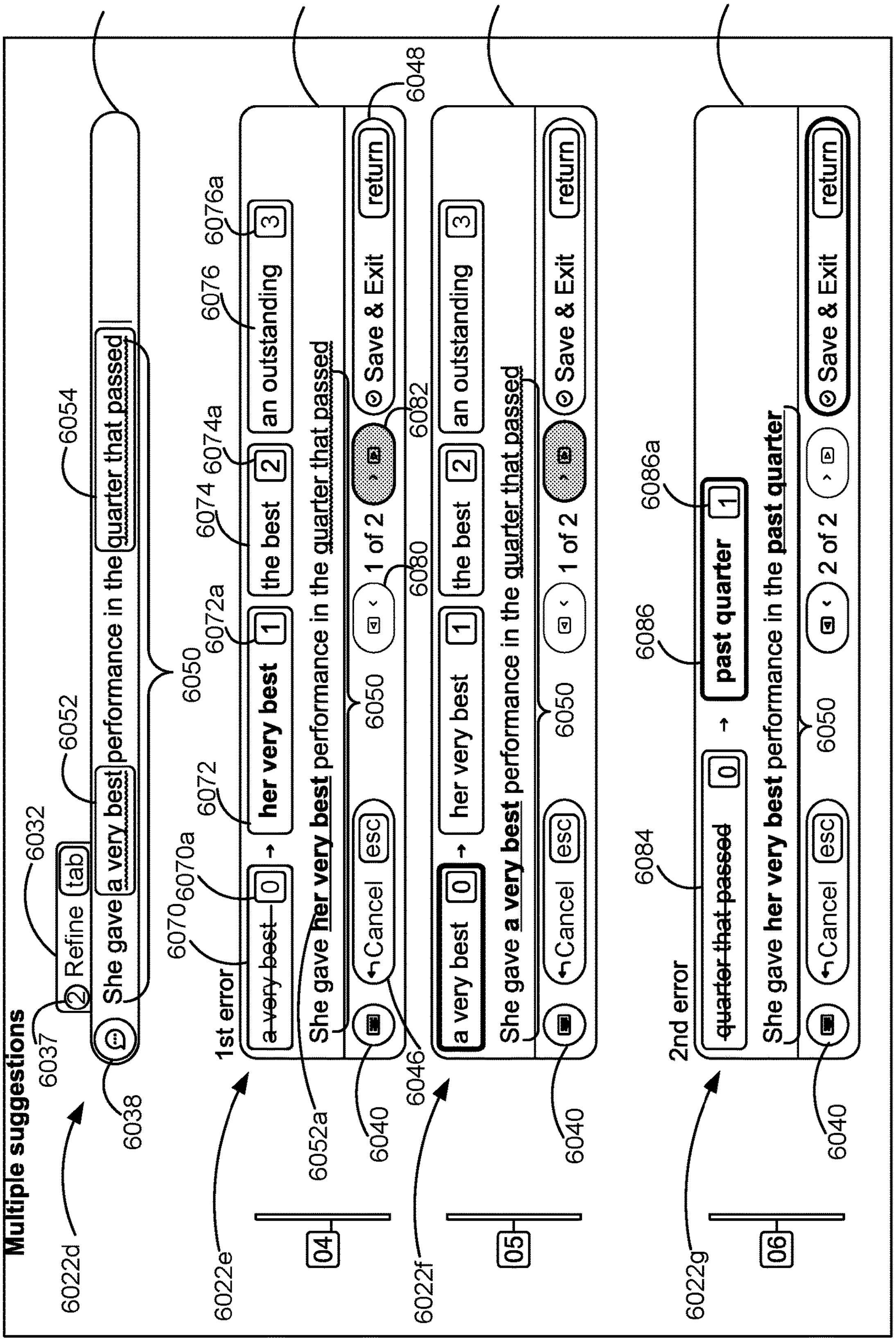
Figure 6L:
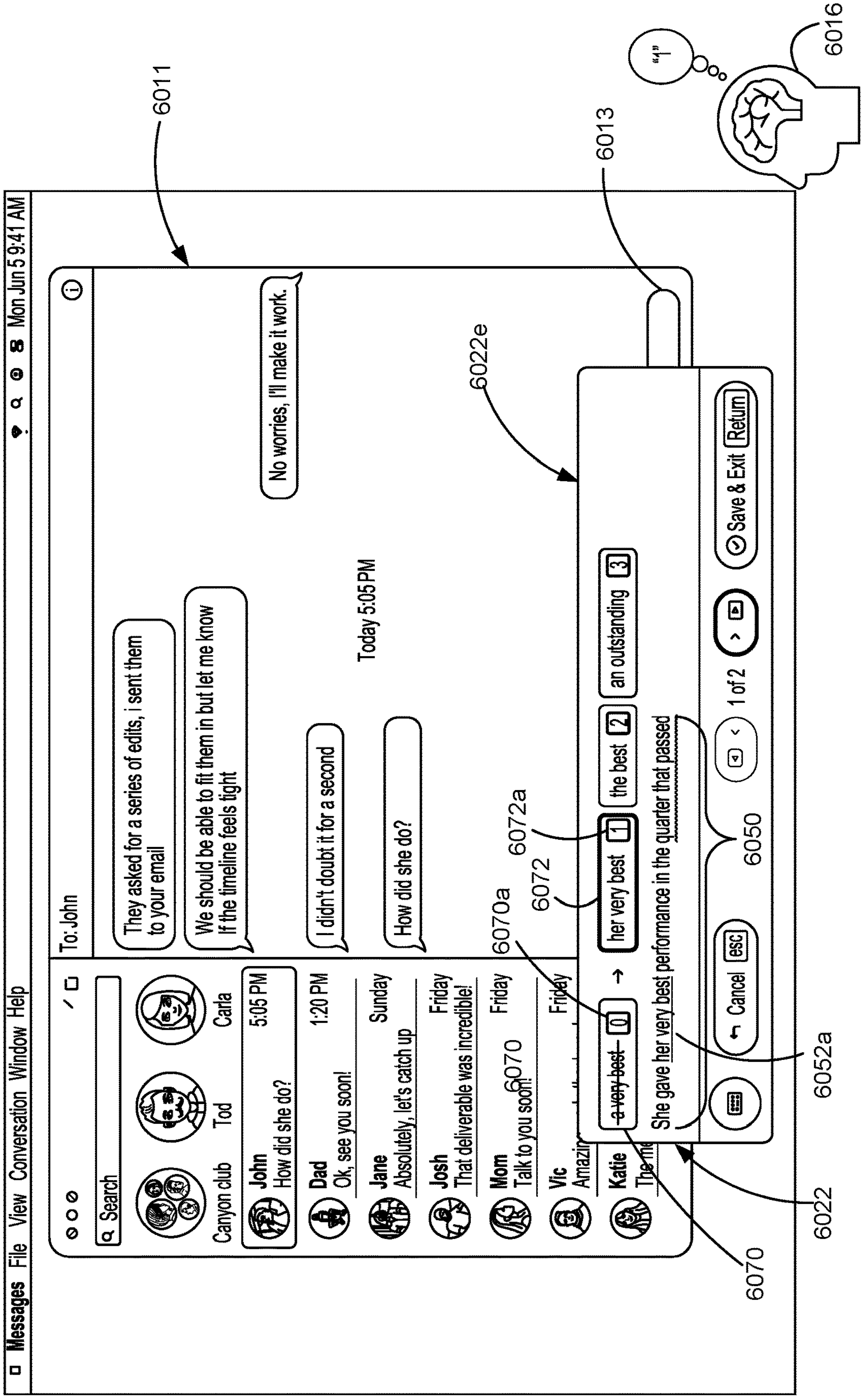
FIGS. 6L to 6P illustrate user interaction with the system user interface for revising neural text output after the process for revising neural text output has been initiated, in accordance with some embodiments.
Figure 6M:
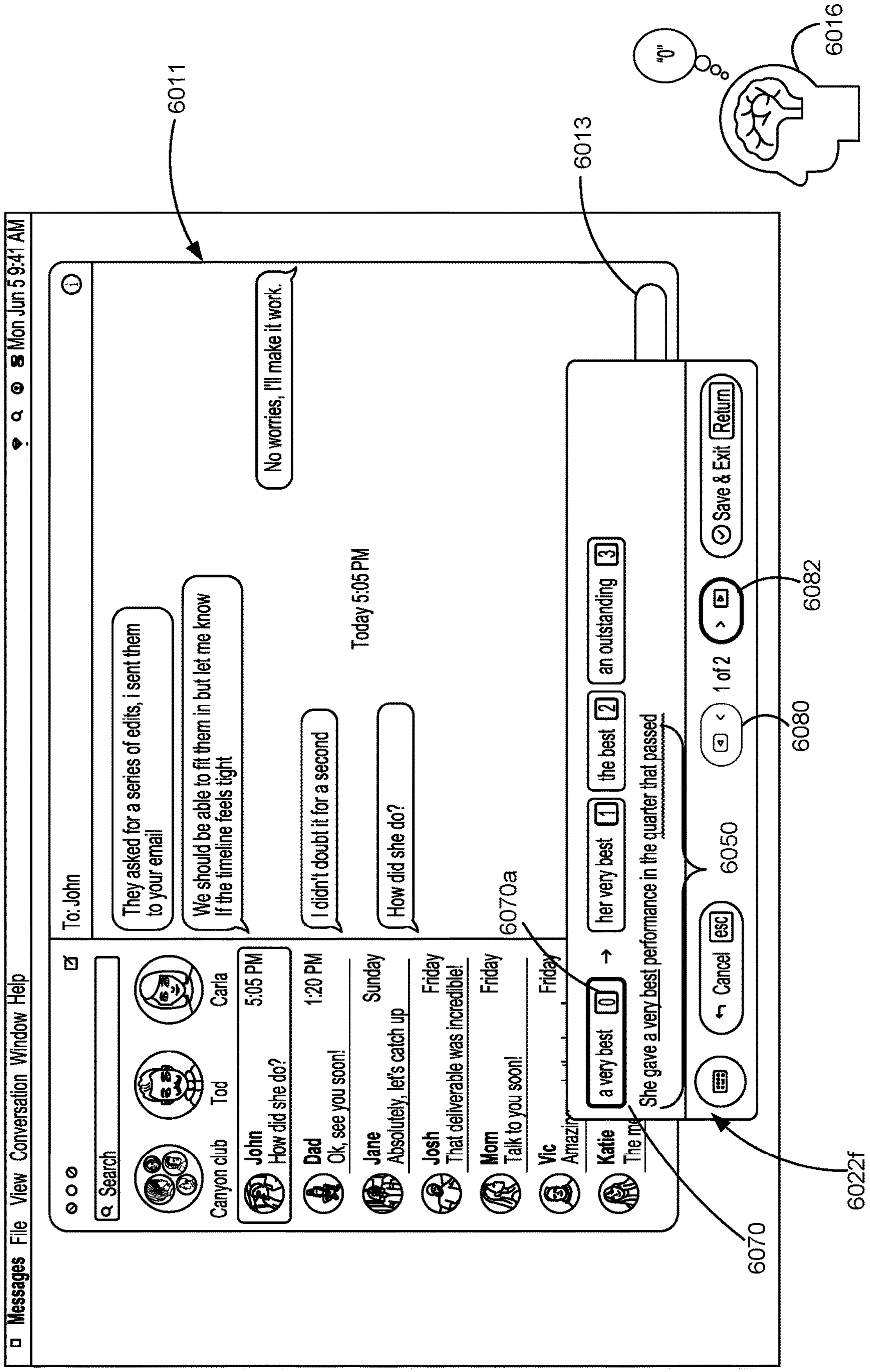
Figure 6N:
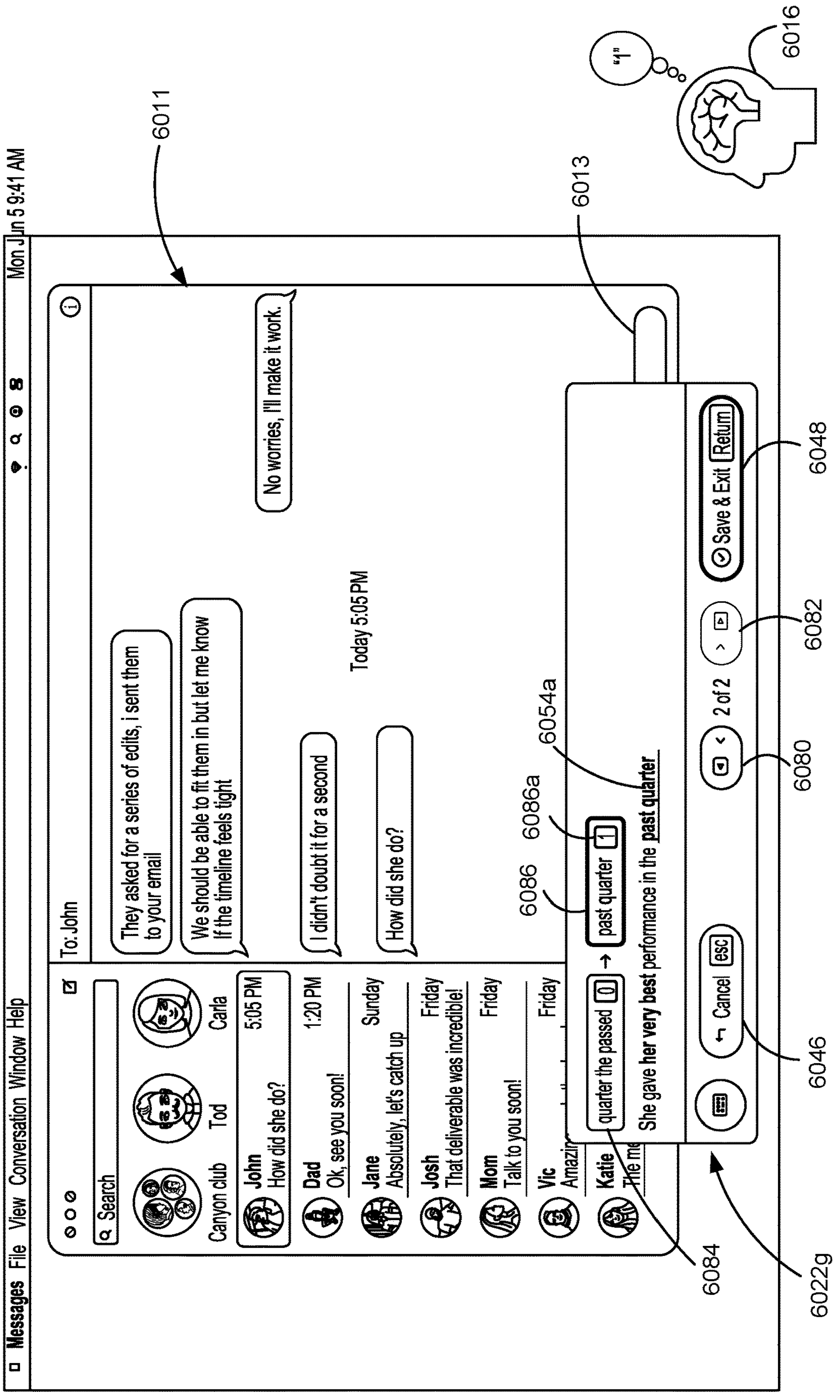
Figure 6O:
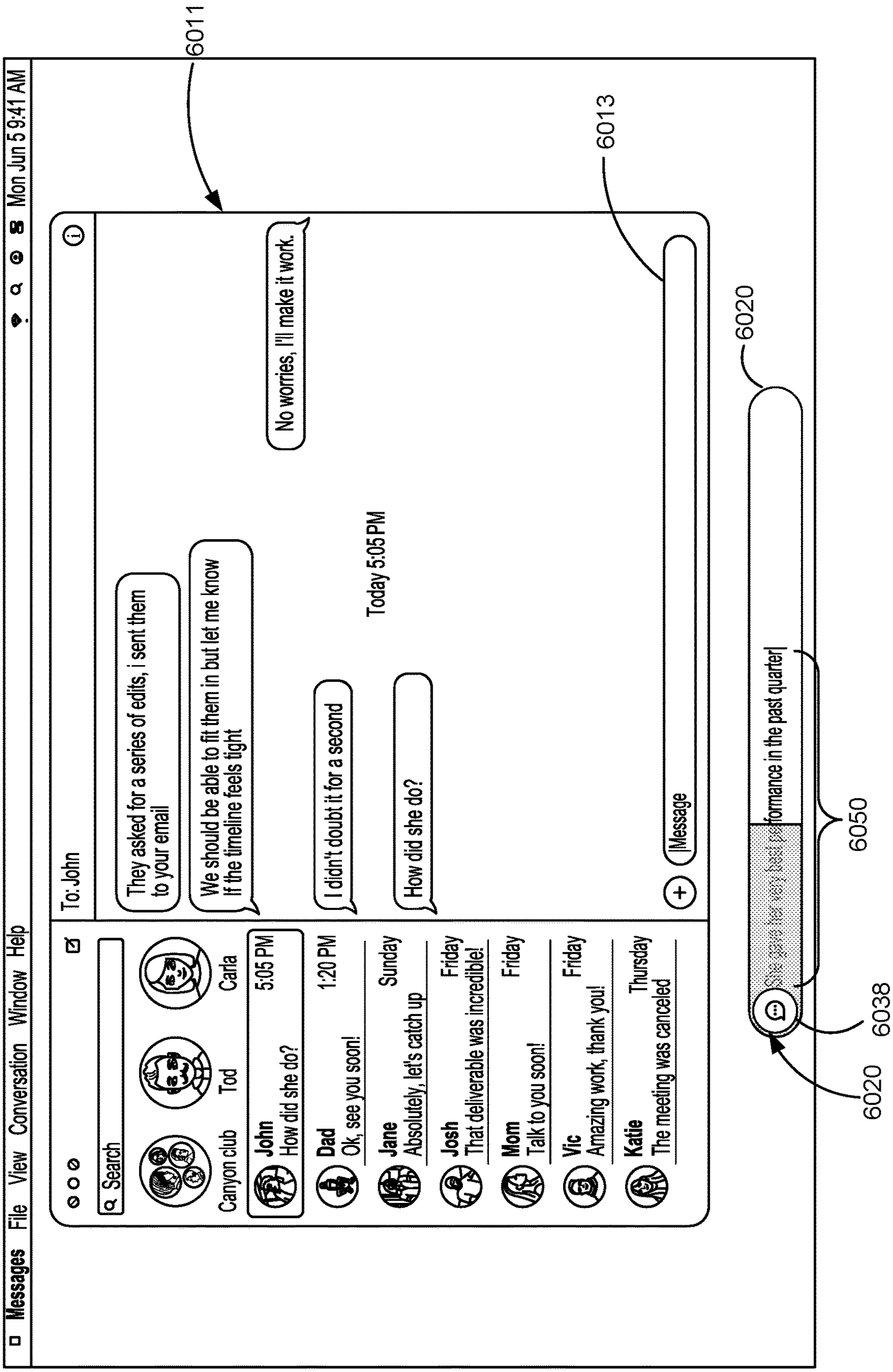
Figure 6P:
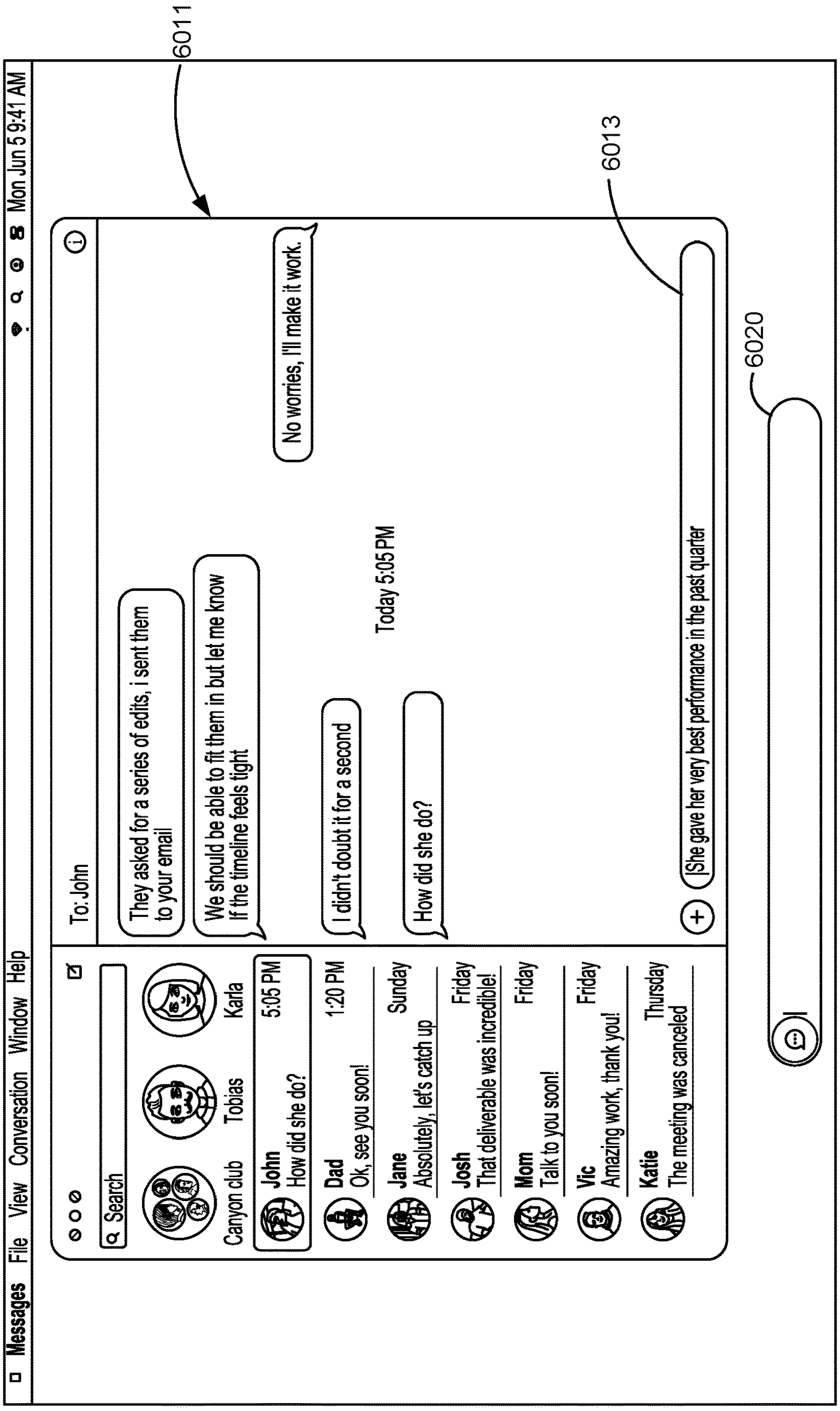
Figure 7:
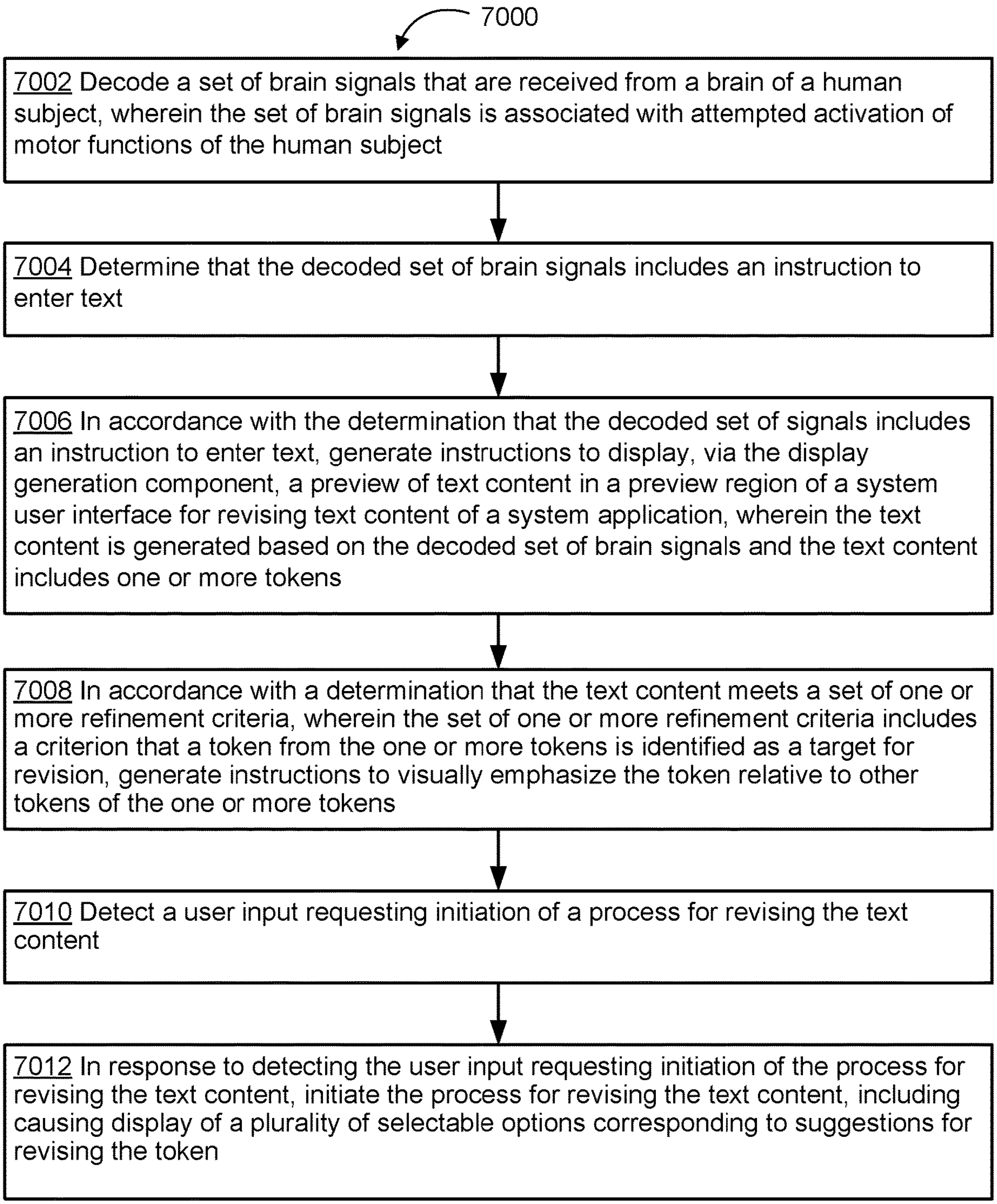
FIG. 7 is a flow diagram of a method of editing and entering neural text output, in accordance with some embodiments.

FIGS. 6A-6P illustrates example user interfaces and techniques for editing and entering neural text output, in accordance with some embodiments. FIG. 7 is a flow diagram of a method of editing and entering neural text output, in accordance with some embodiments. The user interfaces in FIGS. 6A-6P are used to illustrate the processes in FIG. 7.

FIGS. 6A-6H illustrate example user interface for previewing generated neural text output in a system user interface (e.g., also referred as a refinement user interface) and submitting the generated neural text output to a text bar of an application user interface, in accordance with some embodiments. In some embodiments, FIGS. 6A-6H illustrate an example where the generated neural text output does not meet refinement criteria and is submitted to the text bar of the application user interface without edits.

FIG. 6A illustrates a desktop user interface 6002, icon 6004, and dock 6006 displayed on a display of computing device 140. Icon 6004, when selected, causes the computing device 140 to display a system user interface for previewing and revising neural text content. Dock 6006 includes various application icons for opening applications available on computing device 140. For example, dock 6006 includes messages application icon 6008 for opening or launching the messages application.

FIG. 6B illustrates a transition from FIG. 6A in response to detecting a user input opening the messages application. In some embodiments, the messages application is opened in response to a detection of a selection input directed toward the messages application icon 6008 (e.g., an input detected via a pointing device, a touch input, a gesture and/or other user input that requires motor control from the user) or in response to a neural-based command (e.g., decoded brain signals that correspond to a speech command requesting that the messages application be opened). FIG. 6B illustrates user interface 6010 of the messages application. In some embodiments, in response to opening the messages application, in accordance with a determination that the messages application includes a text bar 6012, the computing device 140 automatically displays a preview text bar 6020 of a system user interface 6022 for previewing and revising neural text content. In some embodiments, the system user interface 6022 is referred to as refinement user interface. For example, the computer system 140 displays an animation where preview text bar 6020 expands from icon 6004. In some embodiments, the preview text bar 6020 is displayed in response a user input selecting text bar 6012 of the messages application. In some embodiments, text bar 6012 is selected in response to a conventional user input (e.g., an input detected via a pointing device, a touch input, a gesture and/or other user input that requires motor control from the user) or in response to a neural-based command. Caret 6014 indicates that text bar 6012 of the messages application is in focus. In some embodiments, icon 6004 indicates that system user interface 6022 for previewing and revising neural text content is in a dictate mode. In the dictate mode, the computing device 140 continuously processes brain activity (e.g., captures brain signals), decodes the brain activity to generate neural text output, and automatically types the generated neural text output into preview text bar 6020 of the system user interface 6022.

FIG. 6C illustrates that the computing device 140 automatically inputs (e.g., enters or types) neural text output 6018 into preview text bar 6020 of the system user interface 6022 in response to detecting and decoding user 6016's brain signals. For example, FIG. 6C illustrates that the neural text output "It went . . . " is typed into preview text bar 6020. Typing the generated neural text output 6018 into preview text bar 6020 provides continuous visual feedback to the user regarding whether the computer system is accurately decoding the brain activity, thereby allowing the user to adjust and refine their brain activity and/or to adjust and refine the generated neural text output before the neural text output 6018 is submitted to text bar 6012 of the messages application.

FIGS. 6D-6E illustrate that the computing device 140 continues to automatically type neural text output 6018 into preview text bar 6020 of the system user interface 6022 in response to capturing and decoding user 6016's brain signals. For example, FIG. 6D illustrates that the neural text output 6018 is further completed by automatically typing "It went well, they . . . " into preview text bar 6020 and FIG. 6E illustrates that the neural text output 6018 is further completed by typing "It went well, they were really happy . . . " into preview text bar 6020. The state of icon 6004 in FIGS. 6D-6E relative to the state of icon 6004 in FIG. 6B indicates that the computing device 140 continues to capture and decode user 6016's brain signals. For example, changing icon 6004 to alternate between displaying one, two, or three dots indicates that the computing device 140 continues to capture and decode user 6016's brain signals, whereas maintaining display of three dots in the icon 6004 (e.g., for at least a threshold amount of time after the number of dots in icon 6004 changed) indicates that the computing device 140 has ceased to detect and decode user 6016's brain signals.

FIG. 6F illustrates that the computing device 140 has ceased to capture and decode user 6016's brain signals. For example, icon 6004 has ceased to alternate between displaying one, two, and three dots, and the user 6016 is no longer generating brain activity associated with attempted speech. In some embodiments, in accordance with a determination that the computing device 140 has not detected and decoded user 6016's brain signals that are associated with attempted speech for more than a threshold amount of time (e.g., because user 6016 has finished dictation), the computing device 140 automatically initiates a timeout finalization process for entering neural text output 6018 into text bar 6012 of user interface 6010 of the messages application. For example, in accordance with a determination that the computing device 140 has not detected and decoded user 6016's brain signals that are associated with attempted speech for more than a threshold amount of time, the computing device 140 starts a timer 6026 that when expires causes the computing device 140 to automatically submit neural text output 6018 to text bar 6012 of user interface 6010 of the messages application. FIG. 6F illustrates progress bar 6024 that automatically updates to reflect the running timer. In FIG. 6F, the timeout finalization process for entering neural text output 6018 as input into text bar 6012 has been initiated (and timer 6026 has been started) but not yet completed, as indicated by the partially complete progress bar 6024.

FIG. 6G illustrates that neural text output 6018 is submitted to text bar 6012 of user interface 6010 of the messages application. FIG. 6G shows that the computing device 140 has automatically submitted neural text output 6018 into text bar 6012 in accordance with a determination that the timer 6026 has expired (e.g., the timer 6026 has expired without detecting user input requesting to stop the timeout finalization process). In some embodiments, instead of automatic submission of the neural text output 6018 from the review text bar 2020 to the text bar 6012 of user interface 6010, the neural text output 6018 can be submitted manually in response to a user input, as described in further detail below in reference to FIG. 6H.

FIG. 6H illustrates different states of the preview text bar 6020 of the system user interface 6022, in accordance with some embodiments. For example, preview text bar 6020*a*, preview text bar 6020*b*, preview text bar 6020*c*, preview text bar 6020*d*, and preview text bar 6020*d* illustrate different states of the preview text bar 6020 (e.g., collectively referred to as states 6020*a*-6020*e*). In some embodiments, icon 6028 indicates that the system user interface 6022 is in a dictate mode. In FIG. 6H, icon 6028*a*, icon 6028*b*, icon 6028*c*, icon 6028*d*, and icon 6028*e* illustrate that in all states 6020*a*-6020*e*, the system user interface 6022 is in the dictate mode, where in the dictate mode, the computing device 140 continuously processes brain activity, decodes the brain activity to generate neural text output, and automatically types the generated neural text output into preview text bar 6020 of the system user interface 6022. Preview text bar 6020*a* illustrates an empty state of the preview text bar 6020, where no neural text output has been typed in yet. Preview text bar 6020*b* illustrates a state of the preview text bar 6020 after some neural text output has been typed into the preview text bar 6020 and while neural text input is still being captured and decoded. Icon 6028*b* of preview text bar 6020*b* indicates that brain activity from the user 6016 is actively being captured and decoded (e.g., as indicated by icon 6028*b* that has less than three dots). Preview text bar 6020*c* illustrates a state of the preview text bar 6020 after a user has finished dictating and after the computing device 140 has finished typing in the generated neural text output into preview text bar 6020. Preview text bar 6020*d* illustrates that the timeout finalization process is in progress, where after the timeout expires, the computing device 140 automatically submits the neural text output as input to the text bar of an application user interface (e.g., the text bar 6012 of the messages application). Preview text bar 6020*e* illustrates a state of the preview text bar 6020 after a user has finished dictating and after the computing device 140 has finished typing in the generated neural text output into preview text bar 6020. Further, in preview text bar 6020*e*, manual finalization is enabled via return control 6021. For example, in response to a user input selecting return control 6021, the computing device 140 transmits neural text output from the preview text bar 6020 to a text bar or other region of an application user interface (e.g., the text bar 6012 of the messages application). The return control 6021 includes a visual indication of a "Return" command that when executed and/or detected causes the computing device 140 to transmit the neural text output from the preview text bar 6020 to a text region of an application user interface. For example, the return control 6021 can be selected in response to neural-based input that, when decoded, corresponds to a speech command of the words "Return." In some embodiments, the return control 6021 can be selected in response to a keyboard input selecting a "return key" on the keyboard. In some embodiments, the return control 6021 can be selected in response to a touch input, a mouse input, and/or other selection inputs. In response to selecting the return control 6021, the computing device 140 transmits the neural text output from the preview text bar 6020 to a text region of an application user interface. Preview text bar 6020*f* illustrates a state of the preview text bar 6020, where multiple lines of decoded neural text output have been decoded and typed into the preview text bar 6020.

In some embodiments, in accordance with a determination that generated neural text output meets refinement criteria, suggestions for revising the neural textual output are generated by the computing device 140. For example, in accordance with a determination that fragments of the neural text output can be improved or corrected, selectable options corresponding to suggestions for revising a respective fragment of the neural text output are displayed in the system user interface 6022.

FIGS. 6I-6J illustrate the system user interface 6022 before and after a process for revising neural text output is initiated, where the neural text output meets refinement criteria, in accordance with some embodiments.

FIG. 6I illustrates the system user interface 6022 with preview text bar 6020 while the dictate mode is active, as indicated by icon 6038. Neural text output 6030 (e.g., "They liked both options but ultimately choose the first one") that is generated in response to capturing and decoding the user 6016's brain activity is displayed in the preview text bar 6020. In some embodiments, in accordance with a determination that a fragment 6034 of neural text output 6030 is targeted for revision, the computing device 140 automatically highlights and/or underlines fragment 6034 of neural text output. Highlighting and/or underlining fragment 6034 of neural text output 6030 (e.g., "ultimately choose") provides visual feedback to the user 6016 that the fragment 6034 is incorrected and/or that options to improve and revise fragment 6034 are available. Different methods and/or criteria for determining whether the neural text output 6030 meets refinement criteria are described in further detail below with reference to method 7000 and FIG. 7. Further, in accordance with a determination that the neural text output 6030 meets refinement criteria (e.g., a fragment 6034 of the neural text output 6030 is identified as a target for revision), the computing device 140 automatically displays a control option 6032 for initiating a process for revising the neural text output 6030. The control option 6032 includes a visual indication 6032*a* of a "tab" command that, when executed and/or detected, causes the computing device 140 to initiate a process for revising the neural text output 6030. For example, the control option 6032 can be selected in response to a neural-based input that corresponds to a speech command of the words "tab." In some embodiments, the control option 6032 can be selected in response to a keyboard input selecting a "tab" key on the keyboard. In some embodiments, the control option 6032 can be selected in response to a touch input, a mouse input, and/or other selection inputs. Optionally, the control option 6032 includes a user interface element 6036 that indicates a number of fragments in the neural text output 6030 that are identified as targets for revision. Since a single fragment is targeted for revision in the neural text output 6030 (e.g., fragment 6034 "ultimately choose"), the user interface element 6036 indicates a total number of "1" fragment. In response to selecting the control option 6032, the computing device 140 activates a refine mode. In the refine mode, the computing device 140 does not generate text output based on the user 6016's brain activity (e.g., in contrast to the dictate mode, where the computing device 140 generates text output based on the user 6016's brain activity).

FIG. 6J illustrates different states 6022*a*, 6022*b*, and 6022*c* of the system user interface 6022, where a single fragment is identified as a target for revision in the neural text output 6031, in accordance with some embodiments. In state 6022*a*, the fragment 6035 in neural text output 6031 is identified as a target for revision, and the fragment 6035 is underlined relative to other portions of neural text output 6031 displayed in the preview text bar 6020. In state 6022*a*, the control option 6032 is displayed in response to detecting that the fragment 6035 in the neural text output 6031 is identified as a target for revision. State 6022*b* of the system user interface 6022 is an intermediary state in which the timeout finalization process has been initiated (e.g., as indicated by the progress bar 6042 in the preview text bar 6020). In some embodiments, before the timeout finalization process is completed, the user 6016 initiates the process for revising neural text output 6031 (e.g., by providing neural input corresponding to the command "tab" that when detected causes the computing device 140 to initiate the process for revising neural text output 6031 and/or to select control option 6032 that, when selected, causes the computing device 140 to initiate the process for revising neural text output 6031). Further, state 6022*b* illustrates an intermediate state of the system user interface 6022 after selecting the control option 6032 but before suggestions for revising fragment 6035 are displayed in the system user interface 6022. In some embodiments, the computing device 140 provides visual feedback that the control option 6032 is selected and/or that a neural-based input that corresponds to the speech command "tab" has been detected. For example, in response to selecting the control option 6032 (e.g., using neural-based inputs and/or other conventional inputs, such as a mouse input, a keyboard input, and/or a touch input), the computing device 140 displays tab icon 6044 to indicate that the tab command has been detected and/or executed. Further, optionally, the computing device 140 changes visual appearance of the control option 6032 to indicate that the control option 6032 is selected (e.g., visual appearance of control option 6032 in state 6022*b* relative to visual appearance of control option 6032 in state 6022*a* of the system user interface 6022). In some embodiments, in response to initiating the process for revising neural text output 6031 (e.g., in response detecting neural input from the user 6016 corresponding to the command "tab" and/or in response to a user input selecting control option 6032), the computing device 140 activates the refine mode and replaces icon 6038 that indicates that the dictate mode is active with icon 6040 that indicates that the refine mode is active, as illustrated in state 6022*b* of the system user interface 6022.

State 6022*c* illustrates the system user interface 6022 after the process for revising neural text output 6031 is initiated and while the refine mode is active (e.g., in response detecting neural input from the user 6016 corresponding to the command "tab" and/or in response to a user input selecting control option 6032). In some embodiments, in response to detecting and decoding brain activity from the user 6016 corresponding to the command "tab", the computing device 140 expands the system user interface 6022 to display option 6060, option 6062, and option 6064 corresponding to suggestions for revising the fragment 6035 of the neural text output 6031, and cancel button 6046 and save button 6048. In some embodiments, option 6060, option 6062, and option 6064 are ordered in a sequence, where option 6060 is first, option 6062 is second, and option 6064 is third. Option 6060 "ultimately chosen" corresponds to original fragment 6035 without modification. Option 6062 "ultimately chose" and option 6064 "ended up choosing" correspond to options that are determined by the computing device 140 to be suitable replacements for fragment 6035 in the neural text output 6031. Different methods and/or criteria for determining suitable options for revising fragments of the neural text output 6030 are described in further detail below with reference to method 7000 and FIG. 7. Each option 6060, 6062, and 6064 includes a visual indication of a command that when executed causes the computing device 140 to select a respective option. For example, option 6060 includes visual indication 6060*a* of a command "0" that when executed causes the computing device 140 to select the option 6060. For example, the option 6060 can be selected in response to neural-based input that corresponds to a speech command of the word "0." In some embodiments, the option 6060 is selected in response to a keyboard input selecting a "0" key on the keyboard. In some embodiments, the option 6060 can be selected in response to a touch input, a mouse input, and/or other selection inputs. Similar to option 6060, the option 6062 includes a visual indication 6062*a* of a command of a command "1" and the option 6064 includes a visual indication 6064*a* of a command of a command "2." For example, the option 6062 is selected in response to detecting a neural-based input that corresponds to a speech command of the word "1" and the option 6064 is selected in response to neural-based input that corresponds to a speech command of the words "2." In response to selecting a respective option from options 6060, 6062, and 6064 (e.g., collectively referred to as options 6060-6064), the computing device 140 replaces fragment 6035 in the preview bar 6020 with the selected option. For example, if the user 6016 presses key "1" on the keyboard or attempts to say the word "1," the computing device 140 replaces fragment 6035 "ultimately chosen" with the selected option 6062 "ultimately chose" in the preview bar 6020. In some embodiments, the computing device reverts to the original neural text output 6031 in response to detecting a press input on key "0" on the keyboard or in response to a neural-based input that corresponds to the word "0." In some embodiments, the user 6016 can go back to state 6022*a* of the system user interface 6022 without saving any revisions made to the neural text output 6031 by selecting cancel button 6042. As with other options or controls in the system user interface 6022, the cancel button 6042 can be selected in response to detecting a neural-based input that corresponds to a speech command of the word "escape" (e.g., where the command escape is indicated by visual indication 6046*a* "esc"), in response to detecting a keyboard input selecting a "esc" key on the keyboard, and/or other neural-based or motor-based input. In some embodiments, any changes made to the neural text output 6031 are saved in response to detecting a selection of save button 6048. Save button 6048 includes visual indication 6048*a* of a command "return" that when executed (e.g., in response to detecting neural based input of the command "return") causes the computing device 140 to select the save button 6048. In response to selecting save button 6048, the computing device 140 exits the refine mode, reactivates the dictate mode, and replaces the fragment 6035 with the text of option 6062 in the preview text bar 6020. In some embodiments, after the computing device 140 reactivates the dictate mode, the user 6016 can continue to dictate additional text and the computing device 140 continues to process and decode any brain activity of the user 6016 in order to generate additional neural text in the preview text bar 6020.

In some embodiments, FIG. 6K illustrate different states of the system user interface 6022, where multiple fragments of the neural text output are identified as targets for revision.

FIG. 6K illustrates state 6022*d* of the system user interface 6022 while the dictate mode is active, as indicated by icon 6038. Neural text output 6050 "She gave a very best performance in the quarter that passed" (e.g., generated in response to capturing and decoding the user 6016's brain activity) is displayed in the preview text bar 6020. In accordance with a determination that two fragments 6052 and 6054 of neural text output are identified as targets for revision, the computing device 140 automatically highlights and/or underlines both fragments 6052 and 6054 of the neural text output 6050. Use interface element 6037 indicates that the computing device 140 has identified two targets for revision in the neural text output 6050 (e.g., in contrast to user interface element 6036 in FIG. 6J where only one fragment 6035 is identified as a target for revision). Icon 6040 in state 6022*e* illustrates that the system user interface 6022 is in the refine mode (e.g., activated in response to detecting an input selecting the control option 6032). In response to detecting an input selecting the control option 6032 (e.g., in response to detecting a neural-based input correspond to the command "tab"), the computing device 140 initiates the process for revising neural text output 6050, activates the refine mode, and expands the system user interface 6022 to display option 6070, option 6072, option 6074, and option 6076 (e.g., collectively referred to as options 6070-6076) corresponding to suggestions for revising the first identified fragment 6052 of the neural text output 6050. As in FIG. 6J, each option of options 6070-6076 includes a visual indication of a command that when executed causes the computing device 140 to select the respective option from the options 6070-6076. For example, the option 6070 includes visual indication 6070*a* of a command "0" that when executed (e.g., in response to detecting neural based input of the command "0") causes the computing device 140 to select the option 6070. Similarly, the option 6072 includes visual indication 6072*a* of a command "1", the option 60742 includes visual indication 6074*a* of a command "2", and the option 6076 includes visual indication 6076*a* of a command "3".

In addition to the cancel button 6046 and the save button 6048, the computing device 140 displays a navigation control 6080 and a navigation control 6082 for switching between identified fragments for revision. For example, while in state 6022*e* options 6070-6076 for revising the fragment 6052 are displayed; in state 6022*g*, the system user interface 6022 displays an option 6084 and an option 6086 (e.g., collectively referred to as options 6084-6086) for revising fragment 6054. The computing device 140 switches from displaying options 6070-6076 for revising the fragment 6052 in state 6022*f* to displaying the options 6084-6086 for revising the fragment 6054 in state 6022*g* in response to detecting an input selecting the navigation control 6082 (e.g., a touch input, a hand gesture, a mouse click, an air gesture, a gaze input, and/or decoded brain signals that correspond to attempted speech, movement, or otherwise an attempt to control an effector). The computing device 140 switches from displaying the options 6084-6086 for revising the fragment 6054 to displaying the options 6070-6076 for revising the fragment 6052 in response to detecting an input selecting the navigation control 6080.

State 6022*e* of the system user interface 6022 is displayed in response to detecting an input selecting option 6072, which corresponds to the first option for revising the text of fragment 6052. Because the user 6016 selected the option 6072, the fragment 6052 "a very best" is replaced with a fragment 6052*a* "her very best" in the in the preview text bar 6020. The computing device 140 underlines fragment 6052*a* differently than fragment 6052 before it was replaced to indicate that the selected fragment 6052 has been replaced. State 6022*f* of the system user interface 6022 is displayed in response to detecting an input selecting option 6070, which corresponds to the original text of fragment 6052. Because the user 6016 selected the option 6070 corresponding to the original text of fragment 6052, the neural text output 6050 in the preview text bar 6020 remains unchanged. Further, the visual appearance of fragment 6052 is changed in state 6022*f* after option 6070 is selected relative to the visual appearance of fragment 6052 in state 6022*d* before the option 6070 is selected (e.g., fragment 6052 is underlined differently). The computing device 140 transitions from state 6022*e* to state 6022*g* of the system user interface 6022 in response to detecting an input selecting the navigation control 6082.

FIGS. 6L-6P illustrate interaction of the user 6016 with the system user interface 6022 while a user interface 6011 of the messages application is displayed and after the process for revising text output 6050 has been initiated (e.g., in response to detecting a neural-based input correspond to the command "tab"). In FIG. 6L, the system user interface 6022 is the state 6022*e* as illustrated in FIG. 6K. The computing device transitions from the state 6022*d* to the state 6022*e* in response to detecting a neural-based input that corresponds to a speech command of the word "1", where the detected command "1" is associated with the option 6072 (e.g., as indicated by visual indication 6072*a*). In response to detecting the neural-based input that corresponds to the speech command of the word "1," the computing device 140 selects option 6072 and reverts to the original neural text output 6050. For example, the computing device 140 replaces the text fragment 6052 "her very best" with the original text fragment 6052 "a very best" in the system user interface 6022.

In FIG. 6M, the system user interface 6022 is in the state 6022*f* (e.g., as in FIG. 6K). The computing device transitions from the state 6022*e* to the state 6022*f* in response to detecting a neural-based input that corresponds to a speech command of the word "0", where the detected command " " is associated with the option 6070.

FIG. 6N illustrates the system user interface 6022 after an input selecting the navigation control 6982 has been selected. For example, in response to detecting an input selecting the navigation control 6082, the computing device 140 switches from displaying options 6070-6076 for revising the fragment 6052 in state 6022*f* to displaying the options 6084-6086 for revising the fragment 6054 in state 6022*g*. Further, in FIG. 6N, the computing device 140 has replaced the fragment 6054 "quarter that passed" with text fragment 6054*a* "past quarter" in response to detecting a neural-based input that corresponds to a speech command of the word "1", where the detected command "1" is associated with the option 6086 (e.g., as indicated by visual indication 6086*a*).

FIG. 6O illustrates a transition from FIG. 6N in response to detecting a user input selecting the save button 6048. In response to detecting a user input selecting the save button 6048 (e.g., in response to detecting neural based input of the command "return"), the computing device 140 exits the refine mode, reactivates the dictate mode, and collapses the system user interface 6022 (e.g., by ceasing to display navigation controls 6084 and 6086, cancel button 6046, save button 6048, and the navigation controls 6082 and 6084). Further, the computing device 140 replaces the fragment 6054 with the fragment 6054*a* in the preview text bar 6020. In some embodiments, in accordance with a determination that a predetermined amount of time passed after the dictate mode has been reactivated, the computing device 140 automatically initiates a timeout finalization process. FIG. 6O illustrates that the timeout finalization process is in progress but is not yet completed.

FIG. 6P illustrates a transition from FIG. 6O in response to detecting that the timeout finalization has been completed (e.g., the timer expired). In FIG. 6P, the computing device 140 automatically submitted the neural text output 6050, with revisions made as described in FIG. 6N, to the text bar 6013 of the messages application.

FIGS. 6A-6P illustrates example user interfaces and techniques for editing and entering neural text output, in accordance with some embodiments. FIG. 7 is a flow diagram of a method 7000 of editing and entering neural text output, in accordance with some embodiments. The user interfaces in FIGS. 6A-6P are used to illustrate the processes in FIG. 7.

In some embodiments, method 7000 is performed at a computer system (e.g., computing device 140 or server system 160) that includes one or more processors and memory. The computer system includes or is communicatively connected to a display generation component (e.g., display 170 or external display device 173), one or more input devices, and one or more cameras. The memory stores one or more programs configured for execution by the one or more processors. In some embodiments, the operations shown in FIGS. 1A to 1D, 2A to 2D, 3A, 3B, and 6A to 6P correspond to instructions stored in the memory or other non-transitory computer-readable storage medium. The computer-readable storage medium may include a magnetic or optical disk storage device, solid state storage devices such as Flash memory, or other non-volatile memory device or devices. In some embodiments, the instructions stored on the computer-readable storage medium include one or more of: source code, assembly language code, object code, or other instruction format that is interpreted by one or more processors. Some operations in the method 7000 may be combined with other operations, and/or the order of some operations may be changed.

As described herein, method 7000 is directed to an improved technique and a user interface for revising neural text output (e.g., text output generated based on decoded brain signals). Method 7000 is directed to a specific BCI text-input architecture in which neural signals are decoded into text, uncertain portions of neural text output are identified for revision. The Text output generated based on decoded brain signals can previewed and, optionally, revised in a system user interface. The system manages revision (e.g., automatically or in response a user input) through a separate preview workflow before it is submitted/committed to a text region of an application. In some embodiments, the system user interface is managed by a BCI system and is separate from the application and application user interface. The system user interface optionally operates in two modes: (1) a dictate mode and (2) a refine mode. In the dictate mode, the computer system continuously processes brain activity (e.g., electrical or optical brain signals), decodes the brain activity to generate neural text output, and automatically types the generated neural text output into a preview region (e.g., preview text bar 6020) of the system user interface. Typing the generated neural text output into the preview region provides continuous visual feedback to the user regarding whether the computer system is accurately decoding the brain activity, thereby allowing the user to adjust and refine their brain activity and/or to adjust and refine the generated neural text output. In the refine mode, the computer system suspends the continuous free-form neural text generation and instead processes a reduced set of revision-related commands and option-selection inputs. In accordance with a determination that the neural text output meets refinement criteria, suggestions for revising the neural textual output are generated by the computer system. Selectable options corresponding to suggestions for revising a respective fragment of the neural text output are displayed in the system user interface (e.g., optionally in response to activating the dictate mode or in response to the determination that the neural text output meets refinement criteria, where the options are selectable using neural-based inputs in addition to conventional user inputs, thereby providing accommodation for users with motor and/or speech impairments. Automatically displaying options for revising neural text output before the neural text output is submitted or transmitted to an application user interface as input, where the options can be selected in response neural-based inputs, provides additional control to the user to revise and refine neural text output with different input modalities and/or reduces the number of inputs and/or amount of time needed to enter text input into a text region of an application user interface (e.g., by reducing the number of errors in neural text output).

At operation 7002, the computer system decodes a set of brain signals that are received from a brain of a human subject, wherein the set of brain signals is associated with attempted activation of motor functions of the human subject. In some embodiments, brain signals from a brain of a user are detected via implant device 110 (e.g., FIGS. 1A, 2A, and 2C) and are decoded by a decoder model (e.g., signal processing module 446 or signal processing module 546) to determine attempted and/or intended user actions associated with the brain signals. In some embodiments, the set of decoded brain signals are associated with attempts of the user to speak, move, perform a gesture, and/or otherwise control an effector such as a keyboard or a cursor by sending signals to it, which then can cause the effector to produce a desired response.

At operation 7004, the computer system determines that the decoded set of brain signals includes an instruction to enter text. In some embodiments, the instruction is to enter text input in a text region of a user interface, where the text region is configured to receive text input (e.g., a user interface of a messaging application, an email application, a document editing application, a search or address bar of a browser application, a form or other document access via a browser application, and/or other user interface configured to receive text input) that is displayed, via the display generation component at a time the instruction is received. For example, instructions to enter neural text output 6018 in text bar 6012 of the messages application in FIGS. 6A-6G.

At operation 7006, in accordance with the determination that the decoded set of signals includes an instruction to enter text (e.g., text input), the computer system generates instructions to display, via the display generation component, a preview of text content in a preview region (e.g., a text bar, a refinement bar, such as preview text bar 6020, and/or other field for previewing and/or revising the text content before sending the text content to the first region of the application user interface) of a system user interface for revising text content of a system application (e.g., a BCI application installed or running on the computer system), wherein the text content is generated based on the decoded set of brain signals and the text content includes one or more tokens. In some embodiments, the preview region of the system user interface operates as an intermediate system-managed text buffer that is separate from a text region of an application user interface, so that neural text output can be rendered, evaluated, and selectively revised before the neural text output is committed to the application user interface. By separating neural decoding from application text commitment, the computer system can reduce propagation of decoding errors into the application and provide a more stable input mechanism for users whose input is generated from decoded brain activity rather than limb motion or vocalized speech.

In some embodiments, the one or more tokens include text fragments and/or text portions including, but not limited to, individual words, phrases, portions of sentences, sentences and/or other units of text. For example, tokens are the basic building blocks of text that are analyzed and processed by natural language processing algorithms.

At operation 7008, in accordance with a determination that the text content meets a set of one or more refinement criteria, wherein the set of one or more refinement criteria includes a criterion that a token from the one or more tokens is identified as a target for revision, generate instructions to visually emphasize the token relative to other tokens of the one or more tokens.

In some embodiments, the text content meets the set of one or more refinement criteria when the text content includes one or more of: a spelling error, a grammar-related error, a contextually inappropriate word, a subject-verb agreement error, a misplaced modifier, use of passive voice, and a syntactic error. In some embodiments, a decoder model is applied to decode the set of brain signals and generate the text content based on the decoded set of brain signals, and the text content meets the set of one or more refinement criteria when one or more statistical properties of the set of decoded brain signals indicate an ambiguity or an error in the text content, or when a decoding confidence score output by the decoder model is below a threshold confidence score.

In some embodiments, visually emphasizing the token relative to the other tokens includes underlining, highlighting, making bold, italics, changing font, and/or otherwise distinguishing the token from the other tokens. For example, in FIG. 6K the fragment 6052 and the fragment 6054 are underlined because the fragments 6052 and 6054 are identified as revision targets, whereas other fragments of neural text output 6050 are not underlined.

At operation 7010, the computer system detects a user input (e.g., a touch input, a hand gesture, a mouse click, an air gesture, a gaze input, and/or decoded brain signals) requesting initiation of a process for revising the text content. In some embodiments, in accordance with a determination that the text content meets the set of one or more refinement criteria, the computer system displays an option for activating a "refinement mode" (e.g., a button, a control, or other user interface element). For example, in FIG. 6I, the control option 6032 is displayed in accordance with a determination that fragment 6034 is identified as a target for revision. In some embodiments, the process for revising the text content is initiated in response to detecting a selection input directed to the option for activating the "refinement mode" (e.g., also referred to as a "refine mode", a "revision mode", and editing mode).

At operation 7012, in response to detecting the user input requesting initiation of the process for revising the text content, the computer system initiates the process for revising the text content, including causing display of a plurality of selectable options (e.g., system-generated options) corresponding to suggestions for revising the token. In some embodiments, the computer system uses various algorithms to identify tokens as targets for revision and generate suggestions for improving the text content including, but not limited to, machine learning models, rule-based algorithms, text-classification algorithms, rule-based style guidelines, spell-checking algorithms, and/or grammar checking algorithms. In some embodiments, the set of one or more refinement criteria is satisfied in accordance with a determination that one or more of these algorithms flag part of the text content. For example, the set of one or more refinement criteria is met when the computer system detects errors, such as spelling or grammar-related errors; identifies contextually inappropriate word choices; identifies issues such as subject-verb agreement, sentence fragments, or misplaced modifiers; identifies syntactical issues; identifies passive voice, overuse of adverbs, and/or wordiness; uses factors like sentence length and syllable count to suggest readability improvements; provides suggestions to maintain consistency in tone and style. In some embodiments, the computer system uses confidence scores or statistical properties of the decoded brain signals to identify possible ambiguities, errors, and/or targets for improvements.

In some embodiments, the system application initially operates in a dictate mode, where in the dictate mode, brain signals are decoded and typed automatically as text input into the preview region of the system user interface for revising text content. In some embodiments, the text content meets the set of one or more refinement criteria in accordance with a determination that a confidence score of the text content, generated by the language model, is lower relative to confidence scores of alternative text outputs, generated by the language mode. For example, the language model associates a respective sentence has a low score relative to other possible sentences with a small character edit distance to the current sentence (e.g., with all values parameterized by the user or a model). Tokens for revision can be identified by where the edit distances are higher. In some embodiments, a beam search generates the top N most likely textual outputs given the brain input data, identifies 2nd, 3rd, 4th, and so on, most likely sentences that are within some absolute or relative range to the 1st (actual or top) most likely sentence that was originally generated. The tokens that differ between the candidate sentences are targeted for revision.

In some embodiments, the method 7000 further includes, in accordance with the determination that the text content meets the set of one or more refinement criteria, the computer system generates instructions to display (e.g., causes display of) an option for initiating the process for revising the text content (e.g. a selectable control or a visual indication of a command), wherein the user input requesting initiation of the process for revising the text content includes a user input selecting the option.

In some embodiments, the option for initiating the process for revising the text content (e.g., the refine control) is displayed concurrently with the preview region of the system user interface for revising text content. In some embodiments, initiating the process for revising the text content includes activating a "refine mode" that is different from the "dictate mode", where the computer system operates in the dictate mode before initiation the process for revising the text content. In some embodiments, the computer system operates in the refine mode before the process for revising text is initiated, and initiating the process for revising the text content does not include activating the refine mode or switching the currently active mode. In some embodiments, in response to initiating the process for revising the text content, the computer system expands the system user interface to display the plurality of selectable options corresponding to suggestions for revising the token. In some embodiments, the option for initiating the process for revising the text content is associated with a command that, when detected, causes the computer system to initiate the process for revising the text content. In some embodiments, the command can be detected based on decoded speech signals received from the brain of the user. In some embodiments, a visual representation of the command or key for selecting the option for activating the refinement mode is displayed (e.g., near the option for activating the refinement mode). For example, a visual indication of the command associated with the option for initiating the process for revising the text content is displayed on the option. In some embodiments, the process for revising the text content is initiated in response to detecting a specific gesture and/or in response to detecting brain signals corresponding to a specific command that are not necessarily associated with a displayed option.

In some embodiments, the instructions to display the option for initiating the process for revising the text content includes an instruction to display a visual indication of a command associated with the option, wherein the command, when executed, causes the option to be selected.

In some embodiments, the visual indication of the command includes a name of a key on a keyboard (e.g., a tab, a command key, an arrow key, a combination of keys, and/or other keyboard key); a letter (e.g., A, B, C, R, etc.); a visual indication of a gesture or a hand movement (e.g., an illustration or other visual indication of a gesture, such as a thumps up, a thumbs down, a pinch, a fist, and/or other illustration of a hand posture or configuration); and/or other visual indication of the command. For example, as in FIG. 6K, each option of options 6070, 6072, 6074, and 6076 includes a respective visual indication 6070*a*, 6072*a*, 6074*a*, and 6076*a* of a command that, when executed, causes the computing device 140 to select the respective option from the options 6070, 6072, 6074, and 6076. In some embodiments, the visual indication of the command is displayed near or in close proximity to the option for initiating the process for revising the text content. In some embodiments, the visual indication of the command is a label displayed on the option for initiating the process for revising the text content.

In some embodiments, the option for initiating the process for revising the text content is adapted to provide accommodation for users with motor and/or speech impairments. For example, displaying the option for initiating the process for revising the text content concurrently with a visual indication of a command associated with the option allows multiple input modalities to be used to select the same option and to initiate the process for revising the text content. In some embodiments, displaying a visual indication of the command associated with the option allows a user to complement conventional input modalities with neural-based inputs, where the neural-based input corresponds to attempted speech of the command. The ability to initiate a process for revising neural text output using neural-based inputs reduces the number of inputs and/or the amount of time needed to enter text and revise neural text output. These and other benefits are particularly beneficial to users with neurological impairments, reduced mobility, speech impairments, and/or other special needs, making interaction with computer systems more accessible to a wider population.

In some embodiments, the user input selecting the option for initiating the process for revising the text content is received by the computer system as a brain signal, and the process for revising the text content includes decoding the brain signal to obtain an instruction to execute the command. In some embodiments, the decoded brain signal corresponds to a speech signal (e.g., an attempt speech that corresponds to or speaks the command). In some embodiments, the decoded brain signal corresponds to non-speech signals, such as a motor signal corresponding to gestures (e.g., finger movements, hand movements, leg movements, head movements, eye movements and/or other movements that are not related to attempts to control effectors related to speech). In some embodiments, the user input selecting the option includes decoded brain signals corresponding an attempted speech that corresponds to the command itself (e.g., an attempt by the user to say "Tab," if the visual indication of the command is a displayed word "Tab" or an attempt by the user to say the letter "R," if the visual indication of the command is a displayed letter "L"). In some embodiments, the user input selecting the option includes decoded brain signals corresponding to an attempted motor gesture to perform a gesture that corresponds to the command. For example, control option 6032 that is associated with the command "tab" is selected in response to detecting a neural-based input that corresponds to the command tab in FIG. 6I-6J.

In some embodiments, the command corresponds to a key on a keyboard, and the user input selecting the option for initiating the process for revising the text content includes pressing the key on the keyboard. In some embodiments, the option for initiating the process for revising the text content is associated with a key on a keyboard (e.g., a tab key) that, when pressed on the keyboard, causes the computer system to initiate the process for revising the text content. In some embodiments, the option for initiating the process for revising the text content is a selectable user interface that can be selected using a touch input, a mouse click, a gaze input, and/or other using other types of inputs. In some embodiments, the keyboard is a physical keyboard that is in communication with the computer system or is coupled to the computer system.

In some embodiments, the option for initiating the process for revising the text content includes a user interface element that corresponds to a total number of tokens from the one or more tokens that are identified as a target for revision (e.g., 1, 2, 3, 4, 5, or other integer number corresponding to the number of tokens that are identified as targets for revision, where a revision target can include a word or a phrase with more than one word). For example, control option 6032 in FIG. 6J includes user interface element 6036 "1" that indicates that only a single target is identified for revision, where the control option 6032 in FIG. 6K includes user interface element 6037 "2" that indicates that two fragments are targeted for revision.

In some embodiments, the user input selecting the option for initiating the process for revising the text content includes a user input activating the command. The method 7000 includes, in response to detecting the user input activating the command, displaying a visual indication that the command is activated. For example, if the visual indication is a label of the command "Tab," the computer system displays (or causes display of) a user interface element (e.g., user interface element 6044 in FIG. 6J) that provides visual feedback to the user that a press input on the keyboard has been detected or that decoded brain signals corresponding to speech command "Tab" have been detected.

In some embodiments, before receiving the instruction to enter text, the computer system detects an event associated with an application (e.g., a user input opening the application or other even that causes the application to be displayed). In response to detecting an event associated with an application, the computer system generates instructions to display, via the display generation component, of an application user interface corresponding to the application. In accordance with a determination that the application user interface includes a text region (e.g., a text field, a text bar, a text box, a text editing area, a search box, and/or other user interface element that is configured to receive text as input) configured to receive text input, the computer system automatically (e.g., without user input) causes display of the preview region of the system user interface (e.g. preview text bar 6020 of the system user interface 6022 in FIGS. 6B-6H), wherein the preview region of the system user interface is configured to receive text input. In some embodiments, the text region of the application (e.g., text bar 6012 in FIGS. 6B-6H) is different from the preview region of the system user interface (e.g. preview text bar 6020 of the system user interface 6022 in FIGS. 6B-6H). In some embodiments, the preview region is used to edit and preview text generated based on the decoded brain signals before the text is transmitted to the text region of the application user interface. In some embodiments, in accordance with a determination that the application user interface does not include a text region, the computer system forgoes displaying (or causing display of) the preview region of the system user interface. In some embodiments, the preview region of the system user interface is displayed without ceasing the display of the application user interface. Automatically displaying or causing display of the preview region in response to detecting that an application user interface that includes a text region is displayed, reduces the number of inputs and/or the amount of time needed to enter text input into the text region of the application user interface.

In some embodiments, the preview region of the system user interface is displayed in response to detecting a user input selecting a text region of an application user interface. In some embodiments, examples of the user input selecting the text region include, but are not limited to, a touch input, a hand gesture, an air gesture, a gaze input (e.g., directed toward the text region for more than a threshold amount of time), an input detected via an external physical device, such as a pointing device (e.g., a mouse), a joystick, a hardware button, a keyboard, a mechanical pedal, a stylus, and/or neural-based input (e.g., inputs generated based on decoded brain signals). In some embodiments, the preview region of the system user interface is displayed in response to a specific gesture. In such a scenario, if the application user interface includes multiple text regions, the computer system determines a target text region based on content of the application user interface (e.g., hierarchy or sequence of user interface elements in the application user interface) and, optionally, subsequence user inputs corresponding to the same specific gesture are used to cycle through the text regions displayed in the application user interface.

In some embodiments, the preview region of the system user interface is different from the text region of the application user interface. Providing a system user interface, with a preview region (e.g., preview bar or preview pane), for editing and previewing neural text output, where the system user interface is configured to submit the neural text output to the text region of the application user interface, provides additional control to the user to revise and refine neural text output with different input modalities and/or reduces the number of inputs and/or amount of time needed to enter text input into a text region of an application user interface (e.g., by reducing the number of errors in neural text output).

In some embodiments, the preview region of the system user interface is concurrently displayed with the application user interface, including the text region of the application user interface. For example, the preview text bar 6020 of the system user interface 6022 is displayed concurrently with the user interface 6010 of the messages application, as illustrated in FIG. 6I.

In some embodiments, the preview region of the system user interface is automatically generated by a system-level process. In some embodiments, the system-level process runs in the background and is configured to assist users with performing tasks on the computer system using different input modalities. In some embodiments, the system-level process includes a BCI, where a combination of technologies and methods are used to process and respond to user inputs that include decoded brain signals. In some embodiments, the system-level process is configured to interact with users through decoded brain signals and other input modalities, such as gestures, body movements, hardware components (e.g., keyboards, switches, buttons, etc.), touch inputs detected via touch-sensitive surfaces, devices uses to control a cursor, such as a mouse or a trackpad, air gestures, gaze inputs, and other input modalities. In some embodiments, the BCI augments input modalities available on the computer system with additional input modalities, including brain signals.

In some embodiments, a first mode (e.g., a dictate mode) is active before the process for revising the text content is initiated, where in the first mode, the system application outputs text content based on decoded brain signals. In some embodiments, the method 7000, includes, in conjunction with initiating the process for revising the text content, the computer system deactivates the first mode and activates a second mode (e.g., a refine mode) different from the first mode, where in the second mode the system application does not continuously generate text content in response to detecting and decoding brain signals. In the refine mode, neural text output is revised by selecting system-generated options for revising the neural text content. For example, FIG. 6J illustrates a transition from the dictate mode to the refine mode in response to detecting a selection and/or a command associated with control option 6032 for initiating the revision process (e.g., transition from state 6022*a* to state 6022 of the system user interface 6022).

In some embodiments, while the first mode is active, a first visual indication that the first mode is active is displayed (optionally, in the system user interface for revising text content), and while the second mode is active, a second visual indication that the second mode is active is displayed (optionally, in the system user interface for revising text content). In some embodiments, in response to switching from the first mode to the second mode, the computer system replaces display of the first visual indication with the second visual indication. In some embodiments, in response to switching from the second mode to the first mode, the computer system replaces display of the second visual indication with the first visual indication. In some embodiments, in response to switching from the first mode (e.g., the dictate mode) to the second mode (e.g., the refine mode), the computer system expands the system user interface to include options for revising tokens or fragments on the neural based output that are targeted for revision and/or other controls for editing the neural based output. In some embodiments, in response to switching from the second mode (e.g., the refine mode) to the first mode (e.g., the dictate mode), the computer system collapses the system user interface (e.g., by ceasing display of controls and/or options for editing the neural text output) and maintains display of a preview text bar that includes neural text output, optionally revised in response to user inputs captured while the second mode (e.g., the refine mode) is active. In some embodiments, before the process for revising the text content is initiated, the second mode (e.g., the refine mode) is active. In some embodiments, in conjunction with initiating the process for revising the text content, the computer system remains in the second mode (e.g., the refine mode). Switching between the dictate mode, where neural-based inputs are used to generate text output, and the refine mode, where neural-based inputs are used to select controls and options (e.g., controls and options for editing the neural-based text output and for navigating the system user interface) displayed in the system user interface, enhances the operability of the device and makes the user-device interface more efficient (e.g., by helping the user to provide proper inputs and reducing user mistakes when operating/interacting with the device) which, additionally, reduces usage of computing resources, memory, power and/or improves battery life by enabling the user to use the computer system more quickly and efficiently.

In some embodiments, initiating the process for revising the text content includes generating instructions to display a set of controls (e.g., one control, or two or more controls) for editing the text content in the text content in the preview region. For example, the set of controls include a control for saving the text content in the preview region (e.g., the save button 6048 in FIG. 6J), optionally, with revisions that are performed in response to user inputs, a control for exiting a refine mode and/or returning to a dictate mode (e.g., same control as control for saving the text content in the preview region) (e.g., the save button 6048 in FIG. 6J); a control for exiting the process for revising text content without saving revisions of the text content in the preview region (e.g., the cancel button 6046 in FIG. 6J); controls for navigating between different tokens that are identified as revision targets (e.g., the navigation controls 6080 and 6082 in FIG. 6K).

In some embodiments, initiating the process for revising the text content includes expanding the system user interface to include the plurality of selectable options corresponding to suggestions for revising the token and the set of controls for editing the text content in the preview region. For example, in FIG. 6K, in response to initiating the revision process, the computing device 140 expands the system user interface 6022 and displays options 6070-6076 corresponding to suggestions for revising the fragment 6052 in neural text output 6050, save button 6048, cancel button 6046, navigation controls 6080 and 6082 (e.g., as illustrated in the transition from state 6022*d* to state 6022*e* of the system user interface 6020).

In some embodiments, the computer system detects a user input selecting a respective option of the plurality of selectable options corresponding to suggestions for revising the token. In response to detecting the user input selecting the respective option, the computer system replaces the token with the respective option in the text content displayed in the preview region. For example, in response to detecting a user input selecting the option 6086 (e.g., in response to detecting a neural-based input that responds to the command "1" associated with the option 6086), the computer system replaces the fragment 6054 in the neural text input 6050 with the fragment 6054*a* that is associated the selection option 6086. In some embodiments, revision selections made through the system user interface are stored as correction events and associated with corresponding neural data, feature data, decoded variants, and selected replacement text. The correction events can be stored locally in the computing device 140 and/or transmitted to the server system 160 for use by the operational pipeline 524 in updating one or more data processing models 568 or one or more data processing models 480. In some embodiments, the correction events are used to adapt user-specific thresholds, command vocabularies, or revision-option ordering, thereby reducing future decoding errors and improving accuracy of subsequent neural text generation for the same user.

In some embodiments, detecting the user input selecting the respective option for revising the token includes decoding, by the computer system, brain signals corresponding to instructions to execute a respective command associated with the respective option. In some embodiments, the plurality of selectable options corresponding to suggestions for revising the token are each associated with a respective command, where a respective command is, optionally, displayed or visually indicated in the system user interface in proximity to the respective option. In some embodiments, the decoded brain signals correspond to speech signals (e.g., an attempt speech that corresponds to or speaks the command). For example, in FIG. 6J, the option 6072 includes visual indication 6072*a* of a command "1" that when executed (e.g., in response to detecting neural based input of the command "1") causes the computing device 140 to select the option 6072.

In some embodiments, in conjunction with initiating the process for revising the text content, the computer system automatically selects a first option of the plurality of selectable options corresponding to suggestions for revising the token, and the computer system replaces the token with the first option in the text content displayed in the preview region. For example, in FIG. 6K, in the state 6022*e* of the system user interface, option 6072 is automatically preselected in response to activating the refine mode and initiating the process for revising the neural text output 6050.

In some embodiments, generating the instructions to display the plurality of selectable options corresponding to suggestions for revising the token includes generating instructions to display visual indications of commands associated with respective options of the plurality of selectable options. A respective command associated with a respective option of the plurality of selectable options, when executed, causes the respective option to be selected. In some embodiments, the options corresponding to suggestions for revising the token are associated with respective commands and visual indications of the respective commands are displayed (e.g., within affordances corresponding to the options or near the affordances corresponding to the options). For example, in FIG. 6J, the visual indication 6060*a* of the command "0" is displayed within option 6060, the visual indication 6062*a* of the command "1" is displayed within option 6062, and the visual indication 6064*a* of the command "2" is displayed within option 6064. In some embodiments, the visual indications include integer numbers corresponding to a position of the respective option in a sequence of the plurality of selectable options corresponding to suggestions for revising the token. For example, if an option is listed first, a visual indication of a respective command associated with the options is "1"; if an option is listed second, a visual indication of a respective command associated with the options is "2;" if an option is listed third, a visual indication of a respective command associated with the options is "3; and so on. In some embodiments, the integer numbers corresponding to commands for that do not necessarily follow an order in which the plurality of selectable options are arranged.

In some embodiments, an application user interface that includes a text region (e.g., a text field, a text bar, a text box, a text editing area, a search box, and/or other user interface element that is configured to receive text as input) is displayed at a time the instruction to enter text is received. For example, in FIG. 6C, the user interface 6010 with text bar 6012 of the messages application is displayed when the user 6016's brain signals are decoded to generated neural text output 6018, where the user interface 6010 of the messages application is different from the system user interface 6022. The application user interface corresponds to an application that is different from the system application, and the text region of the application is configured to receive text input. The computer system detects a user input (e.g., a touch input, a hand gesture, a mouse click, an air gesture, a gaze input, and/or decoded brain signals that correspond to attempted speech, movement, or otherwise an attempt to control an effector) requesting to exit the process for revising the content. The method 700 includes, in response to the detecting the user input requesting to exit the process for revising the content: in accordance with a determination that a threshold amount of time has passed (e.g., a predetermined amount of time or a dynamically determined threshold amount of time), the computer system automatically submit the text content in the preview region to the text region of the application. For example, a timeout finalization process is illustrated in FIGS. 6F-6G, where the neural text output 6018 in the preview text bar 6020 is automatically transmitted to text bar 6012 of the messages application. In some embodiments, the text content that is automatically submitted to the text region of the application includes revised text content in response to user inputs received during the revision process or the original text content without revisions (e.g., as illustrated in FIG. 6O-6P).

In some embodiments, after exiting the process for revising the content, the computer system detects a user input (e.g., a touch input, a hand gesture, a mouse click, an air gesture, a gaze input, and/or decoded brain signals that correspond to attempted speech, movement, or otherwise an attempt to control an effector) requesting to submit the text content in the preview region to the text region of the application. In response to user input requesting to submit the text content in the preview region to the text region of the application, submitting the text content in the preview region to the text region of the application. For example, in FIG. 6H, the user 6016 can manually submit the preview of neural text output from the preview text bar 6020 to the text bar 6012 of the messages application in response to a selection of return control 6021 (e.g., as illustrated by state 6028*e* of the preview text bar 6020).

In some embodiments, two or more tokens of the text content in the preview region are identified as targets for revision. For example, FIG. 6K illustrates that two fragments 6052 and 6054 are targeted for revision in the neural text output 6050.

In some embodiments, while a first token of the two or more tokens is selected, the computer system generates instructions to display a first plurality of selectable options, corresponding to suggestions for revising the first token. For example, while the fragment 6052 is in focus, options 6070-6076 corresponding to suggestions for revising the fragment 6052 are displayed in the system user interface 6022 (e.g., state 6022*e* of the system user interface 6022), and while the fragment 6054 is in focus, options 6084-6086 corresponding to suggestions for revising the fragment 6054 are displayed in the system user interface 6022 (e.g., state 6022*g* of the system user interface 6022). The method 7000, includes, in response to initiating the process for revising the text content includes, the computer system generates instructions to display a set of navigation controls associated with the two or more tokens that are identified as targets for revision. For example, the navigation controls 6080 and 6082 are displayed in the system user interface 6022, as illustrated by state 6022*e* in FIG. 6K. The computer system detects a user input selecting (e.g., a touch input, a hand gesture, a mouse click, an air gesture, a gaze input, and/or decoded brain signals that correspond to attempted speech, movement, or otherwise an attempt to control an effector) a first control of the set of navigation controls. In response to detecting the user input selecting the first control of the set of navigation controls, the computer system selects a second token of the two or more tokens and generates instructions to display a second plurality of selectable options corresponding to suggestions for revising the second token. For example, the computer system changes focus from the fragment 6052 in state 6022*e* to the fragment 6054 in state 6022*g* in response to detecting a selection input directed toward the navigation control 6082.

In some embodiments, generating instructions to display the first plurality of selectable options corresponding to suggestions for revising the first token includes generating instructions to display visual indications of commands associated with respective options of the first plurality of selectable options, and a respective command associated with a first respective option of the first plurality of selectable options, when executed, causes the first respective option to be selected. In some embodiments, generating instructions to display the second plurality of selectable options corresponding to suggestions for revising the first token includes generating instructions to display visual indications of commands associated with respective options of the second plurality of selectable options, and a respective command associated with a second respective option of the first plurality of selectable options, when executed, causes the second respective option to be selected. In some embodiments, the first respective option and/or the second respective options are executed in response to instructions corresponding to decoded brain signals associated with the command. For example, in state 6022*e* in FIG. 6K, the option 6072 is selected in response to detecting a neural-based input that corresponds to the command "1" associated with option 6072 and illustrated by visual indication 6072*a*, and, in state 6022*g* in FIG. 6K, the option 6086 is selected in response to detecting a neural-based input that corresponds to the command "1" associated with option 6068 and illustrated by visual indication 6086*a*.

In some embodiments, the text content is a first variant of a plurality of variants based on the set of decoded brain signals, where the plurality of variants are generated by a language model (e.g., data processing models 480 and/or data processing models 568) and the plurality of variants, including the first variant, are within a respective threshold of a cost function (e.g., character edit distance, or other word-based cost function and/or heuristic). Optionally, the threshold character edit distance is automatically determined by the language model or manually parameterized by a user. The text content is associated with a first confidence score that is lower than confidence scores of other variants of the plurality of variants. In some embodiments, the token that is identified as a target for revision in the first variant has an edit distance from a corresponding token in other variants that is higher relative to edit distances between other tokens in the first variant and corresponding tokens in other variants of the plurality of variants. In some embodiments, the text content meets refinement criteria in accordance with determination that a confidence score of the text content, generated by the language model, is lower relative to confidence scores of alternative text outputs, generated by the language model. For example, the language model associates a respective sentence has a low score relative to other possible sentences with a small character edit distance to the current sentence (e.g., with all values parameterized by the user or a model). Tokens for revision can be identified by where the edit distances are higher.

In some embodiments, based on the set of decoded brain signals, the computer system generates a plurality of textual output variants that are ranked based on confidence score of accuracy using a language model (e.g., a beam search). The computer system selects a subset of the plurality of textual output variants within a respective range (e.g., an absolute or relative range) from a top variant (e.g., actual variant that is entered in the preview region) of the plurality of textual output variants, wherein tokens in the subset of the plurality of textual output variants that different from tokens in top variant are identified as tokens for revision.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best use the invention and various described embodiments with various modifications as are suited to the particular use contemplated.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

Turning now to some example embodiments:

(A1) In accordance with some embodiments, a method is performed at a computer system that is in communication with a display generation component and one or more input devices, the method comprising (i) decoding a set of brain signals that are received from a brain of a human subject, wherein the set of brain signals is associated with attempted activation of motor functions of the human subject; (ii) determining that the decoded set of brain signals includes an instruction to enter text; (iii) in accordance with the determining that the decoded set of signals includes an instruction to enter text, generating instructions to display, via the display generation component, a preview of text content in a preview region of a system user interface for revising text content of a system application, wherein the text content is generated based on the decoded set of brain signals and the text content includes one or more tokens: (iv) in accordance with a determination that the text content meets a set of one or more refinement criteria, wherein the set of one or more refinement criteria includes a criterion that a token from the one or more tokens is identified as a target for revision, generating instructions to cause the token to be visually emphasized relative to other tokens of the one or more tokens; (v) detecting a user input requesting initiation of a process for revising the text content; and (vi) in response to detecting the user input requesting initiation of the process for revising the text content, initiating the process for revising the text content, including generating instructions to display a plurality of selectable options corresponding to suggestions for revising the token.

(A2) In some embodiments of A1, the method further includes: in accordance with the determination that the text content meets the refinement criteria, generating instructions to display an option for initiating the process for revising the text content, wherein the user input requesting initiation of the process for revising the text content includes a user input selecting the option.

(A3) In some embodiments of A2, wherein the instructions to display the option for initiating the process for revising the text content includes an instruction to display a visual indication of a command associated with the option, wherein the command, when executed, causes the option to be selected.

(A4) In some embodiments of A3, the user input selecting the option for initiating the process is received as a first brain signal, and the process for revising the text content includes decoding the first brain signal to obtain an instruction to execute the command.

(A5) In some embodiments of A3, wherein the command corresponds to a key on a keyboard; and the user input selecting the option for initiating the process for revising the text content includes pressing the key on the keyboard.

(A6) In some embodiments of any of A3-A5, wherein the user input selecting the option for initiating the process for revising the text content includes a user input activating the command; and the method further includes in response to detecting the user input activating the command, generating an instruction to display a visual indication that the command is activated.

(A7) In some embodiments of any of A2-A6, wherein the option for initiating the process for revising the text content includes a user interface element that corresponds to a total number of tokens from the one or more tokens that are identified as a target for revision.

(A8) In some embodiments of any of A1-A7, the method further includes: (1) before receiving the instruction to enter text, detecting an event associated with an application; and (2) in response to detecting an event associated with an application, generating instructions to display an application user interface corresponding to the application, including: in accordance with a determination that the application user interface includes a text region configured to receive text input, automatically causing display of the preview region of the system user interface, wherein the preview region of the system user interface is configured to receive text input.

(A9) In some embodiments of A8, the preview region of the system user interface is different from the text region of the application user interface.

(A10) In some embodiments of any of A8-A9, the preview region of the system user interface is concurrently displayed with the application user interface, including the text region of the application user interface.

(A11) In some embodiments of any of A8-A10, the preview region of the system user interface is automatically generated by a system-level process.

(A12) In some embodiments of any of A1-A11, a first mode is active before the process for revising the text content is initiated, wherein in the first mode, the system application outputs text content based on the decoded set of brain signals; and the method includes: in conjunction with initiating the process for revising the text content, deactivating the first mode and activating a second mode different from the first mode, where in the second mode the content is revised in response to subsequent user inputs selecting one or more of the plurality of selectable options.

(A13) In some embodiments of any of A1-A12, wherein initiating the process for revising the text content includes generating instructions to display a set of controls for editing the text content in the text content in the preview region.

(A14) In some embodiments of A13, initiating the process for revising the text content includes expanding the system user interface to include the plurality of selectable options corresponding to suggestions for revising the token and the set of controls for editing the text content in the preview region.

(A15) In some embodiments of any of A1-A14, the method further includes (i) detecting a user input selecting a respective option of the plurality of selectable options corresponding to suggestions for revising the token; and (ii) in response to detecting the user input selecting the respective option, replacing the token with the respective option in the text content displayed in the preview region.

(A16) In some embodiments of A15, the user input selecting the respective option for revising the token is received as a second brain signal, and the process for revising token includes decoding the second brain signal to obtain an instruction to execute a command associated with the respective option.

(A17) In some embodiments of any of A1-A16, the method further includes, in conjunction with initiating the process for revising the text content: (i) automatically selecting a first option of the plurality of selectable options corresponding to suggestions for revising the token; and (ii) replacing the token with the first option in the text content displayed in the preview region.

(A18) In some embodiments of any of A1-A17, wherein generating the instructions to display the plurality of selectable options corresponding to suggestions for revising the token includes generating instructions to display visual indications of commands associated with respective options of the plurality of selectable options; wherein a respective command associated with a respective option of the plurality of selectable options, when executed, causes the respective option to be selected.

(A19) In some embodiments of any of A1-A18, an application user interface that includes a text region is displayed at a time the instruction to enter text is received; the application user interface corresponds to an application that is different from the system application; and the text region of the application is configured to receive text input.

(A20) In some embodiments of A19, the method further includes (1) detecting a user input requesting to exit the process for revising the content; and (2) in response to the detecting the user input requesting to exit the process for revising the content: in accordance with a determination that a threshold amount of time has passed, automatically submitting the text content in the preview region to the text region of the application.

(A21) In some embodiments of A20, the method further includes (1) after exiting the process for revising the content, detecting a user input requesting to submit the text content in the preview region to the text region of the application; and (2) in response to user input requesting to submit the text content in the preview region to the text region of the application, submitting the text content in the preview region to the text region of the application.

(A22) In some embodiments of any of A1-A21, two or more tokens of the text content in the preview region are identified as targets for revision, and wherein: (1) while a first token of the two or more tokens is selected, generating instructions to display a first plurality of selectable options, corresponding to suggestions for revising the first token; and (2) the method includes: (2a) in response to initiating the process for revising the text content, generating instructions to display a set of navigation controls associated with the two or more tokens that are identified as targets for revision; (2b) detecting a user input selecting a first control of the set of navigation controls; and (2c) in response to detecting the user input selecting the first control of the set of navigation controls: (i) selecting a second token of the two or more tokens; and (ii) generating instructions to display a second plurality of selectable options corresponding to suggestions for revising the second token.

(A23) In some embodiments of A22, (i) generating instructions to display the first plurality of selectable options corresponding to suggestions for revising the first token includes generating instructions to display visual indications of commands associated with respective options of the first plurality of selectable options, and a respective command associated with a first respective option of the first plurality of selectable options, when executed, causes the first respective option to be selected; and (ii) generating instructions to display the second plurality of selectable options corresponding to suggestions for revising the first token includes generating instructions to display visual indications of commands associated with respective options of the second plurality of selectable options, and a respective command associated with a second respective option of the first plurality of selectable options, when executed, causes the second respective option to be selected.

(A24) In some embodiments of A1-A23, (i) the text content includes a first variant of a plurality of variants based on the set of decoded brain signals, where the plurality of variants are generated by a language model and the plurality of variants are within a respective threshold of a cost function; and (ii) the first variant is associated with a first confidence score that is lower than confidence scores of other variants of the plurality of variants.

(A25) In some embodiments of A1-A24, the method further includes: (i) based on the set of decoded brain signals, generating a plurality of textual output variants that are ranked based on confidence score of accuracy using a language model; and (ii) selecting a subset of the plurality of textual output variants within a respective range from a top variant of the plurality of textual output variants, wherein tokens in the subset of the plurality of textual output variants that different from tokens in top variant are identified as tokens for revision.

(A26) In some embodiments of any of A1-A25, the text content meets the set of one or more refinement criteria when the text content includes one or more of: a spelling error, a grammar-related error, a contextually inappropriate word, a subject-verb agreement error, a misplaced modifier, use of passive voice, and a syntactic error.

(A27) In some embodiments of any of A1-A26, wherein (1) a decoder model is applied to decode the set of brain signals and generate the text content based on the decoded set of brain signals; and (2) the text content meets the set of one or more refinement criteria (2a) when one or more statistical properties of the set of decoded brain signals indicate an ambiguity or an error in the text content or (2b) when a decoding confidence score output by the decoder model is below a threshold confidence score.

(B1) In accordance with some embodiments, a brain computer interface (BCI) system includes an implant device configured to record a set of neural signals from a brain of a human subject, wherein the set of neural signals is associated with attempted activation of motor functions of the human subject. The BCI system includes one or more processors and memory coupled to the one or more processors. The memory stores one or more programs configured for execution by the one or more processors. The one or more programs include instructions for (i) decoding the set of neural signals to obtain a neural text output; (ii) in accordance with the decoding, generating instructions to display a preview of text content in a preview region of a system user interface, wherein the text content is generated based on the decoded set of neural signals and the text content includes one or more tokens; (iii) identifying, based on a property of the decoded neural text output, a token from the one or more tokens as a target for revision; (iv) generating instructions to cause the token to be visually emphasized relative to other tokens of the one or more tokens; (v) detecting a user input requesting initiation of a process for revising the text content; and (vi) in response to detecting the user input requesting initiation of the process for revising the text content, initiating the process for revising the text content, including generating instructions to display a plurality of selectable options corresponding to suggestions for revising the token.

(B2) In some embodiments of B1, the one or more programs include instructions for performing the method of any of A2-A27.

(C1) In accordance with some embodiments, a computer system in communication with a display generation component and one or more input devices comprises one or more processors and memory storing one or more programs, wherein the one or more programs are configured to be executed by the one or more processors. The one or more programs include instructions for performing the method of any of A1-A27.

(D1) In accordance with some embodiments, a computer readable storage medium stores one or more programs, the one or more programs comprising instructions that, when executed by a computer system that is in communication with a display generation component and one or more input devices, cause the computer system to perform the method of any of A1-A27.

(E1) In accordance with some embodiments, an information processing apparatus for use in a computer system that is in communication with a display generation component and one or more input devices, comprises means for performing the method of any of A1-A25.

(F1) In accordance with some embodiments, a graphical user interface on a computer system that is in communication with a display generation component and one or more input devices, the computer system comprising memory and one or more processors to execute one or more programs stored in the memory, the graphical user interface comprising user interfaces displayed in accordance with any of the methods of A1-A27.

(G1) In accordance with some embodiments, a computer system is in communication with a display generation component and one or more input devices, the computer system comprises means for performing the method of any of A1-A27.

It will be understood that, although the terms “first,” “second,” etc. may be used herein to describe various elements, these elements should not be limited by these terms. These terms are only used to distinguish one element from another. The terminology used herein is for the purpose of describing particular embodiments only and is not intended to be limiting of the claims. As used in the description of the embodiments and the appended claims, the singular forms “a,” “an” and “the” are intended to include the plural forms as well, unless the context clearly indicates otherwise. It will also be understood that the term “and/or” as used herein refers to and encompasses any and all possible combinations of one or more of the associated listed items. It will be further understood that the terms “comprises” and/or “comprising,” when used in this specification, specify the presence of stated features, integers, steps, operations, elements, and/or components, but do not preclude the presence or addition of one or more other features, integers, steps, operations, elements, components, and/or groups thereof.

As used herein, the term “plurality” denotes two or more. For example, a plurality of components indicates two or more components. The term “determining” encompasses a wide variety of actions and, therefore, “determining” can include calculating, computing, processing, deriving, investigating, looking up (e.g., looking up in a table, a database or another data structure), ascertaining and the like. Also, “determining” can include receiving (e.g., receiving information), accessing (e.g., accessing data in a memory) and the like. Also, “determining” can include resolving, selecting, choosing, establishing and the like.

The phrase "based on" does not mean "based only on," unless expressly specified otherwise. In other words, the phrase "based on" describes both "based only on" and "based at least on."

As used herein, the term "exemplary" means "serving as an example, instance, or illustration," and does not necessarily indicate any preference or superiority of the example over any other configurations or embodiments.

As used herein, the term "and/or" encompasses any combination of listed elements. For example, "A, B, and/or C" entails each of the following possibilities: A only, B only, C only, A and B without C, A and C without B, B and C without A, and a combination of A, B, and C.

The terminology used in the description of the invention herein is for the purpose of describing particular embodiments only and is not intended to be limiting of the invention. As used in the description of the invention and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

What is claimed is:

1. A method performed at a computer system that is in communication with a display generation component and one or more input devices, the method comprising:

decoding a set of brain signals that are received from a brain of a human subject, wherein the set of brain signals is associated with attempted activation of motor functions of the human subject;

determining that the decoded set of brain signals includes an instruction to enter text;

in accordance with the determination that the decoded set of signals includes an instruction to enter text, generating instructions to display, via the display generation component, a preview of text content in a preview region of a system user interface for revising text content of a system application, wherein the text content is generated based on the decoded set of brain signals and the text content includes one or more tokens:

in accordance with a determination that the text content meets a set of one or more refinement criteria, wherein the set of one or more refinement criteria includes a criterion that a token from the one or more tokens is identified as a target for revision, generating instructions to cause the token to be visually emphasized relative to other tokens of the one or more tokens;

detecting a user input requesting initiation of a process for revising the text content; and in response to detecting the user input requesting initiation of the process for revising the text content, initiating the process for revising the text content, including generating instructions to display a plurality of selectable options corresponding to suggestions for revising the token.

2. The method of claim 1, further comprising:

in accordance with the determination that the text content meets the refinement criteria, generating instructions to display an option for initiating the process for revising the text content, wherein the user input requesting initiation of the process for revising the text content includes a user input selecting the option.

3. The method of claim 2, wherein the instructions to display the option for initiating the process for revising the text content includes an instruction to display a visual indication of a command associated with the option, wherein the command, when executed, causes the option to be selected.

4. The method of claim 3, wherein the user input selecting the option for initiating the process is received as a first brain signal, and the process for revising the text content includes decoding the first brain signal to obtain an instruction to execute the command.

5. The method of claim 3, wherein:

the command corresponds to a key on a keyboard; and the user input selecting the option for initiating the process for revising the text content includes pressing the key on the keyboard.

6. The method of claim 3, wherein:

the user input selecting the option for initiating the process for revising the text content includes a user input activating the command; and the method includes:

in response to detecting the user input activating the command, generating an instruction to display a visual indication that the command is activated.

7. The method of claim 2, wherein the option for initiating the process for revising the text content includes a user interface element that corresponds to a total number of tokens from the one or more tokens that are identified as a target for revision.

8. The method of claim 1, further comprising:

before receiving the instruction to enter text, detecting an event associated with an application; and in response to detecting an event associated with an application, generating instructions to display an application user interface corresponding to the application, including:

in accordance with a determination that the application user interface includes a text region configured to receive text input, automatically causing display of the preview region of the system user interface, wherein the preview region of the system user interface is configured to receive text input.

9. The method of claim 1, wherein:

a first mode is active before the process for revising the text content is initiated, wherein in the first mode, the system application outputs text content based on the decoded set of brain signals; and the method further comprises:

in conjunction with initiating the process for revising the text content, deactivating the first mode and activating a second mode different from the first mode, where in the second mode the content is revised in response to subsequent user inputs selecting one or more of the plurality of selectable options.

10. The method of claim 1, wherein initiating the process for revising the text content includes:

generating instructions to display a set of controls for editing the text content in the text content in the preview region; and expanding the system user interface to include the plurality of selectable options corresponding to suggestions for revising the token and the set of controls for editing the text content in the preview region.

11. The method of claim 1, wherein:

generating the instructions to display the plurality of selectable options corresponding to suggestions for revising the token includes generating instructions to display visual indications of commands associated with respective options of the plurality of selectable options;

wherein a respective command associated with a respective option of the plurality of selectable options, when executed, causes the respective option to be selected.

12. The method of claim 1, wherein:

an application user interface that includes a text region is displayed at a time the instruction to enter text is received;

the application user interface corresponds to an application that is different from the system application; and the text region of the application is configured to receive text input.

13. The method of claim 12, further comprising:

detecting a user input requesting to exit the process for revising the content; and in response to the detecting the user input requesting to exit the process for revising the content:

in accordance with a determination that a threshold amount of time has passed, automatically submitting the text content in the preview region to the text region of the application.

14. The method of claim 13, further comprising:

after exiting the process for revising the content, detecting a user input requesting to submit the text content in the preview region to the text region of the application; and in response to user input requesting to submit the text content in the preview region to the text region of the application, submitting the text content in the preview region to the text region of the application.

15. The method of claim 1, wherein two or more tokens of the text content in the preview region are identified as targets for revision, and wherein:

while a first token of the two or more tokens is selected, generating instructions to display a first plurality of selectable options, corresponding to suggestions for revising the first token; and the method includes:

in response to initiating the process for revising the text content, generating instructions to display a set of navigation controls associated with the two or more tokens that are identified as targets for revision;

detecting a user input selecting a first control of the set of navigation controls; and in response to detecting the user input selecting the first control of the set of navigation controls:

selecting a second token of the two or more tokens; and generating instructions to display a second plurality of selectable options corresponding to suggestions for revising the second token.

16. The method of claim 15, wherein:

generating instructions to display the first plurality of selectable options corresponding to suggestions for revising the first token includes generating instructions to display visual indications of commands associated with respective options of the first plurality of selectable options, and a respective command associated with a first respective option of the first plurality of selectable options, when executed, causes the first respective option to be selected; and generating instructions to display the second plurality of selectable options corresponding to suggestions for revising the first token includes generating instructions to display visual indications of commands associated with respective options of the second plurality of selectable options, and a respective command associated with a second respective option of the first plurality of selectable options, when executed, causes the second respective option to be selected.

17. The method of claim 1, wherein:

the text content includes a first variant of a plurality of variants based on the set of decoded brain signals, where the plurality of variants are generated by a language model and the plurality of variants are within a respective threshold of a cost function; and the first variant is associated with a first confidence score that is lower than confidence scores of other variants of the plurality of variants.

18. The method of claim 1, further comprising:

based on the decoded set of brain signals, generating a plurality of textual output variants that are ranked based on confidence score of accuracy using a language model; and selecting a subset of the plurality of textual output variants within a respective range from a top variant of the plurality of textual output variants, wherein tokens in the subset of the plurality of textual output variants that different from tokens in top variant are identified as tokens for revision.

19. A non-transitory computer readable storage medium storing one or more programs, the one or more programs comprising instructions that, when executed by a computer system that is in communication with a display generation component and one or more input devices, cause the computer system to:

decode a set of brain signals that are received from a brain of a human subject, wherein the set of brain signals is associated with attempted activation of motor functions of the human subject;

determine that the decoded set of brain signals includes an instruction to enter text;

in accordance with the determination that the decoded set of signals includes an instruction to enter text, generate instructions to display, via the display generation component, a preview of text content in a preview region of a system user interface for revising text content of a system application, wherein the text content is generated based on the decoded set of brain signals and the text content includes one or more tokens:

in accordance with a determination that the text content meets a set of one or more refinement criteria, wherein the set of one or more refinement criteria includes a criterion that a token from the one or more tokens is identified as a target for revision, generate instructions to cause the token to be visually emphasized relative to other tokens of the one or more tokens;

detect a user input requesting initiation of a process for revising the text content; and in response to detecting the user input requesting initiation of the process for revising the text content, initiate the process for revising the text content, including generating instructions to display a plurality of selectable options corresponding to suggestions for revising the token.

20. A brain computer interface (BCI) system, comprising:

an implant device configured to record a set of neural signals from a brain of a human subject, wherein the set of neural signals is associated with attempted activation of motor functions of the human subject;

one or more processors; and memory storing one or more programs, wherein the one or more programs are configured to be executed by the one or more processors, the one or more programs including instructions for:

decoding the set of neural signals to obtain a neural text output;

in accordance with the decoding, generating instructions to display a preview of text content in a preview region of a system user interface, wherein the text content is generated based on the decoded set of neural signals and includes one or more tokens;

identifying, based on a property of the neural text output, a token from the one or more tokens as a target for revision;

generating instructions to cause the token to be visually emphasized relative to other tokens of the one or more tokens;

detecting a user input requesting initiation of a process for revising the text content; and in response to detecting the user input requesting initiation of the process for revising the text content, initiating the process for revising the text content, including generating instructions to display a plurality of selectable options corresponding to suggestions for revising the token.

* * * * *